United States Patent
Mayer et al.

(10) Patent No.: US 6,340,670 B1
(45) Date of Patent: Jan. 22, 2002

(54) ACETAL BENZYLMALTOSIDES AS INHIBITORS OF SMOOTH MUSCLE CELL PROLIFERATION

(75) Inventors: Scott C. Mayer, Robbinsville, NJ (US); Paul J. Dollings, Newtown, PA (US); Robert E. McDevitt, Somerset, NJ (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/447,009

(22) Filed: Nov. 22, 1999

Related U.S. Application Data

(60) Provisional application No. 60/126,443, filed on Nov. 24, 1998.

(51) Int. Cl.$^7$ ..................... A61K 31/702; C07H 15/203
(52) U.S. Cl. ..................... 514/25; 514/53; 536/4.1; 536/17.2; 536/123.13
(58) Field of Search .................. 536/4.1, 17.2, 536/123.13; 514/25, 24

(56) References Cited

U.S. PATENT DOCUMENTS

| | | | |
|---|---|---|---|
| 2,752,334 A | 6/1956 | Walton | 260/211 |
| 4,307,194 A | * 12/1981 | Frommer et al. | 435/122 |
| 4,431,637 A | 2/1984 | Upeslacis et al. | 424/180 |
| 5,019,562 A | 5/1991 | Folkman et al. | 514/58 |
| 5,037,973 A | 8/1991 | Meinetsberger | 536/53 |
| 5,296,588 A | 3/1994 | Au et al. | 536/1.11 |
| 5,310,542 A | 5/1994 | Au et al. | 424/52 |
| 5,336,765 A | 8/1994 | Au et al. | 536/18.5 |
| 5,464,827 A | 11/1995 | Soll | 514/58 |
| 5,498,775 A | 3/1996 | Novak et al. | 514/25 |
| 5,773,420 A | * 6/1998 | Nguyen et al. | 514/25 |

FOREIGN PATENT DOCUMENTS

| | | |
|---|---|---|
| EP | 0312086 | 4/1989 |
| EP | 0312087 | 4/1989 |
| EP | 0356275 | 2/1990 |
| EP | 0454220 | 10/1991 |
| EP | 0550106 | 7/1993 |
| EP | 0551675 | 7/1993 |
| WO | 9006755 | 6/1990 |
| WO | 9309790 | 5/1993 |
| WO | 9614324 | 5/1996 |
| WO | 9614325 | 5/1996 |

OTHER PUBLICATIONS

Zehavi, Carbohyd. Res., 1986, 151, 371.
Reilly et al., Drug Development Research, 1993, 29, 137.
Klein et al., Liebigs Ann. Chem., 1987, 485–489.
Durette et al., Carbohydrate Research, 1978, 67, 484–490.
Bertho, Liebigs Ann. Chem., 1949, 562, 229–239.
Kopper et al., Carbohydrate Research, 1989, 193, 296–302.
Zehavi et al., Carbohydrate Research, 1983, 124, 23–34.
Zehavi et al., Carbohydrate Research, 1992, 228, 255–263.
Connors et al., Herba Polonica, 1998, 44, 33–38.
Morales et al., Angew. Chem. Int. Ed., 1988, 37 (5), 654–657.
Hirooka et al., Bull. Chem. Soc. Jpn., 1998, 71(12), 2893–2902.
Koizumi et al., Carbohydr. Res., 1978, 63, 283–287.

\* cited by examiner

*Primary Examiner*—Gary Geist
*Assistant Examiner*—Leigh C. Maier
(74) *Attorney, Agent, or Firm*—Michael R. Nagy

(57) ABSTRACT

This invention provides smooth muscle cell proliferation inhibitors of formula I having the structure

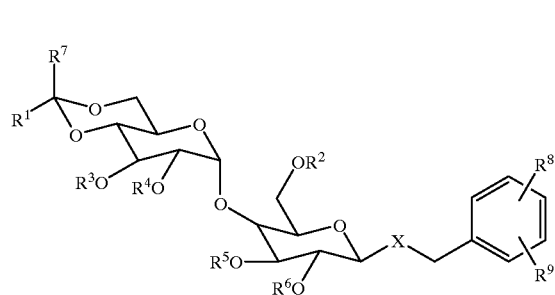

with the variables defined herein.

24 Claims, No Drawings

ACETAL BENZYLMALTOSIDES AS INHIBITORS OF SMOOTH MUSCLE CELL PROLIFERATION

This application claims the benefit of U.S. Provisional Application No. 60/126,443, which was converted from U.S. patent application Ser. No. 09/198,803, filed Nov. 24, 1998, pursuant to a petition filed under 37 C.F.R. 1.53(c)(2)(i).

BACKGROUND OF THE INVENTION

This invention relates to the use of substituted 4',6'-acetal benzylmaltosides as smooth muscle cell proliferation inhibitors and as therapeutic compositions for treating diseases and conditions which are characterized by excessive smooth muscle proliferation such as restenosis.

All forms of vascular reconstruction such as angioplasty and vein bypass procedures effect a response to injury that ultimately leads to smooth muscle cell (SMC) proliferation and subsequently, deposition of profuse amounts of extracellular matrix (Clowes, A. W.; Reidy, M. A. J. *Vasc. Surg* 1991, 13, 885). These events are also central processes in the pathogenesis of atherosclerosis (Raines E. W.; Ross R. *Br. Heart J.* 1993, 69 (Supplement), S. 30) as well as transplant arteriosclerosis (Isik, F. F.; McDonald, T. O.; Ferguson, M.; Yamanaka, E.; Gordon *Am. J. Pathol.* 1992, 141, 1139). In the case of restenosis following angioplasty, clinically relevant solutions for controlling SMC proliferation through pharmacological intervention have remained elusive to date (Herrman, J. P. R.; Hermans, W. R. M.; Vos, J.; Serruys P. W. *Drugs* 1993, 4, 18 and 249). Any successful approach to selective SMC proliferation inhibition must not interfere with endothelial cell repair or the normal proliferation and function of other cells (Weissberg, P. L.; Grainger, D. J.; Shanahan C. M.; Metcalfe, J. C. *Cardiovascular Res.* 1993, 27, 1191).

The glycosaminoglycans heparin and heparan sulfate are endogenous inhibitors of SMC proliferation, yet are able to promote endothelial cell growth (Castellot, J. J. Jr.; Wright, T. C.; Karnovsky, M. J. *Seminars in Thrombosis and Hemostasis* 1987, 13, 489). However, the full clinical benefits of heparin, heparin fragments, chemically modified heparin, low molecular weight heparins, and other heparin mimicking anionic polysaccharides may be compromised due to other pharmacological liabilities (excessive bleeding arising from anticoagulation effects, in particular) coupled with heterogeneity of the various preparations (Borman, S. *Chemical and Engineering News*, Jun. 28, 27 1993,).

WO 96/14325 discloses acylated benzylglycosides as smooth muscle cell proliferation inhibitors. The compounds of the present invention differ in that the substituents on the carbohydrate backbone are different.

Zehavi, U.; Herchman, M. in *Carbohyd. Res.* 1986, 151, 371, disclosed 4-carboxy-2-nitrobenzyl 4-O-α-D-glucopyranosyl-β-D-glucopyranoside which is attached to a polymer for study as an acceptor in the glycogen synthase reaction. The compounds of the present invention differ in that the substituents on the benzyl groups are different and the use (smooth muscle antiproliferation) is different.

U.S. Pat. No. 5,498,775, WO96/14324, and U.S. Pat. No. 5,464,827 describe polyanionic benzylglycosides or cyclodextrins as smooth muscle cell proliferation inhibitors for treating diseases and conditions which are characterized by excessive smooth muscle proliferation. β-cyclodextrin tetradecasulfate has been described as a smooth muscle cell proliferation inhibitor and as an effective inhibitor of restenosis (Reilly, C. F.; Fujita, T.; McFall, R. C.; Stabilito, I. I.; Wai-se E.; Johnson, R. G. *Drug Development Research* 1993, 29, 137). U.S. Pat. No. 5,019,562 discloses anionic derivatives of cyclodextrins for treating pathological conditions associated with undesirable cell or tissue growth. WO 93/09790 discloses antiproliferative polyanionic derivatives of cyclodextrins bearing at least 2 anionic residues per carbohydrate residues. Meinetsberger (EP 312087 A2 and EP 312086 A2) describes the antithrombotic and anticoagulant properties of sulfated bis-aldonic acid amides. U.S. Pat. No. 4,431,637 discloses polysulfated phenolic glycosides as modulators of the complement system. The compounds of the present invention differ from all of the prior art in that the compounds (a) are benzylglycosylamides which bear no structural resemblance to heparin, sulfated cyclodextrins, or to sulfated lactobionic acid dimers, (b) contain no more than two contiguous sugar residues (disaccharide), (c) are of a defined structure, (d) and are not sulfated.

DESCRIPTION OF THE INVENTION

This invention provides benzylmaltosides of formula I

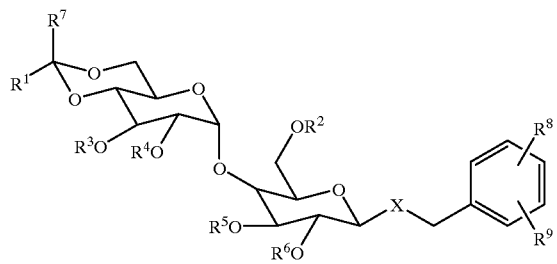

wherein

X is O or S;

R$^1$ is alkyl of 1–6 carbon atoms, haloalkyl of 1–6 carbon atoms, nitroalkyl of 1–6 carbon atoms, cyanoalkyl of 1–6 carbon atoms, alkoxyalkyl of 2–12 carbon atoms, phenyl mono-, di-, or tri-substituted with R$^8$, phenylalkyl of 7–10 carbon atoms, wherein the phenyl ring is mono-, di-, or tri-substituted with R$^8$, pyridyl substituted with R$^8$, furyl substituted with R$^8$, thienyl substituted with R$^8$, and thiazolyl substituted with R$^8$;

R$^2$ is hydrogen, acyl of 2–6 carbon atoms, haloacyl of 2–6 carbon atoms, nitroacyl of 2–7 carbon atoms, cyanoacyl of 2–7 carbon atoms, or trifluoromethylacyl of 3–8 carbon atoms, carboalkoxyacyl of 4–12 carbon atoms,

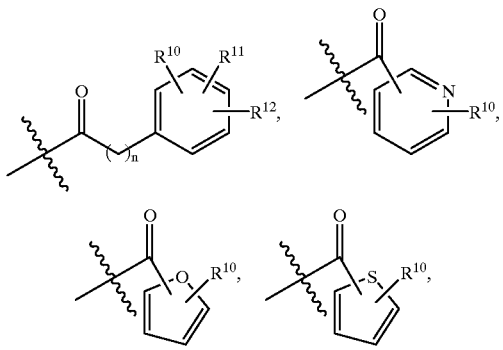

-continued

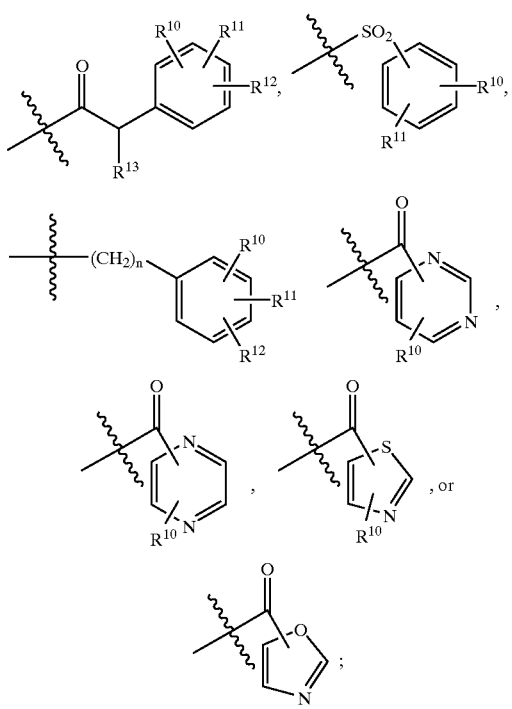

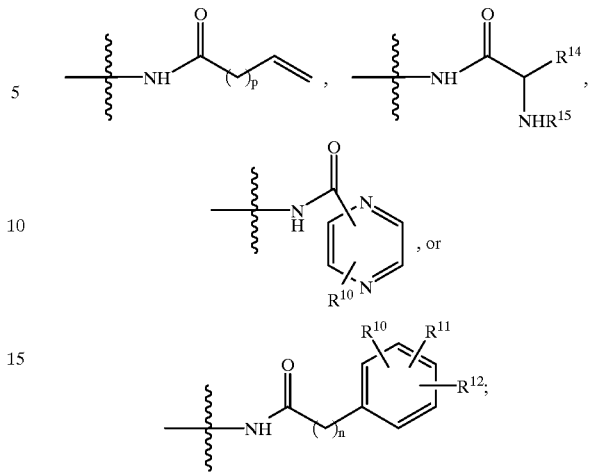

$R^3$, $R^4$, $R^5$, and $R^6$ are each, independently, hydrogen, acyl of 2–7 carbon atoms, benzoyl, wherein the phenyl moiety is mono-, di-, or tri-substituted with $R^8$, haloacyl of 2–7 carbon atoms, nitroacyl of 2–7 carbon atoms, cyanoacyl of 2–7 carbon atoms, or trifluoromethylacyl of 3–8 carbon atoms;

$R^7$ is hydrogen, methyl, or phenyl;

$R^8$ is hydrogen, alkyl of 1–6 carbon atoms, alkoxy of 1–6 carbon atoms, phenyl, —CN, —NO$_2$, halogen, or —CF$_3$;

$R^9$ is hydrogen, alkyl of 1–6 carbon atoms, alkoxy of 1–6 carbon atoms, phenyl, —CN, —NO$_2$, halogen, —CF$_3$, NHR$^3$, —NR$^3$R$^3$, —NR$^3$R$^{14}$, —NHCO$_2$R$^{14}$, —NHSO$_2$R$^{14}$,

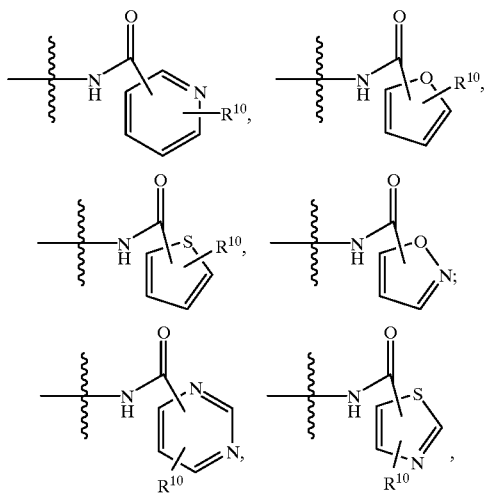

$R^{10}$, $R^{11}$, and $R^{12}$, are each, independently, hydrogen, alkyl of 1–6 carbon atoms, alkoxy of 1–6 carbon atoms, phenyl, —CN, —NO$_2$, halogen, —CF$_3$, acyl of 2–7 carbon atoms, or benzoyl, wherein the phenyl group or the phenyl moiety of the benzoyl group is optionally mono-, di-, or tri-substituted with alkyl of 1–6 carbon atoms, alkoxy of 1–6 carbon atoms, —CN, —NO$_2$, halogen, or —CF$_3$;

$R^{13}$ is hydrogen, alkyl of 1–6 carbon atoms, alkoxy of 1–6 carbon atoms, —CN, —NO$_2$, halogen, —CF$_3$, or phenyl group, wherein the phenyl moiety is optionally mono-, di-, or tri-substituted with alkyl of 1–6 carbon atoms, alkoxy of 1–6 carbon atoms, or halogen;

$R^{14}$ is alkyl of 1–6 carbon atoms;

$R^{15}$ is hydrogen, acyl of 2–7 carbon atoms, benzoyl, or —CO$_2$R$^{16}$;

$R^{16}$ is alkyl of 1–6 carbon atoms, benzyl, phenyl, or fluorenyl;

n=0–3;

p=0–6;

or a pharmaceutically acceptable salt thereof.

Alkyl includes both straight chain as well as branched moieties. Halogen means bromine, chlorine, fluorine, and iodine. When a compound of this invention contains a group that contains the same moiety more than once (i.e., when $R^9$ is —NR$^3$R$^3$), each of the moieties may be the same or different.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from organic and inorganic bases, preferably alkali metal salts, for example, sodium, lithium, or potassium. Acid addition salts can be prepared when Y is nitrogen or the compound of formula I contains a basic nitrogen, and base addition salts can typically be prepared when the compound of formula I contains a hydroxyl group.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

Preferred compounds of this invention are benzylmaltosides of formula I

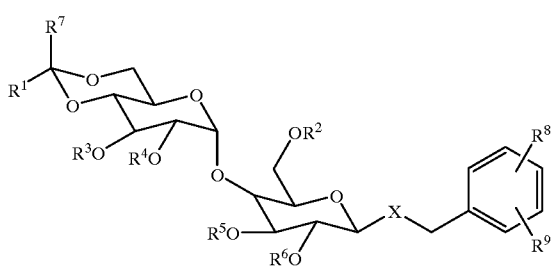

I wherein
X is O or S;
$R^1$ is alkyl of 1–6 carbon atoms, haloalkyl of 1–6 carbon atoms, nitroalkyl of 1–6 carbon atoms, cyanoalkyl of 1–6 carbon atoms, alkoxyalkyl of 2–12 carbon atoms, phenyl mono-, di-, or tri-substituted with $R^8$, phenylalkyl of 7–10 carbon atoms, wherein the phenyl ring is mono-, di-, or tri-substituted with $R^8$, pyridyl substituted with $R^8$, furyl substituted with $R^8$, thienyl substituted with $R^8$, and thiazolyl substituted with $R^8$;
$R^2$ is hydrogen, acyl of 2–6 carbon atoms, carboalkoxyacyl of 4–12 carbon atoms,

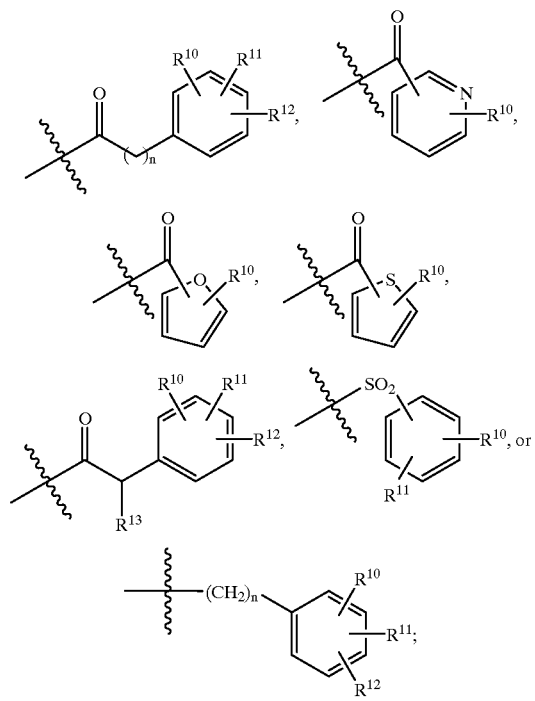

$R^3$, $R^4$, $R^5$, and $R^6$ are each, independently, hydrogen, or acyl of 2–7 carbon atoms;
$R^7$ is hydrogen, methyl, or phenyl;
$R^8$ is hydrogen, alkyl of 1–6 carbon atoms, alkoxy of 1–6 carbon atoms, phenyl, —CN, —NO$_2$, halogen, or —CF$_3$;

$R^9$ is hydrogen, —NO$_2$, halogen, —CF$_3$, —NHR$^3$, —NR$^3$R$^3$, —NR$^3$R$^{14}$, —NHCO$_2$R$^{14}$, —NHSO$_2$R$^{14}$,

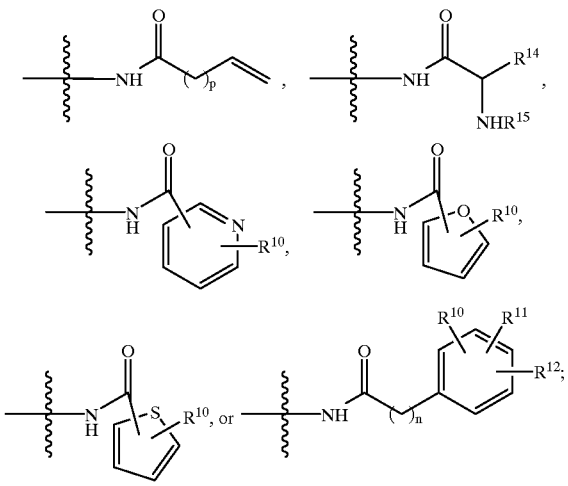

$R^{10}$, $R^{11}$, and $R^{12}$, are each, independently, hydrogen, alkyl of 1–6 carbon atoms, alkoxy of 1–6 carbon atoms, phenyl, —CN, —NO$_2$, halogen, —CF$_3$, acyl of 2–7 carbon atoms, or benzoyl, wherein the phenyl group or the phenyl moiety of the benzoyl group is optionally mono-, di-, or tri-substituted with alkyl of 1–6 carbon atoms, alkoxy of 1–6 carbon atoms, —CN, —NO$_2$, halogen, or —CF$_3$;
$R^{13}$ is hydrogen, alkyl of 1–6 carbon atoms, alkoxy of 1–6 carbon atoms, —CN, —NO$_2$, halogen, —CF$_3$, or phenyl group, wherein the phenyl moiety is optionally mono-, di-, or tri-substituted with alkyl of 1–6 carbon atoms, alkoxy of 1–6 carbon atoms, or halogen;
$R^{14}$ is alkyl of 1–6 carbon atoms;
$R^{15}$ is hydrogen, acyl of 2–7 carbon atoms, benzoyl, or —CO$_2$R$^{16}$;
$R^{16}$ is alkyl of 1–6 carbon atoms, benzyl, phenyl, or fluorenyl;
n=0–3;
p=0–6;
or a pharmaceutically acceptable salt thereof.

More preferred compounds of this invention are benzylmaltosides of formula I

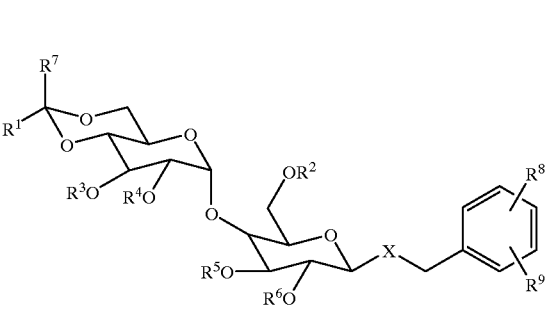

I wherein
X is O;
$R^1$ is alkyl of 1–6 carbon atoms, haloalkyl of 1–6 carbon atoms, nitroalkyl of 1–6 carbon atoms, cyanoalkyl of 1–6 carbon atoms, alkoxyalkyl of 2–12 carbon atoms, phenyl mono-, di-, or tri-substituted with $R^8$, phenylalkyl of 7–10 carbon atoms, wherein the phenyl ring is mono-, di-, or tri-substituted with $R^8$, or pyridyl substituted with $R^8$;

$R^2$ is hydrogen, acyl of 2–6 carbon atoms, carboalkoxyacyl of 4–12 carbon atoms,

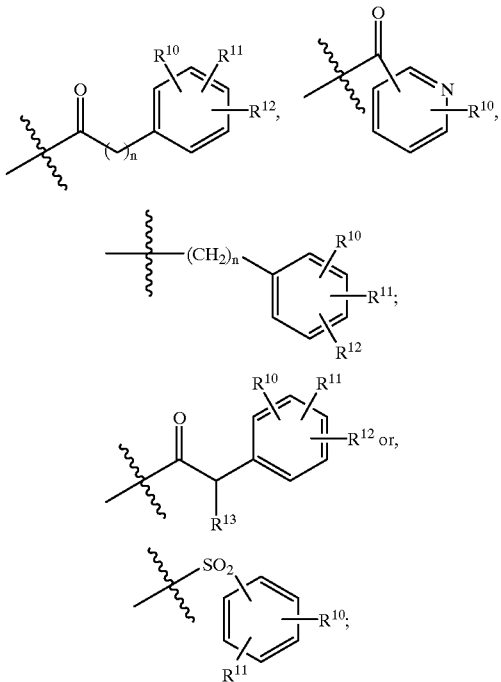

$R^3$, $R^4$, $R^5$, and $R^6$ are each, independently, hydrogen, or acyl of 2–7 carbon atoms;

$R^7$ is hydrogen;

$R^8$ is hydrogen, alkyl of 1–6 carbon atoms, —CN, or halogen; $R^9$ is hydrogen, —$NO_2$, halogen, —$CF_3$, —$NHR^3$, —$NR^3R^3$, —$NR^3R^{14}$, —$NHCO_2R^{14}$, —$NHSO_2R^{14}$,

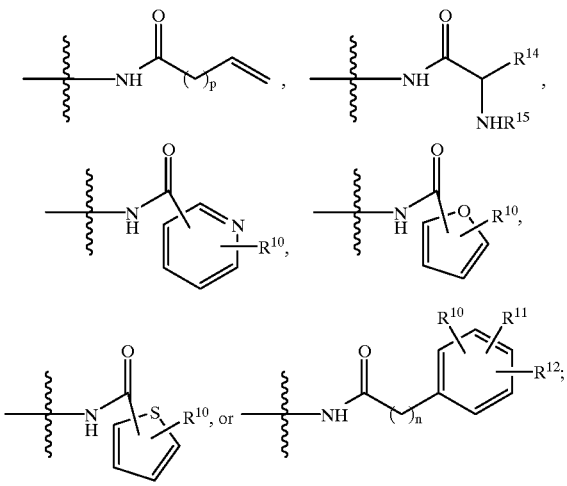

$R^{10}$, $R^{11}$, and $R^{12}$, are each, independently, hydrogen, alkyl of 1–6 carbon atoms, alkoxy of 1–6 carbon atoms, phenyl, —CN, —$NO_2$, halogen, —$CF_3$, acyl of 2–7 carbon atoms, or benzoyl, wherein the phenyl group or the phenyl moiety of the benzoyl group is optionally mono-, di-, or tri-substituted with alkyl of 1–6 carbon atoms, alkoxy of 1–6 carbon atoms, —CN, —$NO_2$, halogen, or —$CF_3$;

$R^{13}$ is hydrogen, alkyl of 1–6 carbon atoms, halogen, or phenyl group, wherein the phenyl moiety is optionally mono-, di-, or tri-substituted with alkyl of 1–6 carbon atoms, alkoxy of 1–6 carbon atoms, or halogen;

$R^{14}$ is alkyl of 1–6 carbon atoms;

$R^{15}$ is hydrogen, acyl of 2–7 carbon atoms, benzoyl, or —$CO_2R^{16}$;

$R^{16}$ is alkyl of 1–6 carbon atoms, or fluorenyl;

n=0–3;

p=0–6;

or a pharmaceutically acceptable salt thereof.

Specifically preferred compounds of this invention are:

N-{2-Chloro-5-[(4',6'-O-ethylidene)-β-D-maltosyloxymethyl]-phenyl}-acetamide or a pharmaceutically acceptable salt thereof;

(R)-N-[5-[[[6-O-Benzoyl-4-O-(4,6-O-ethylidene-α-D-glucopyranosyl)-β-D-glucopyranosyl]oxy]methyl]-2-chlorophenyl]acetamide or a pharmaceutically acceptable salt thereof;

(R)-N-[2-Chloro-5-[[[2,3-di-O-acetyl-6-O-benzoyl-4-O-(2,3-di-O-acetyl-4,6-O-ethylidene-α-D-glucopyranosyl)-β-D-glucopyranosyl]oxy]methyl]phenyl]acetamide or a pharmaceutically acceptable salt thereof;

N-{2-Chloro-5-[(4',6'-O-propylidene-β-D-maltosyl)-oxy-methyl]-phenyl}-acetamide or a pharmaceutically acceptable salt thereof;

N-{5-[(6-O-Benzoyl-4',6'-O-propylidene-β-D-maltosyl)-oxy-methyl]-2-chloro-phenyl}-acetamide or a pharmaceutically acceptable salt thereof;

N-(5-{[4',6'-O-Benzylidene-6-O-(4-toluenesulfonyl)-β-D-maltosyl]-oxy-methyl}-2-chloro-phenyl)-acetamide or a pharmaceutically acceptable salt thereof;

N-(5-{[2,3,2',3'-Tetra-O-acetyl-4',6'-O-benzylidene-6-O-(4-toluenesulfonyl)-β-D-maltosyl]-oxy-methyl}-2-chloro-phenyl)-acetamide or a pharmaceutically acceptable salt thereof;

N-{5-[(6-O-Benzyl-4',6'-O-benzylidene-β-D-maltosyl)-oxy-methyl]-2-chloro-phenyl}-acetamide or a pharmaceutically acceptable salt thereof;

N-{5-[(6-O-Benzyl-4',6'-O-ethylidene-β-D-maltosyl)-oxy-methyl]-2-chloro-phenyl}-acetamide or a pharmaceutically acceptable salt thereof;

N-(2-Chloro-5-{[4',6'-O-(4-nitro)-benzylidene-β-D-maltosyl]-oxy-methyl}-phenyl)-acetamide or a pharmaceutically acceptable salt thereof;

N-(5-{[6-O-Benzoyl-4',6'-O-(4-nitro)-benzylidene-β-D-maltosyl]-oxy-methyl}-2-chloro-phenyl)-acetamide or a pharmaceutically acceptable salt thereof;

N-{2-Chloro-5-[(4',6'-O-(4-chloro)-benzylidene-β-D-maltosyl)-oxy-methyl]-phenyl}-acetamide or a pharmaceutically acceptable salt thereof;

N-{5-[(6-O-Benzoyl-4',6'-O-(4-chloro)-benzylidene-β-D-maltosyl)-oxy-methyl]-2-chloro-phenyl}-acetamide or a pharmaceutically acceptable salt thereof;

N-{2-Chloro-5-[(4',6'-O-isobutylidene-β-D-maltosyl)-oxy-methyl]-phenyl}-acetamide or a pharmaceutically acceptable salt thereof;

N-{5-[(6-O-Benzoyl-4',6'-O-isobutylidene-β-D-maltosyl)-oxy-methyl]-2-chloro-phenyl}-acetamide or a pharmaceutically acceptable salt thereof;

N-{5-[(4',6'-O-((1R)-2-Phenyl-ethylidene)-β-D-maltosyloxy)-methyl]-2-chloro-phenyl}-acetamide or a pharmaceutically acceptable salt thereof;

N-{5-[(6-O-Benzoyl-4',6'-O-((1R)-2-phenyl-ethylidene)-β-D-maltosyloxy)-methyl]-2-chloro-phenyl}-acetamide or a pharmaceutically acceptable salt thereof;

N-{2-Chloro-5-[(4',6'-O-((1R)-3-cyano-propylidene)-β-D-maltosyloxy)-methyl]-phenyl}-acetamide or a pharmaceutically acceptable salt thereof;

N-{5-{[6-O-Benzoyl-4',6'-O-((1R)-3-cyanopropylidene)-β-D-maltosyloxy]-methyl}-2-chloro-phenyl}-acetamide or a pharmaceutically acceptable salt thereof;

N-{2-Chloro-5-[(4',6'-O-((1R)-3-ethoxy-propylidene)-β-D-maltosyloxy)-methyl]-phenyl}-acetamide or a pharmaceutically acceptable salt thereof;

N-{5-{[6-O-Benzoyl-4',6'-O-((1R)-3-ethoxypropylidene)-β-D-maltosyloxy]-methyl}-2-chloro-phenyl)-acetamide or a pharmaceutically acceptable salt thereof;

N-(2-Chloro-5-{[4',6'-O-(4-pyridinemethylidene)-β-D-maltosyl]-oxy-methyl}-phenyl)-acetamide or a pharmaceutically acceptable salt thereof;

Benzoic acid 6-(3-acetylamino-4-chloro-benzoyloxy)-3-(7,8-dihydroxy-2-pyridin-4-yl-hexahydro-pyrano[3,2-d][1,3]dioxin-6-yloxy)-4,5-dihydroxy-tetrahydro-pyran-2-ylmethyl ester or a pharmaceutically acceptable salt thereof;

N-{5-[(4',6'-O-Benzylidene-β-D-maltosyloxy)-methyl]-2-chloro-phenyl}-acetamide or a pharmaceutically acceptable salt thereof;

N-{5-[(4',6'-O-Benzylidene-2,2',3,3', 6-penta-O-acetyl-β-D-maltosyl-oxy)-methyl]2-chloro-phenyl}-acetamide or a pharmaceutically acceptable salt thereof;

N-{5-[(6-O-Benzoyl-4',6'-O-benzylidene-β-D-maltosyl-oxy)-methyl]-2-chloro-phenyl}-acetamide or a pharmaceutically acceptable salt thereof;

(R)-N-[2-Chloro-5-[[[2,3-di-O-acetyl-6-O-benzoyl-4-O-[2,3-di-O-acetyl-4,6-O-(phenylmethylene)-α-D-glucopyranoysl]-β-glucopyranosyl]-oxy]methyl]-phenyl]acetamide or a pharmaceutically acceptable salt thereof;

(R)-N-[2-Chloro-5-[[[6-O-(5-methoxy-1,5-dioxopentyl)-4-O-[4,6-O-(phenylmethylene)-α-D-glucopyranoysl]-β-D-glucopyranosyl]oxy]methyl]-phenyl]acetamide or a pharmaceutically acceptable salt thereof;

4-Chloro-3-nitro-benzyl-4',6'-O-benzylidene-β-D-maltoside or a pharmaceutically acceptable salt thereof;

4-Chloro-3-nitro-benzyl-6-O-benzoyl-4',6'-O-benzylidene-β-D-maltoside or a pharmaceutically acceptable salt thereof;

(R)-(4-Chloro-3-nitrophenyl)methyl-2,3-di-O-acetyl-6-O-benzoyl-4-O-[2,3-di-O-acetyl-4,6-O-(phenylmethylene)-α-D-glucopyranosyl]-β-D-glucopyranoside or a pharmaceutically acceptable salt thereof;

Nicotinic acid 6-(4-chloro-3-nitro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester or a pharmaceutically acceptable salt thereof;

(R)-(4-Chloro-3-nitrophenyl)methyl 4-[2,3-di-O-acetyl-4,6-O-(phenylmethylene)-α-D-glucopyranosyl]-β-D-glucopyranoside 2,3-diacetate 6-(3-pyridinecarboxylate) or a pharmaceutically acceptable salt thereof;

4-Methoxy-benzoic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester or a pharmaceutically acceptable salt thereof;

4-Methoxy-benzoic acid 4,5-diacetoxy-6-(3-acetylamino-4-chloro-benzyloxy)-3-(7,8-diacetoxy-2-phenyl-hexahydro-pyrano[3,2-d][1,3]dioxin-6-yloxy)-tetrahydro-pyran-2-ylmethyl ester or a pharmaceutically acceptable salt thereof;

4-Chloro-benzoic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester or a pharmaceutically acceptable salt thereof;

4-Chloro-benzoic acid 4,5-diacetoxy-6-(3-acetylamino-4-chloro-benzyloxy)-3-(7,8-diacetoxy-2-phenyl-hexahydro-pyrano[3,2-d][1,3]dioxin-6-yloxy)-tetrahydro-pyran-2-ylmethyl ester or a pharmaceutically acceptable salt thereof;

(R)-N-[2-Chloro-5-[[[6-O-(4-chloro-3-nitrobenzoyl)-4-O-[4,6O-(phenylmethylene)-α-D-glucopyranosyl]-β-D-glucopyranosyl]oxy]methyl]phenyl]acetamide or a pharmaceutically acceptable salt thereof;

N-{5-[(2,2',3,-Tri-O-Acetyl-6-O-(4-chloro-3-nitrobenzoyl)-4',6'-O-(benzylidene)-β-D-maltosyl)-oxymethyl]-2-chloro-phenyl)-acetamide or a pharmaceutically acceptable salt thereof;

(R)-N-[2-Chloro-5-[[[6-O-(4-cyanobenzoyl)-4-O-[4,6O-(phenylmethylene)-α-D-glucopyranosyl]-β-D-glucopyranosyl]oxy]methyl]phenyl]acetamide or a pharmaceutically acceptable salt thereof;

(R)-N-[2-Chloro-5-[[[6-O-(4-nitrobenzoyl)-4-O-[4,6O-(phenylmethylene)-α-D-glucopyranosyl]-β-D-glucopyranosyl]oxy]methyl]phenyl]acetamide or a pharmaceutically acceptable salt thereof;

(R)-N-[2-Chloro-5-[[[6-O-(3-trifluoromethylbenzoyl)-4-O-[4,6O-(phenylmethylene)-α-D-glucopyranosyl]-β-D-glucopyranosyl]oxy]-methyl]phenyl]acetamide or a pharmaceutically acceptable salt thereof;

N-{5-[(4',6'-O-Benzylidene-6-O-(2-iodo)-benzoyl-β-D-maltosyl)-oxy-methyl]-2-chloro-phenyl)-acetamide or a pharmaceutically acceptable salt thereof;

N-{5-[(4',6'-O-Benzylidene-6-O-(3-iodo)-benzoyl-β-D-maltosyl)-oxy-methyl]-2-chloro-phenyl}-acetamide or a pharmaceutically acceptable salt thereof;

N-{5-[(4',6'-O-Benzylidene-6-(4-iodo-benzoyl)-oxy-β-D-maltosyl)-oxy-methyl]-2-chloro-phenyl}-acetamide or a pharmaceutically acceptable salt thereof;

(R)-N-[-2-Chloro-5-[[[6-O-(phenylacetyl)-4-O-[4,6-O-(phenylmethylene)-β-D-glucopyranosyl]-β-D-glucopyranosyl]oxy]methyl]phenyl]acetamide or a pharmaceutically acceptable salt thereof;

(R)-N-[2-Chloro-5-[[[2,3-di-O-acetyl-4-O-[2,3-di-O-acetyl-4,6-O-(phenyl-methylene)-α-D-glucopyranosyl]-6-O-(phenylacetyl)-β-D-glucopyranosyl]-oxy]methyl]phenyl]acetamide or a pharmaceutically acceptable salt thereof;

N-{5-[(4',6'-O-Benzylidene-6-O-phenyl-ethyl-carboxyl-β-D-maltosyl)-oxy-methyl]-2-chloro-phenyl}-acetamide or a pharmaceutically acceptable salt thereof;

N-{5-[(4',6'-O-Benzylidene-6-O-phenyl-propyl-carboxyl-β-D-maltosyl)-oxy-methyl]-2-chloro-phenyl}-acetamide or a pharmaceutically acceptable salt thereof;

Diphenyl-acetic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester or a pharmaceutically acceptable salt thereof;

Diphenyl-acetic acid 4,5-diacetoxy-6-(3-acetylamino-4-chloro-benzyloxy)-3-(7,8-diacetoxy-2-phenyl-hexahydro-pyrano[3,2-d][1,3]dioxin-6-yloxy)-tetrahydro-pyran-2-ylmethyl ester or a pharmaceutically acceptable salt thereof;

(3,4-Dimethoxy-phenyl)-acetic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester or a pharmaceutically acceptable salt thereof;

(3,4-Dimethoxy-phenyl)-acetic acid 4,5-diacetoxy-6-(3-acetylamino-4-chloro-benzyloxy)-3-(7,8-diacetoxy-2-phenyl-hexahydro-pyrano[3,2-d][1,3]dioxin-6-yloxy)-tetrahydro-pyran-2-ylmethyl ester or a pharmaceutically acceptable salt thereof;

Nicotinic acid 6-(3-acetylamino-4-chloro-benzyloxy)-3-(7,8-dihydroxy-2-phenyl-hexahydro-pyrano[3,2-d][1,3]

dioxin-6-yloxy)-4,5-dihydroxy-tetrahydro-pyran-2-ylmethyl ester or a pharmaceutically acceptable salt thereof;

Nicotinic acid 4,5-diacetoxy-6-(3-acetylamino-4-chloro-benzyloxy)-3-(7,8-diacetoxy-2-phenyl-hexahydro-pyrano[3,2-d][1,3]dioxin-6-yloxy)-tetrahydro-pyran-2-ylmethyl ester or a pharmaceutically acceptable salt thereof;

(R)-N-[5-[[[6-O-(4-Benzoylbenzoyl)-4-O-[4,6-O-(phenylmethylene)-α-D-glucopyranosyl]-β-D-glucopyranosyl]oxy]methyl]-2-chlorophenyl]acetamide or a pharmaceutically acceptable salt thereof;

N-{5-[(4',6'-O-Benzylidene-β-maltosyl)-oxy-methyl]-2-methyl-phenyl}-acetamide or a pharmaceutically acceptable salt thereof;

N-Acetyl-{5-[(2,2',3,3',6-penta-O-acetyl-4',6'-O-benzylidene-β-D-maltosyl)-oxy-methyl]-2-methyl-phenyl}acetamide or a pharmaceutically acceptable salt thereof;

N-(5-{[4',6'-O-Benzylidene-6-O-(4-toluenesulfonyl)-β-D-maltosyl]-oxy-methyl}-2-methyl-phenyl)-acetamide or a pharmaceutically acceptable salt thereof;

N-{5-[(4',6'-Benzylidene-6-O-phenyl-β-D-maltosyl)-oxy-methyl]-2-chloro-phenyl}-acetamide or a pharmaceutically acceptable salt thereof;

(R)-N-[2-Chloro-5-[[[4-O-[4',6'-O-(phenylmethylene)-α-D-glucopyranosyl]-β-D-glucopyranosyl]oxy]methyl] phenyl]-3-pyridinecarboxamide or a pharmaceutically acceptable salt thereof;

(R)-N-[5-[[[6-O-Benzoyl-4-O-[4',6'-O-(phenylmethylene)-α-D-glucopyranosyl]-β-D-glucopyranosyl]oxy]methyl]-2-chlorophenyl]-3-pyridinecarboxamide or a pharmaceutically acceptable salt thereof;

Furan-2-carboxylic acid {5-[(4',6'-O-benzylidene-β-D-maltosyl)-oxy-methyl]-2-chloro-phenyl}-amide or a pharmaceutically acceptable salt thereof;

Furan-2-carboxylic acid {5-[(6-O-benzoyl-4',6'-O-benzylidene-β-D-maltosyl)-oxy-methyl]-2-chloro-phenyl}-amide or a pharmaceutically acceptable salt thereof;

N-{2-Chloro-5-[(4',6'-O-benzylidene-β-D-maltosyl)-oxy-methyl]-phenyl}-pent-4-enamide or a pharmaceutically acceptable salt thereof;

N-{2-Chloro-5-[(6-O-benzoyl-4',6'-O-benzilidene-β-D-maltosyl)-oxy-methyl]-phenyl}-pent-4-enamide or a pharmaceutically acceptable salt thereof;

5-(6-O-Benzoyl-4',6'-O-benzylidene-β-D-maltosyl)-oxy-methyl-2-chloro-phenylamine or a pharmaceutically acceptable salt thereof;

(4-Chloro)-benzyl-4',6'-O-benzylidene-β-D-maltoside or a pharmaceutically acceptable salt thereof;

Benzoic acid 1-O-(4-chloro)-benzyl-4',6'-O-benzylidene-6-deoxy-β-D-malto-6-yl ester or a pharmaceutically acceptable salt thereof;

4-Benzoyl-N-{5-[(4',6'-O-benzylidene-β-D-maltosyl)-oxy-methyl]-2-chloro-phenyl}-benzamide or a pharmaceutically acceptable salt thereof;

4-Benzoyl-N-{5-[(6-benzoyl-oxy-4',6'-O-benzylidene-β-D-maltosyl)-oxy-methyl]-2-chloro-phenyl}-benzoic acid amide or a pharmaceutically acceptable salt thereof;

4-Benzoyl-N-{5-[(4',6'-O-benzylidene-6-O-(2-iodo)-benzoyl-β-D-maltosyl)-oxy-methyl]-2-chloro-phenyl}-benzamide or a pharmaceutically acceptable salt thereof;

4-Benzoyl-N-{5-[(4',6'-O-benzylidene-6-O-(3-iodo-benzoyl)-β-D-maltosyl)-oxy-methyl]-2-chloro-phenyl}-benzamide or a pharmaceutically acceptable salt thereof;

4-Benzoyl-N-{5-[(4',6'-O-benzylidene-6-(4-iodo-benzoyl)-oxy-β-D-maltosyl)-oxy-methyl]-2-chloro-phenyl}-benzoic acid amide or a pharmaceutically acceptable salt thereof;

(1-{5-[(4',6'-O-Benzylidene-β-D-maltosyl)-oxy-methyl]-2-chloro-phenyl-carbamoyl}ethyl)-carbamic acid 9H-fluoren-9ylmethyl ester or a pharmaceutically acceptable salt thereof;

N-(9H-Fluoren-9ylmethoxycarbonyl)-N'-{5-[(6-O-benzoyl-4',6'-O-benzylidene-β-D-maltosyl)-oxy-methyl]-2-chloro-phenyl}-L-alaninamide or a pharmaceutically acceptable salt thereof;

N'-{5-[(6-O-benzoyl-4',6'-O-benzylidene-β-D-maltosyl)-oxy-methyl]-2-chloro-phenyl}-L-alaninamide or a pharmaceutically acceptable salt thereof;

N-{5-[(4',6'-O-Benzylidene-β-D-maltosyl)-oxymethyl]-2-chloro-phenyl}-N-methyl-acetamide or a pharmaceutically acceptable salt thereof;

N-{5-[(6-O-Benzoyl-4',6'-O-benzylidene-β-D-maltosyl)-oxymethyl]-2-chloro-phenyl}-N-methyl-acetamide or a pharmaceutically acceptable salt thereof;

N-{5-[(4',6'-O-Benzylidene-β-D-maltosyl)-oxy-methyl]-2-chloro-phenyl}-carbamic acid methyl ester or a pharmaceutically acceptable salt thereof;

N-{5-[(6-O-Benzoyl-4',6'-O-benzylidene-β-D-maltosyl)-oxy-methyl]-2-chloro-phenyl}-carbamic acid methyl ester or a pharmaceutically acceptable salt thereof;

N-{5-[(6-O-(3-Benzyl-1-oxo-propyl)-4',6'-O-benzylidene-β-D-maltosyl)-oxy-methyl]-2-chloro-phenyl}-carbamic acid methyl ester or a pharmaceutically acceptable salt thereof;

N-{5-[(4',6'-O-Benzylidene-β-D-maltosyl)-oxy-methyl]-2-chloro-phenyl}-methanesulfonamide or a pharmaceutically acceptable salt thereof;

N-{5-[(6-O-Benzoyl-4',6'-O-benzylidene-β-D-maltosyl)-oxy-methyl]-2-cyano-phenyl}-acetamide or a pharmaceutically acceptable salt thereof;

N-{5-[(6-O-Benzoyl-4',6'-O-benzylidene-β-D-maltosyl)-oxy-methyl]-2-methyl-phenyl}-acetamide or a pharmaceutically acceptable salt thereof;

6-[-6-(4-Chloro-3-nitro-benzylsulfanyl)-4,5-dihydroxy-2-hydroxymethyl-tetrahydro-pyran-3-yloxy]-2-phenyl-hexahydro-pyrano[3,2-d][1,3]dioxine-7,8-diol or a pharmaceutically acceptable salt thereof;

(4-Chloro-3-nitro-benzyl) 6-O-benzoyl-4',6'-O-benzoyl-4',6',-O-benzylidene-1-thio-β-D-maltoside or a pharmaceutically acceptable salt thereof.

The compounds of this invention were be prepared according to the following schemes from commercially available starting materials or starting materials which can be prepared using literature procedures. This scheme shows the preparation of representative compounds of this invention.

Acetobromomaltose 1 is coupled with a benzyl alcohol 2 in the presence of a catalyst such as a mercuric bromide, mercuric cyanide, silver triflate, or silver perchlorate in an aprotic solvent such as acetonitrile, dichloromethane, ether, toluene or nitromethane at temperatures ranging from −40° C. to reflux to yield glycoside 3 (Scheme 1). This glycosidation can also be accomplished using Schmidt's trichloro-acetimidate coupling with zinc bromide in a solvent such as dichloromethane. Reduction of the nitro group of 3 can be accomplished with a reducing agent such as stannous chloride in a polar aprotic solvent such as ethyl acetate at ambient temperature to reflux to afford an anilino compound 4. Coupling of 4 with an acid chloride can be completed in the presence of an amine base such as triethylamine or diisopropylethylamine or using a stronger base such as sodium hydride (for sterically hindered systems) in an aprotic solvent such as dichloromethane or tetrahydrofuran at temperatures ranging from 0° C. to ambient temperature to yield the target compound 5. The peracetylated compound 5 can be converted to the heptahydroxy compound 6 with catalytic sodium methoxide in methanol or aqueous sodium hydroxide in methanol at temperatures ranging from ambient temperature to reflux.

As illustrated in Scheme 2, an acetal (7) was formed at the C-4',6' positions of the disaccharide of heptahydroxy compound 6 using an appropriate aldehyde dimethyl or diethyl acetal and an acid source such as p-toluenesulfonic acid monohydrate or camphorsulfonic acid in a polar solvent such as N,N-dimethylformamide at 60° C. In difficult cases, an aldehyde and sulfuric acid can be used in DMF at higher temperatures to obtain the product acetal. At this point, the 6-position primary alcohol was selectively acylated using an acid chloride in a 1:1 mixture of tetrahydrofuran and the hindered base 2,4,6-collidine at −40° C. initially to ambient temperature overnight to generate compound 8. The remaining four secondary alcohols of the disaccharide can then be protected with acetic anhydride and triethylamine in a solvent such as dichloromethane to afford the peracetylated compound 9.

On the other hand, acetal 7 can first be converted to a tosylate using tosyl chloride and pyridine in a solvent such as dichloromethane (Scheme 3); the resulting intermediate is then peracetylated as mentioned above to generate compound 10. Through overall displacement of the 6-position tosylate (alcohol formation with sodium formate followed by ether formation with benzyl 2,2,2-trichloroacetimidate), an ether linkage is incorporated at this site on the molecule. The benzylidene acetal is then removed under strongly acidic conditions such as 1M ethereal HCl to afford compound 11. A new acetal is then formed at the C-4',6' positions using the conditions mentioned previously or just an aldehyde and the acid source in benzene at elevated temperature (60° C.). Finally, the four secondary acetates are removed with catalytic sodium methoxide in methanol or aqueous sodium hydroxide in methanol at temperatures ranging from ambient temperature to reflux to obtain the hydroxy compound 12.

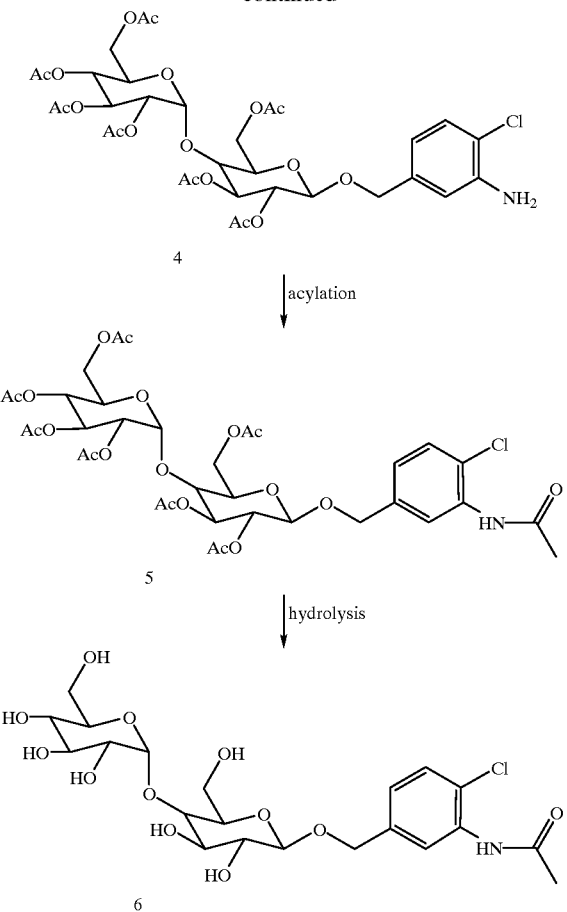

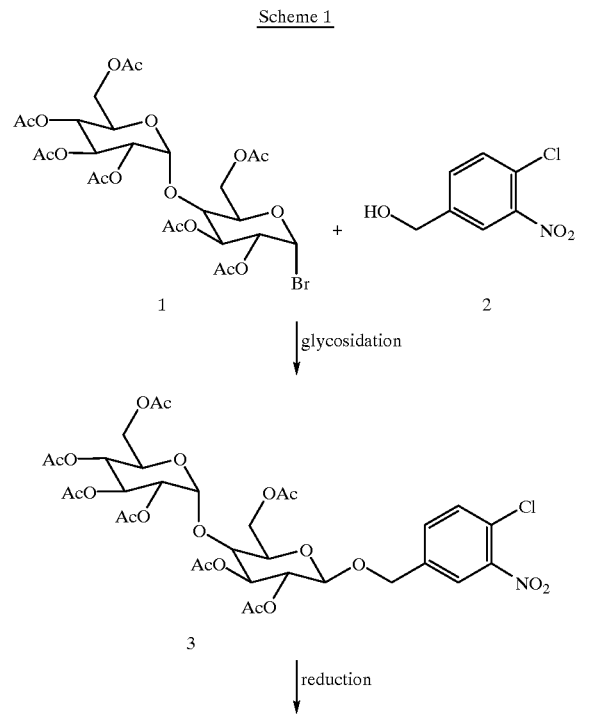

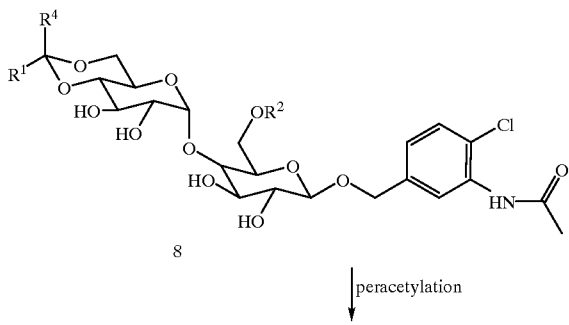

8

↓ peracetylation

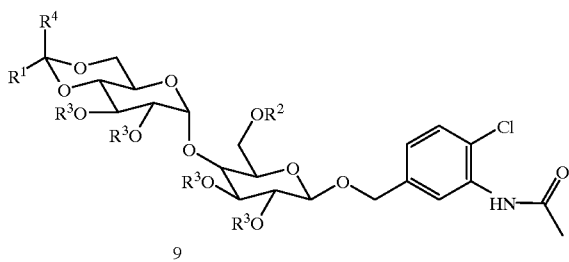

9

If R₂=Bn, then:

Scheme 3

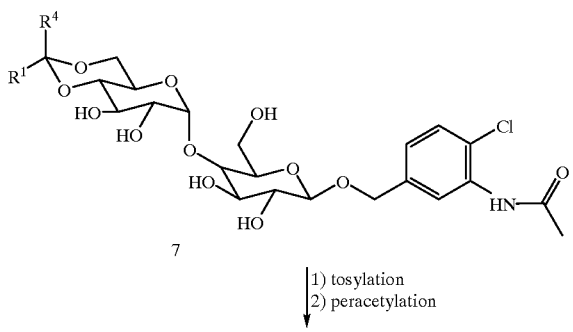

7

1) tosylation
2) peracetylation

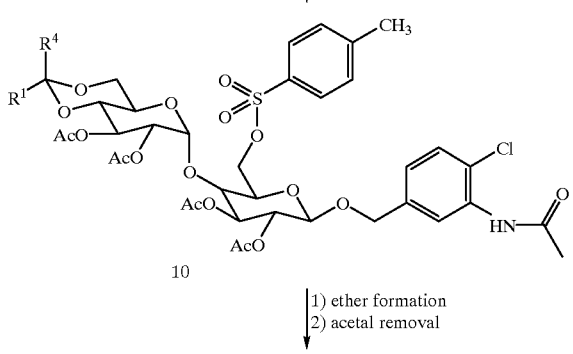

10

1) ether formation
2) acetal removal

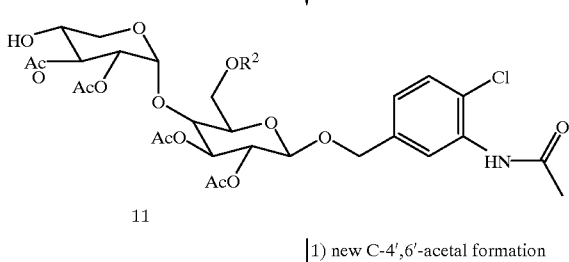

11

1) new C-4',6'-acetal formation
2) hydrolysis

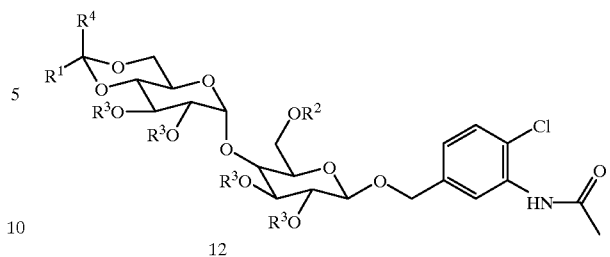

12

The compounds of this invention are useful as antiproliferative agents. The following procedures show the evaluation of representative compounds of this invention in standard pharmacological test procedure which measured ability of the evaluated compound to inhibit smooth muscle cell proliferation.

Effects of Compounds on Cell Proliferation Using $^3$H Thymidine Incorporation

Human and porcine smooth muscle cells were tested in early passage (generally passage 3–7) at sub-confluent conditions. Cultures were grown in 16 mm (24 well) multi-well culture dishes in medium 199 supplemented with 10% fetal bovine serum and 2% antibiotic/antimycotic. At sub-confluence, the cells were placed in a defined serum free medium (AIM-V; Gibco) for 24–48 h prior to initiating the experimental protocol.

Although compounds were found to be more effective with longer pre-incubations, in general, the procedures were initiated with the addition of compound, $^3$H thymidine and serum/growth factor to serum deprived synchronized cells and results are reported accordingly.

Compounds were added to each well at 50 fold dilution (20 µL/well) and the plates were incubated for 24–36 h at 37° C. in 5% $CO_2$. Compounds were initially dissolved in 50% ethanol and serially diluted into media. Compounds were routinely evaluated at concentrations from 1 to 100 µM. As a control, grade II porcine intestinal mucosal heparin (sodium salt) was routinely evaluated in all cell preparations at concentrations from 0.1 to 100 µg/mL.

At the completion of the test procedure, plates were placed on ice, washed three times with ice cold phosphate buffered saline (PBS) and incubated in ice cold 10% trichloroacetic acid (TCA) got 30 min to remove acid soluble proteins. Solution was transferred to scintillation vials containing 0.4 N HCl (500 µL/vial to neutralize NaOH) and each well was rinsed two times with water (500 µL) for a total volume of 2 mL/vial.

Data was obtained, in triplicate, for both control and experimental samples. Control (100%) data was obtained from maximally stimulated cells, as the result of growth factor or serum stimulation. Experimental data was obtained from cells maximally stimulated with growth factor or serum and treated with compound. Data are expressed as an $IC_{50}$ or percent inhibition in Table I below.

TABLE 1

| Compound of Example | Porcine Smooth Muscle Cell Antiproliferation IC50 |
| --- | --- |
| 1 | 32% @ 100 µM |
| 2 | 0.103 µM |
| 3 | 2.92 µM |
| 4 | 16% @ 50 µM |
| 5 | 0.037 µM |

TABLE 1-continued

| Compound of Example | Porcine Smooth Muscle Cell Antiproliferation IC50 |
|---|---|
| 6 | 0.133 µM |
| 7 | 0.088 µM |
| 8 | 0.001 µM |
| 9 | 0.083 µM |
| 10 | 19.2 µM |
| 11 | 0.003 µM |
| 12 | 29.4 µM |
| 13 | 0.023 µM |
| 15 | 0.003 µM |
| 16 | 16.3 µM |
| 17 | 0.035 µM |
| 18 | 43% @ 50 µM |
| 19 | 0.001 µM |
| 20 | 48% @ 50 µM |
| 21 | 0.062 µM |
| 22 | 5.53 µM |
| 23 | 0.003 µM |
| 24 | 6.60 µM |
| 25 | 0.700 µM |
| 26 | 0.010–0.030 µM |
| 27 | 0.070 µM |
| 28 | 0.400 µM |
| 29 | 44.1 µM |
| 30 | 0.351 µM |
| 31 | 0.380 µM |
| 32 | 0.405 µM |
| 33 | 0.312 µM |
| 34 | 0.061 µM |
| 35 | 0.851 µM |
| 36 | 0.089 µM |
| 37 | 0.588 µM |
| 38 | 0.187 µM |
| 39 | 2.53 µM |
| 40 | 0.092 µM |
| 41 | 0.273 µM |
| 42 | 0.027 µM |
| 43 | 0.008 µM |
| 44 | 0.062 µM |
| 45 | 6.44 µM |
| 46 | 0.032 µM |
| 47 | 0.078 µM |
| 48 | 0.007 µM |
| 49 | 0.104 µM |
| 50 | 0.084 µM |
| 51 | 0.354 µM |
| 52 | 0.048 µM |
| 53 | 0.266 µM |
| 54 | 0.211 µM |
| 55 | 0.304 µM |
| 56 | 0.530 µM |
| 57 | 8.90 µM |
| 58 | 0.600 µM |
| 59 | 0.490 µM |
| 60 | 0.038 µM |
| 61 | 13.7 µM |
| 62 | 0.023 µM |
| 63 | 7.73 µM |
| 64 | 0.050 µM |
| 65 | 17.8 µM |
| 66 | 0.180 µM |
| 67 | 1.29 µM |
| 68 | 25.3 µM |
| 69 | 1.53 µM |
| 70 | 9.94 µM |
| 71 | 0.050 µM |
| 72 | 0.016 µM |
| 73 | 0.132 µM |
| 74 | 1.22 µM |
| 75 | 4.69 µM |
| 76 | 0.156 µM |
| 77 | 0.081 µM |
| 78 | 8% @ 50 µM |
| 79 | 2.36 µM |
| 80 | 7.57 µM |
| 81 | 0.014 µM |
| 82 | 0.352 µM |
| 83 | 18% @ 50 µM |
| 84 | 0.250 µM |
| 85 | 0.418 µM |
| 86 | 16.3 µM |
| 87 | 0.031 µM |

The compounds of this invention are useful in treating or inhibiting diseases which are characterized by excessive smooth muscle cell proliferation (smooth muscle cell hyperproliferation). The compounds are particularly useful in treating hyperproliferative vascular diseases which are characterized by smooth muscle cell hyperproliferation, such as restenosis, which most frequently arises from vascular reconstructive surgery and transplantation, for example, balloon angioplasty, vascular graft surgery, coronary artery bypass surgery, and heart transplantation. Other disease states in which there is unwanted "cellular" vascular proliferation include hypertension, asthma, and congestive heart failure. The compounds of this invention are also useful as inhibitors of angiogenesis. Angiogenesis (neovascularization), the process by which new capillaries are formed, is of principal importance for a number of pathological events including chronic inflammation and malignant processes. The compounds of this invention are therefore useful as antineoplastic agents.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.1 to 10 mg/kg administered parenterally (intravenous preferred), with projected daily oral dosage being approximately ten-fold higher. Anticipated intravenous administration would last for approximately 5–30 days following acute vascular injury (i.e., balloon angioplasty or transplantation) and for a longer duration for the treatment of chronic disorders. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packaged powders, vials, ampoules, pre filled syringes or sachets containing liquids. The unit dosage form can be, for example, a capsule or tablet itself, or it can be the appropriate number of any such compositions in package form.

The following provides the preparation of representative compounds of this invention.

EXAMPLE 1

N-{2-Chloro-5-[(4',6'-O-ethylidene)-β-D-maltosyloxymethyl]-phenyl}-acetamide

Step 1

4-Chloro-3-nitro-benzyl-β-D-maltoside heptaacetate

To a stirred solution of 4-chloro-3-nitrobenzyl alcohol (6.70 g, 35.7 mmol) and $HgBr_2$ (14.2 g, 39.3 mmol) in freshly distilled $CH_3CN$ (239 mL) was added in one portion $Hg(CN)_2$ (9.02 g, 35.7 mmol). After 0.5 h, acetobromomaltose (25.0 g, 35.7 mmol) was added, and the mixture stirred for 18 h at rt. The reaction was then quenched with a mixture of $H_2O$:brine (1:1, 100 mL) and extracted with 10% $CH_2Cl_2$:EtOAc. The combined organic extracts were dried ($MgSO_4$) and concentrated. Purification by flash chromatography (10:90 to 80:20 EtOAc:petroleum ether gradient) gave 51.9 g (90%) of the title compound as a glassy oil which was recrystallized from $Et_2O$:petroleum ether to afford a glassy white solid, mp 107–111° C.; $^1H$ NMR ($CDCl_3$) δ2.00 (s, 3H), 2.02 (s, 3H), 2.03, (s, 3H), 2.04 (s, 6H), 2.11 (s, 3H), 2.15 (s, 3H), 3.70 (ddd, J=2.9, 4.2, 9.7 Hz, 1H), 3.94–3.98 (m, 1H), 4.01–4.07 (m, 2H), 4.20–4.28 (m, 2H), 4.54 (dd, J=2.9, 12.3 Hz, 1H), 4.63–4.68 (m, 2H), 4.84–4.94 (m, 3H), 5.06 (t, J=10.1 Hz, 1H), 5.26 (t, J=9.2 Hz, 1H), 5.36 (dd, J=9.7, 10.3 Hz, 1H), 5.42 (d, J=4.2 Hz, 1H), 7.43 (dd, J=2.2, 8.3 Hz, 1H), 7.53 (d, J=8.3 Hz, 1H), 7.83 (d, J=2.0 Hz, 1H); IR (KBr) 3450, 2950, 1755, 1550, 1375, 1230 and 1050 $cm^{-1}$; mass spectrum [(+) ESI], m/z 823/825 $(M+NH_4^+)$, 828/830 $(M+Na)^+$; Anal. Calcd. for $C_{33}H_{40}ClNO_{20}$: C, 49.17; H, 5.00; N, 1.74, Found: C, 49.16; H, 4.88; N, 1.71.

Step 2

2-Chloro-5-(hepta-O-acetyl-β-D-maltosyl-oxymethyl)-phenylamine

A solution containing 4-chloro-3-nitro-benzyl-β-D-maltoside heptaacetate (19.3 g, 23.9 mmol) and tin (II) chloride dihydrate (37.7 g, 167 mmol) in EtOAc (479 mL) was refluxed for 2 h. The reaction was cooled to rt, carefully quenched with sat. aq. $NaHCO_3$ (until basic), diluted with EtOAc (250 mL), stirred for 0.5 h and filtered. The biphasic filtrate was separated and the aqueous phase extracted with EtOAc. The combined organic extracts were dried ($Na_2SO_4$) and concentrated. Purification by flash chromatography (0 to 12% acetone/$CHCl_3$ gradient) gave 17.8 g (96%) 2-Chloro-5-(hepta-O-acetyl-β-D-maltosyl-oxymethyl)-phenylamine as a glassy solid, mp 78–79° C.; $^1H$ NMR ($CDCl_3$) δ2.00 (s, 9H), 2.026 (s, 3H), 2.032 (s, 3H), 2.11 (s, 3H), 2.16 (s 3H), 3.00–5.00 (bs, 2H), 3.64–3.68 (m, 1H), 3.97 (ddd, J=2.4, 4.2, 10.1 Hz, 1H), 4.02–4.07 (m, 2H), 4.24 (dd, J=2.2, 3.7, 1H), 4.27 (dd, J=2.6, 4.0 Hz, 1H), 4.50–4.57 (m, 3H), 4.74 (d, J=12.1 Hz, 1H), 4.83–4.90 (m, 2H), 5.05 (t, J=10.1 Hz, 1H), 5.22 (t, J=9.2 Hz, 1H), 5.35 (dd, J=9.7, 10.5 Hz, 1H), 5.42 (d, J=4.0 Hz, 1), 6.62 (dd, J=2.0, 8.1 Hz, 1H), 6.76 (d, J=2.0 Hz, 1H), 7.21 (d, J=8.1 Hz, 1H); IR (KBr) 3450, 3350, 2950, 1755, 1650, 1425, 1375, 1230 and 1050 $cm^{-1}$; mass spectrum [(+) ESI], m/z 776/778 $(M+H)^+$, 798/800 $(M+Na)^+$; Anal. Calcd. for $C_{33}H_{42}ClNO_{18}$: C, 51.07; H, 5.45; N, 1.80, Found: C, 50.94; H, 5.52; N, 1.60.

Step 3

N-[2-Chloro-5-(hepta-O-acetyl-β-D-maltosyl-oxymethyl)-phenyl]-acetamide

To a stirred solution of 2-chloro-5-(hepta-O-acetyl-β-D-maltosyl-oxymethyl)-phenylamine (20.6 g, 26.5 mmol) and triethylamine (8.13 mL, 58.3 mmol) in THF (265 mL) at 0° C. was added dropwise acetyl chloride (2.26 mL, 31.8 mmol). After 0.5 h at this temperature, it was warmed to rt and stirred an additional 6 h. At this point, the reaction was concentrated and taken up in EtOAc (700 mL). This organic solution was washed with 1 N HCl (70 mL), sat. aq. NaHCO$_3$ (70 mL), and brine (70 mL) and then dried (MgSO$_4$). After concentration, the residue was purified by flash chromatography (20:80 to 100:0 EtOAc:petroleum ether gradient) to afford the product (16.2 g, 75%) as a glassy solid, mp 84–86° C.; $^1$H NMR (CDCl$_3$) δ2.00 (s, 6H), 2.020 (s, 3H), 2.027 (s, 3H), 2.03 (s, 3H), 2.11 (s, 3H), 2.16 (s, 3H), 2.24 (s, 3H), 3.66–3.69 (m, 1H), 3.94–3.98 (m, 1H), 4.00–4.06 (m, 2H), 4.22–4.28 (m, 2H), 4.50–4.61 (m, 3H), 4.80–4.91 (m, 3H), 5.05 (t, J=10.1 Hz, 1H), 5.22 (t, J=9.2 Hz, 1H), 5.35 (dd, J=9.4, 10.5 Hz, 1H), 5.41 (d, J=4.0 Hz, 1H), 6.99 (dd, J=2.0, 8.1 Hz, 1H), 7.34 (d, J=8.1 Hz, 1H), 7.62 (s, 1H), 8.32 (s, 1H); IR (KBr) 3400, 2950, 1750, 1690, 1600, 1540, 1425, 1375, 1230 and 1050 cm$^{-1}$; mass spectrum [(+) ESI], m/z 818/820 (M+H)$^+$, 840 (M+Na)$^+$; Anal. Calcd. for C$_{35}$H$_{44}$ClNO$_{19}$: C, 51.38; H, 5.42; N, 1.71, Found: C, 51.03; H, 5.36; N, 1.59.

Step 4

N-[2-Chloro-5-(β-D-maltosyl-oxymethyl)-phenyl]-acetamide

A solution containing N-[2-chloro-5-(hepta-O-acetyl-β-D-maltosyl-oxymethyl)-phenyl]-acetamide (0.945 g, 1.12 mmol) and 25 weight % NaOMe in MeOH (19.2 µL, 0.336 mmol) in MeOH (27.6 ml) was refluxed for 2.5 h. The reaction was cooled to room temperature and concentrated, and the resulting residue was triturated with Et$_2$O to afford the product (0.583 g, 99%) as a foam; $^1$H NMR (DMSO-d$_6$) δ2.07 (s, 3H), 3.03–3.16 (m 2H), 3.19–3.49 (m, 7H), 3.55–3.62 (m, 2H), 3.67–3.73 (m, 1H), 4.28 (d, J=7.7 Hz, 1H), 4.33–5.76 (bs, 7H), 4.67 (ABq, J=12.5 Hz, Δδ=0.22, 2H), 5.01 (d, J=3.7 Hz, 1H), 7.21 (dd, J=1.8, 8.1 Hz, 1H), 7.44 (d, J=8.1 Hz, 1H), 7.64 (d, J=1.5 Hz, 1H), 9.33–9.69 (bs, 1H); IR (KBr) 3400, 2900, 1680, 1600, 1540, 1430, 1375, 1310, 1150 and 1035 cm$^{-1}$, mass spectrum [(+) ESI], m/z 524/526 (M+H)$^+$, 546 (M+Na)$^+$; Anal. Calcd. for C$_{21}$H$_{30}$ClNO$_{12}$.1.0 MeOH: C, 47.53; H, 6.16; N, 2.52. Found: C, 47.94; H, 6.34; N, 2.42.

Step 5

N-{2-Chloro-5-[(4',6'-O-ethylidene)-β-D-maltosyloxymethyl]-phenyl}-acetamide

To a stirred solution of N-[2-chloro-5-(β-D-maltosyl-oxymethyl)-phenyl]-acetamide (0.500 g, 0.954 mmol) in DMF (12.5 mL) at rt was added acetaldehyde dimethyl acetal (0.202 mL, 1.91 mmol) dropwise followed by TsOH.H$_2$O (0.0907 g, 0.477 mmol). The reaction mixture was heated to 60° C. for 6 h and then quenched with K$_2$CO$_3$ (0.0659 g, 0.477 mmol) with an additional 0.5 h heating at this temperature. At this point, the solution was filtered hot, and the solvent was distilled off using the high vac. The residue was purified by flash chromatography (80:2:1 EtOAc:EtOH:H$_2$O) to afford the product (0.323 g, 62%) as an off-white powder, mp 144–146° C.; $^1$H NMR (DMSO-d$_6$) δ1.22 (d, J=5.1 Hz, 3H), 2.07 (s, 3H), 3.05–3.11 (m, 1H), 3.11 (t, J=9.4 Hz, 1H), 3.25–3.37 (m, 3), 3.39–3.58 (m, 5H), 3.65–3.71 (m, 1H), 3.92 (dd, J=4.8, 9.9 Hz, 1H), 4.28 (d, J=7.7 Hz, 1H), 4.65 (t, J=5.7 Hz, 1H), 4.67 (ABq, J=12.3 Hz, Δδ=0.22, 2H), 4.69 (dd, J=4.8, 9.9 Hz, 1H), 5.09 (d, J=4.0 Hz, 1H), 5.23 (t, J=5.7 Hz, 2H), 5.47 (d, J=3.5 Hz, 1H), 5.57 (d, J=6.6 Hz, 1H), 7.22 (dd, J=1.8, 8.3 Hz, 1H), 7.44 (d, J=8.3 Hz, 1H), 7.65 (s, 1H), 9.52 (s, 1H); IR (KBr) 3400, 2910, 2880, 1675, 1600, 1535, 1450, 1420, 1375, 1310, 1150, 1120, 1060, and 1020 cm$^{-1}$; mass spectrum [(+) FAB], m/z 550/552 (M+H)$^+$, 572/574 (M+Na)$^+$; Anal. Calcd. for C$_{23}$H$_{32}$ClNO$_{12}$.1.0 H$_2$O: C, 48.64; H, 6.03; N, 2.47, Found: C, 48.55; H, 5.90; N, 2.41.

EXAMPLE 2

(R)-N-[5-[[[6-O-Benzoyl-4-O-(4,6-O-ethylidene-α-D-glucopyranosyl)-β-D-glucopyranosyl]oxy]methyl]-2-chlorophenyl]acetamide To a stirred solution of N-{2-chloro-5-[(4',6'-O-ethylidene)-β-D-maltosyloxymethyl]-phenyl}-acetamide (0.323 g, 0.587 mmol) in THF (4.0 mL) at −40° C. was added collidine (4.0 mL, 30.3 mmol) dropwise followed by dropwise addition of BzCl (0.0818 mL, 0.704 mmol). After 2 h at this temperature, it was warmed to rt and stirred an additional 18 h. At this point, the solvent was distilled off using the high vac, and the residue was diluted with EtOAc (200 mL). This layer was washed with 1N HCl (20 mL), sat. NaHCO$_3$ (20 mL), and brine (20 mL) and then dried (MgSO$_4$). After concentration, the oilly residue was purified by flash chromatography (1% to 11% MeOH:CHCl$_3$ gradient) and recrystallization (EtOAc:Et$_2$O) to afford the product (0.209 g, 54%) as a white glassy solid, mp 166–169° C.; $^1$H NMR (DMSO-d$_6$) δ1.19 (d, J=5.1 Hz, 3H), 2.04 (s, 3H), 3.09 (t, J=9.4 Hz, 1H), 3.14–3.21 (m, 1H), 3.27–3.36 (m, 2H), 3.45–3.52 (m, 2H), 3.52–3.60 (m, 2H), 3.73 (ddd, J=1.5, 5.1, 9.4 Hz, 1H), 3.89 (dd, J=4.8, 9.9 Hz, 1H), 4.30 (dd, J=5.5, 12.1 Hz, 1H), 4.38 (d, J=7.7 Hz, 1H), 4.53–4.61 (m, 2H), 4.65 (q, J=5.1 1H), 4.73 (d, J=12.5 Hz, 1H), 5.07 (d, J=4.0 Hz, 1H), 5.28 (d, J=5.3 Hz, 1H), 5.34 (d, J=5.3 Hz, 1H), 5.55 (d, J=2.9 Hz, 1H), 5.77 (d, J=5.9 Hz, 1H), 7.18 (dd, J=2.0, 8.1 Hz, 1H), 7.40 (d, J=8.1 Hz, 1H), 7.50–7.55 (m, 2H), 7.62–7.68 (m, 2H), 7.96–8.00 (m, 2H), 9.50 (s, 1H); IR (KBr) 3450, 3360, 2990, 2910, 2860, 1725, 1750, 1600, 1520, 1450, 1420, 1385, 1375, 1260, 1230, 1130, 1110, 1075, 1055, and 1020 cm$^{-1}$; mass spectrum [(+) FAB], m/z 654/656 (M+H)$^+$, 676/678 (M+Na)$^+$, 692/694 (M+K)$^+$; Anal. Calcd. for C$_{30}$H$_{36}$ClNO$_{13}$: C, 55.09; H, 5.55; N, 2.14, Found: C, 54.76; H, 5.40; N, 2.00.

EXAMPLE 3

(R)-N-[2-Chloro-5-[[[2,3-di-O-acetyl-6-O-benzoyl-4-O-(2,3-di-O-acetyl-4,6-O-ethylidene-α-D-glucopyranosyl)-β-D-glucopyranosyl]oxy]methyl]phenyl]acetamide To a stirred solution of (R)-N-[5-[[[6-O-benzoyl-4-O-(4,6-O-ethylidene-α-D-glucopyranosyl)-β-D-glucopyranosyl]oxy]methyl]-2-chlorophenyl]acetamide (0.086 g, 0.131 mmol) and triethylamine (0.161 mL, 1.15 mmol) in CH$_2$Cl$_2$ (6 mL) at rt was added dropwise acetic anhydride (0.0544 mL, 0.576 mmol) followed by a catalytic amount of DMAP (0.0064 g, 0.0524 mmol). After 18 h, the mixture was diluted with EtOAc (200 mL). This layer was washed with 1 N HCl (20 mL), sat. aq. NaHCO$_3$ (20 mL), and brine (20 mL) and then dried (Na$_2$SO$_4$). After concentration, the residue was purified by preparatory plate chromatography (10:90 MeOH:CHCl$_3$) to afford the product (0.071 g, 66%) as a white, mp>87° C. (decomp.); $^1$H NMR (DMSO-d$_6$) δ1.13 (d, J=4.8 Hz, 3H), 1.92 (s, 3H), 1.95 (s, 3H), 1.97 (s, 3H), 1.99 (s, 3H), 2.05 (s, 3H), 3.31–3.39 (m, 1H), 3.55–3.67 (m, 3H), 4.10–4.19 (m, 2H), 4.41 (dd, J=3.1, 12.3 Hz, 1H), 4.54 (d, J=12.7 Hz, 1H), 4.64–4.74 (m, 3H), 4.77 (dd, J=8.3, 9.4 Hz, 1H), 4.82 (dd, J=4.0, 10.1 Hz, 1H), 4.89 (d, J=7.9 Hz, 1H), 5.18 (t, J=9.7 Hz, 1H), 5.29 (d, J=4.2 Hz, 1H), 5.33 (t, J=9.0 Hz, 1H), 7.04 (dd, J=1.5, 8.1 Hz, 1H), (d, J=8.1 Hz, 1H), 7.55 (t, J=7.7 Hz, 2H), 7.61 (s, 1H), 7.68 (t, J=7.5 Hz, 1H), 8.01–8.07 (m, 2H), 9.45 (s, 1H); IR (KBr) 3410, 2940, 2850, 1755, 1690, 1590, 1530, 1440, 1420, 1370, 1240, 1135, 1060, and 1030 cm$^{-1}$; mass spectrum [(+) FAB], m/z 822/824 (M+H)$^+$, 844/846 (M+Na)$^+$; Anal. Calcd. for $C_{38}H_{44}ClNO_{17}$.1.5 $H_2O$: C, 53.74; H, 5.58; N, 1.65, Found: C, 53.69; H, 5.14; N, 1.57.

EXAMPLE 4

N-{2-Chloro-5-[(4',6'-O-propylidene-β-D-maltosyl)-oxy-methyl]-pheny}-acetamide The title compound was prepared as a white solid (0.309 g, 57%) from N-[2-chloro-5-(β-D-maltosyl-oxymethyl)-phenyl]-acetamide using propionaldehyde diethyl acetal and a procedure similar to step 5 of Example 1, mp>64° C. (decomp.); $^1$H NMR (DMSO-$d_6$) δ0.86 (t, J=7.5 Hz, 3H), 1.48–1.58 (m, 2H), 2.07 (s, 3H), 3.04–3.14 (m, 2H), 3.25–3.58 (m, 8H), 3.68 (dd, J=6.2, 10.5 Hz, 1H), 3.95 (dd, J=4.6, 9.9 Hz, 1H), 4.28 (d, J=7.7 Hz, 1H), 4.48 (t, J=5.1 Hz, 1H), 4.65 (t, J=5.9 Hz, 1), 4.67 (ABq, J=12.5 Hz, Δδ=0.22, 2H), 5.08 (d, J=4.0 Hz, 1H), 5.20 (d, J=5.3 Hz, 1H), 5.24 (d, J=5.3 Hz, 1H), 5.48 (d, J=3.3 Hz, 1H), 5.57 (d, J=6.6 Hz, 1H), 7.22 (dd, J=1.8, 8.3 Hz, 1H), 7.44 (d, J=8.3 Hz, 1H), 7.65 (s, 1H), 9.52 (s, 1H); IR (KBr) 3400, 2980, 2920, 2840, 1675, 1580, 1530, 1460, 1425, 1375, 1310, 1275, 1150, 1060, and 1020 cm$^-$; mass spectrum [(+) FAB], m/z 586/588 (M+Na)$^+$; Anal. Calcd. for $C_{24}H_{34}ClNO_{12}$.1.0 $H_2O$: C, 49.53; H, 6.23; N, 2.41, Found: C, 49.89; H, 6.38; N, 2.19.

EXAMPLE 5

N-{5-[(6-O-Benzoyl-4',6'-O-propylidene-β-D-maltosyl)-oxy-methyl]-2-chloro-phenyl}-acetamide The title compound was prepared as a white solid (0.140 g, 47%) from N-{2-chloro-5-[(4',6'-O-propylidene-β-D-maltosyl)-oxy-methyl]-phenyl}-acetamide using a procedure similar to Example 2, mp>88° C. (decomp.); $^1$H NMR (DMSO-$d_6$) δ0.84 (t, J=7.5 Hz, 3H), 1.45–1.57 (m, 2H), 2.04 (s, 3H), 3.08 (t, J=5.1 Hz, 1H), 3.17 (dd, J=8.3, 13.2 Hz, 1H), 3.26–3.37 (m, 2H), 3.45–3.59 (m, 4H), 3.70–3.77 (m, 1H), 3.91 (dd, J=4.6, 9.7 Hz, 1H), 4.30 (dd, J=5.3, 12.1 Hz, 1H), 4.38 (d, J=7.7 Hz, 1H), 4.43 (t, J=4.8 Hz, 1H), 4.53–4.61 (m, 2H), 4.73 (d, J=12.3 Hz, 1H), 5.07 (d, J=3.5 Hz, 1H), 5.25 (d, J=5.3 Hz, 1H), 5.34 (d, J=5.1 Hz, 1H), 5.56 (d, J=2.2 Hz, 1H), 5.77 (d, J=5.9 Hz, 1H), 7.18 (d, J=8.1 Hz, 1H), 7.39 (d, J=8.3 Hz, 1H), 7.53 (t, J=7.7 Hz, 2H), 7.61–7.68 (m, 2H), 7.98 (d, J=7.5 Hz, 2H), 9.45 (s, 1H); IR (KBr) 3410, 2970, 2920, 2860, 1720, 1675, 1590, 1530, 1450, 1420, 1375, 1270, 1060, 1020, and 720 cm$^{-1}$; mass spectrum [(−) FAB], m/z 666 (M−H)$^-$; Anal. Calcd. for $C_{31}H_{38}ClNO_{13}$: C, 55.73; H, 5.73; N, 2.09, Found: C, 55.67; H, 5.71; N, 2.09.

EXAMPLE 6

N-(5-{[4',6'-O-Benzylidene-6-O-(4-toluenesulfonyl)-β-D-maltosyl]-oxy-methyl}2-chloro-phenyl)-acetamide Step 1

N-{5-[(4',6'-O-Benzylidene-β-D-maltosyloxy)-methyl]-2-chloro-phenyl}-acetamide To a stirred solution of N-[2-chloro-5-(β-D-maltosyl-oxymethyl)-phenyl]-acetamide (14.15 g, 27.0 mmol) in DMF (325 mL) at rt was added benzaldehyde dimethyl acetal (8.11 mL, 54.0 mmol) dropwise followed by TsOH.$H_2O$ (2.57 g, 13.5 mmol). The reaction mixture was heated to 60° C. for 6 h and then quenched with $K_2CO_3$ (1.87 g, 13.5 mmol) with an additional 0.5 h heating at this temperature. At this point, the solution was filtered hot, and the solvent was distilled off using the high vac. The residue was purified by flash chromatography (80:2:1 to 20:2:1 EtOAc:EtOH:$H_2O$ gradient) to afford the product (10.8 g, 65%) as a white solid, mp 143–147° C.; $^1$H NMR (DMSO-$d_6$) δ2.08 (s, 3H), 3.07–3.12 (m, 1H), 3.28–3.50 (m, 5H), 3.51–3.60 (m, 2H), 3.64–3.75 (m, 3H), 4.10–4.12 (m, 1H), 4.30 (d, J=7.9 Hz, 1H), 4.67 (t, 5.9 Hz, 1H), 4.68 (ABq, J=12.5 Hz, Δδ=0.22, 2H), 5.14 (d, J=4.0 Hz, 1H), 5.25 (d, J=5.1 Hz, 1H), 5.30 (d, J=5.3 Hz, 1H), 5.51 (d, J=3.3 Hz, 1H), 5.57 (s, 1H), 5.63 ( d, J=6.8 Hz, 1H), 7.22 (dd, J=1.5, 8.3 Hz, 1H), 7.35–7.38 (m, 3) 7.42–7.46 (m, 3H), 7.66 (s, 1H), 9.53 (s, 1H); IR (KBr) 3500, 3410, 2910, 2850, 1700, 1600, 1550, 1440, 1425, 1375, 1310, 1230, 1150, 1070, and 1030 cm$^{-1}$; mass spectrum [(+) FAB], m/z 634 (M+Na)$^+$; Anal. Calcd. for $C_{28}H_{34}ClNO_{12}$.1.0 $H_2O$: C, 53.38; H, 5.76; N, 2.22, Found: C, 53.58; H, 5.62; N, 2.25.

Step 2

N-(5-{[4',6'-O-Benzylidene-6-O-(4-toluenesulfonyl)-β-D-maltosyl]-oxy-methyl}-2-chloro-phenyl)-acetamide At 0° C., to a stirred solution of N-{5-[(4',6'-O-benzylidene-β-D-maltosyloxy)-methyl]-2-chloro-phenyl}-acetamide (1.81 g, 2.96 mmol) in pyridine (6.0 mL) was added a solution of p-toluenesulfonyl chloride (0.686 g, 3.60 mmol) in $CH_2Cl_2$ (3.75 mL). After 2 h, additional p-toluenesulfonyl chloride (0.686 g, 3.60 mmol) in $CH_2Cl_2$ (3.75 mL) was added and the solution was stirred at 0° C. for 2 h. The reaction was quenched with ice cold $H_2O$ (50 mL) and extracted with EtOAc. The combined organic extracts were washed successively with sat. aq. $NaHCO_3$ (2×), sat. aq. $CuSO_4$ (2×), brine (2×), dried ($Na_2SO_4$) and concentrated. Purification by flash chromatography (5–10% MeOH:$CH_2Cl_2$ gradient) gave 0.930 g, (41%) of a colorless solid, mp 105–120° C.; $^1$H NMR (DMSO-$d_6$) δ2.08 (s, 3H), 2.33 (s, 3H), 3.04–3.09 (m, 1H), 3.27–3.45 (m, 4H), 3.49–3.53 (m, 1H), 3.60–3.65 (m, 3H), 3.95 (d, 1H), 4.13 (dd, 1H), 4.29–4.33 (m, 2H), 4.46 (d, 1H), 4.62 (d, 1 H), 5.05 (d, 1 H), 5.33–5.35 (m, 2H), 5.55 (d, 1H), 5.57 (s, 1H), 5.75 (d, 1H), 7.18 (d, 1H), 7.35–7.47 (m, 8H), 7.78 (d, 2H), 9.53 (s, 1H); mass spectrum [(+) ESI], m/z 766/768 (M+H)$^+$, 783/785 (M+NH$_4$)$^+$; Anal. Calcd. for $C_{35}H_{40}NClO_{14}S.H_2O$: C, 53.60; H, 5.40; N, 1.79, Found: C, 53.46; H, 5.18; N, 1.80.

EXAMPLE 7

N-(5-{[2,32',3'-Tetra-O-acetyl-4',6'-O-benzylidene-6-O-(4-toluenesulfonyl)-β-D-maltosyl]-oxy-methyl}-2-chloro-phenyl)-acetamide The title compound was prepared as a colorless solid (0.942 g, 99%) from N-(5-{[4',6'-O-benzylidene-6-O-(4-toluenesulfonyl)-β-D-maltosyl]-oxy-methyl}-2-chloro-phenyl)-acetamide using a procedure similar to Example 3, mp 116–122° C.; $^1$H NMR (DMSO-$d_6$) δ1.91 (s, 3H), 1.92 (s, 3H), 1.96 (s, 3H), 2.00 (s, 3H), 2.08 (s, 3H), 2.29 (s, 3H), 3.68 (dd, 1H), 3.77 (t, 1H), 3.85 (t, 1H), 3.90 (t, 1H), 3.97–4.00 (m, 1H), 4.21 (dd, 1H), 4.32 (s, 2H), 4.39 (d, 1H), 4.56 (d, 1H), 4.60 (d, 1H), 4.78 (d, 1H), 4.86 (dd, 1H), 5.17–5.30 (m, 3H), 5.65 (s, 1H), 7.03 (d, 1H), 7.34–7.41 (m, 7H), 7.46 (d, 1H), 7.59 (s, 1H), 7.80 (d, 2H), 9.52 (s, 1H);

mass spectrum [(+) ESI], m/z 934/936 (M+H)+; Anal. Calcd. for $C_{43}H_{48}NClO_{18}S$: C, 55.27; H, 5.17; N, 1.50, Found: C, 55.07; H, 5.05; N, 1.47.

EXAMPLE 8

N-{5-[(6-O-Benzyl-4',6'-O-benzylidene-β-D-maltosyl)-oxy-methyl]-2-chloro-phenyl}-acetamide
Step 1

N-{5-[(2,2',3,3'-Tetra-O-acetyl-4',6'-O-benzylidene-β-D-maltosyl)-oxy-methyl]-2-chloro-phenyl}-acetamide A solution containing N-(5-{[2,3,2',3'-tetra-O-acetyl-4',6'-O-benzylidene-6-O-(4-toluenesulfonyl)-β-D-maltosyl]-oxy-methyl}-2-chloro-phenyl)-acetamide (1.021 g, 1.093 mmol) and sodium formate (0.1858 g, 2.732 mmol) in EtOH:DMSO:H₂O (2:2:1, 21.9 mL) was heated at 100° C. for 2 days. The reaction was cooled to ambient temperature, diluted with 10% CH₂Cl₂:EtOAc (100 mL), washed with brine (3x), dried (MgSO₄) and concentrated in vacuo. Purification by flash chromatography (1,2 and 3% MeOH:CHCl₃ gradient) gave 0.446 g (52%) of title compound as a colorless solid; ¹H NMR (DMSO-d₆) δ1.93 (s, 3H), 1.95 (s, 3H), 1.98 (s, 3H), 2.01 (s, 3H), 2.08 (s, 3H), 3.68–3.99 (m, 7H), 4.19–4.22 (m, 1H), 4.57 (d, J=12.7 Hz, 1H), 4.64–4.87 (m, 4H), 5.00 (br.s, 1H), 5.21–5.33 (m, 3H), 5.63 (s, 1H), 7.08 (dd, J=8.3, 1.8 Hz, 1H), 7.38 (s, 5H), 7.47 (d, J=8.2 Hz, 1H), 7.64 (s, 1H), 9.53 (s, 1H).
Step 2

N-{5-[(2,2',3,3'-Tetra-O-acetyl-6-O-benzyl-4',6'-O-benzylidene-β-D-maltosyl)-oxy-methyl]-2-chloro-phenyl}-acetamide At ambient temperature, to a stirred solution containing N-{5-[(2,2',3,3'-tetra-O-acetyl-4',6'-O-benzylidene-β-D-maltosyl)-oxy-methyl]-2-chloro-phenyl}-acetamide (0.221 g, 0.283 mmol) and benzyl 2,2,2-trichloroacetimidate (0.105 mL, 0.567 mmol) in 10% CH₂Cl₂:benzene (10 mL) was added trifluoromethane sulfonic acid (1 drop). After 16 h, the reaction was diluted with 5% MeOH:CHCl₃ (10 mL), filtered through a 1" silica gel pad eluting with 5% MeOH:CHCl₃ and concentrated in vacuo. Purification by flash chromatography (1 and 2% MeOH:CHCl₃ gradient) gave 0.134 g (54%) of title compound as a colorless solid; ¹H NMR (DMSO-d₆) δ1.94 (s, 3H), 1.96 (s, 3H), 1.98 (s, 3H), 2.01 (s, 3H), 2.07 (s, 3H), 3.69–4.07 (m, 8H), 4.54–4.59 (m, 3H), 4.69–4.77 (m, 2H), 4.82–4.86 (m, 2H), 5.23–5.34 (m, 3H), 5.6 (s, 1H), 7.09 (dd, J=8.3, 1.7 Hz, 1H), 7.27–7.37 (m, 10H), 7.46 (d, J=8.2 Hz, 1H), 7.65 (s, 1H), 9.52 (s, 1H).
Step 3

N-{5-[(6-O-Benzyl-4',6'-O-benzylidene-β-D-maltosyl)-oxy-methyl]-2-chloro-phenyl}-acetamide The title compound was prepared as a colorless solid (0.085 g, 65%) from N-{5-[(2,2',3,3'-tetra-O-acetyl-6-O-benzyl-4',6'-O-benzylidene-β-D-maltosyl)-oxy-methyl]-2-chloro-phenyl}-acetamide using a procedure similar to step 4 of Example 1, mp 98–105° C.; ¹H NMR (DMSO-d₆) δ2.06 (s, 3H), 3.09–3.11 (m, 1H), 3.28–3.75 (m, 10H), 3.99 (dd, 1H), 4.33 (d, J=7.7 Hz, 1H), 4.50 (s, 1H), 4.51 (s, 1H), 4.66 (ABq, J=12.6 Hz, Δδ=0.08, 2H), 5.14 (d, J=3.7 Hz, 1H), 5.30 (d, J=9.0 Hz, 1H), 5.31 (d, J=9.0 Hz, 1H), 5.56–5.57 (m, 2H), 5.70 (d, J=6.6 Hz, 1H), 7.21–7.38 (m, 9H), 7.42–7.45 (m, 3H), 7.66 (s, 1H), 9.52 (s, 1H); mass spectrum [(+) FAB], m/z 724 (M+H)+; Anal. Calcd. for $C_{35}H_{40}NClO_{12}$·0.5 H₂O: C, 59.11; H, 5.81; N, 1.97, Found: C, 59.12; H, 5.76; N, 1.98.

EXAMPLE 9

N-{5-[(6-O-Benzyl-4',6'-O-ethylidene-β-D-maltosyl)-oxy-methyl]-2-chloro-phenyl}-acetamide
Step 1

N-{5-[(2,2', 3,3'-Tetra-O-acetyl-6-O-benzyl-β-D-maltosyl)-oxy-methyl]-2-chloro-phenyl}-acetamide At ambient temperature, to a stirred solution of N-{5-[(2,2',3,3'-tetra-O-acetyl -6-O-benzoyl-4',6'-O-benzylidene-β-D-maltosyl)-oxy-methyl]-2-chloro-phenyl}-acetamide (0.202 g, 0.232 mmol) in MeOH (5 mL) was added 1M ethereal HCl. After 2 h, the reaction was quenched with sat. aq. NaHCO₃ (25 mL), diluted with H₂O (25 mL), extracted with EtOAc, dried (Na₂SO₄) and concentrated. Purification by flash chromatography (5% MeOH:CHCl₃) gave 0.136 g (75%) of title compound; ¹H NMR (DMSO-d₆) δ1.92 (s, 3H), 1.95 (s, 6H), 2.00 (s, 3H), 2.07 (s, 3H), 3.49–3.56 (m, 4H), 3.75–3.94 (m, 4H), 4.50–4.59 (m, 5H), 4.67–4.76 (m, 2H), 4.83 (d, J=7.9 Hz, 1H), 5.06–5.13 (m, 1H), 5.21–5.29 (m, 2H), 5.44 (d, J=6.0 Hz, 1H), 7.08 (dd, J=8.1, 1.5 Hz, 1H), 7.26–7.36 (m, 5H), 7.45 (d, J=8.2 Hz, 1H), 7.64 (s, 1H), 9.52 (s, 1H).
Step 2

N-{5-[(2,2',3,3'-Tetra-O-acetyl-6-O-benzyl-4',6'-O-ethylidene-β-D-maltosyl)-oxy-methyl]-2-chloro-phenyl}-acetamide A stirred solution containing N-{5-[(2,2',3,3'-tetra-O-acetyl-6-O-benzyl-β-D-maltosyl)-oxy-methyl]-2-chloro-phenyl}-acetamide (0.274 g, 0.350 mmol), priopionaldehyde (45.5 μL, 0.630 mmol) and camphor sulfonic acid (18.3 mg, 0.0787 mmol) in benzene (6.3 mL) was refluxed with Dean-Stark azeotropic removal of water. After 2.5 h, The reaction was cooled to room temperature, quenched with NaHCO₃ (25 mL), extracted with EtOAc and dried (Na₂SO₄). Purification by flash chromatography (1, 2 and 3% MeOH:CHCl₃ gradient) gave 0.346 g (96%) of title compound; ¹H NMR (DMSO-d₆) δ0.82 (t, 3H), 1.48–1.53 (m, 2H), 1.92 (s, 3H), 1.95 (s, 3H), 1.97 (s, 3H), 2.01 (s, 3H), 2.07 (s, 3H), 3.41–3.48 (m, 1H), 3.60–3.64 (m, 2H), 3.71–4.03 (m, 5H), 4.49–4.69 (m, 4H), 4.70–4.85 (m, 4H), 5.14–5.32 (m, 3H), 7.07–7.36 (m, 6H), 7.46 (d, J=8.2 Hz, 1H), 7.64 (s, 1H), 9.52 (s, 1H).
Step 3

N-{5-[(6-O-Benzyl-4',6'-O-ethylidene-β-D-maltosyl)-oxy-methyl]-2-chloro-phenyl}-acetamide A solution containing N-{5-[(2,2',3,3'-tetra-O-acetyl-6-O-benzyl-4',6'-O-ethylidene-β-D-maltosyl)-oxy-methyl]-2-chloro-phenyl}-acetamide (0.217 g, 0.264 mmol) and 25 weight % NaOMe in MeOH (0.0285 g, 0.132 mmol) in MeOH (5.3 mL) was refluxed for 3 h. The reaction was cooled to room temperature and concentrated. Purification by flash chromatography (10% MeOH/CH₂Cl₂ gradient) gave the product (0.100 g, 58%) as a white solid, mp 182–185° C.; ¹H NMR (DMSO-d₆) δ0.85 (t, J=7.5 Hz, 3H), 1.21–1.55 (m, 2H), 2.05 (s, 3H), 3.05–3.13 (m, 2H), 3.24–3.70 (m, 9H), 3.83 (dd, J=9.8, 4.7 Hz, 1H), 4.30 (d, J=7.7 Hz, 1H), 4.43–4.49 (m, 3H), 4.63 (ABq, J=12.4 Hz, Δδ=0.07, 2H), 5.07 (d, J=3.5 Hz, 1H), 5.24 (d, J=5.3 Hz, 1H), 5.31 (d, J=5.3 Hz, 1H), 5.55 (d, J=2.6 Hz, 1H), 5.65 (d, J=6.6 Hz, 1H), 7.17–7.34 (m, 6H), 7.41 (d, J=8.3 Hz, 1H), 7.63 (s, 1H), 9.55 (s, 1H). mass spectrum [(+) ESI]671 (M+NH$_4$)$^+$; Anal. Calcd. for C$_{31}$H$_{40}$NClO$_{12}$: C, 56.92; H, 6.16; N, 2.14, Found: C, 56.69; H, 6.33; N, 1.99.

EXAMPLE 10

N-(2-Chloro-5-{[4',6'-O-(4-nitro)-benzylidene-β-D-maltosyl]-oxy-methyl}-phenyl)-acetamide To a stirred solution of N-[2-chloro-5-(β-D-maltosyl-oxymethyl)-phenyl]-acetamide (0.500 g, 0.954 mmol) in DMF (30 mL) at rt was added 3-nitro-benzaldehyde dimethyl acetal (0.752 g, 3.82 mmol) followed by CSA (0.111 g, 0.477 mmol). The reaction mixture was heated to 60° C. for 18 h and was about 35% complete by TLC. Another 0.5 eq. CSA (0.111 g) added and heated at 90° C. for 3 h. The reaction was then quenched with K$_2$CO$_3$ (0.132 g, 0.954 mmol) with an additional 0.5 h heating at 60° C. At this point, the solution was filtered hot, and the solvent was distilled off using the high vac. The residue was purified by flash chromatography (40:2:1 to 20:2:1 EtOAc:EtOH:H$_2$O gradient) to afford the product (0.262 g, 42%) as a white solid, mp 221–223° C.; $^1$H NMR (DMSO-d$_6$) δ2.07 (s, 3H), 3.06–3.12 (m, 1H), 3.26–3.49 (m, 5H), 3.49–3.62 (m, 2H), 3.68–3.77 (m, 3H), 4.11–4.20 (m, 1H), 4.30 (d, J=7.7 Hz, 1H), 4.67 (t, J=5.7 Hz, 1H), 4.68 (ABq, J=12.3 Hz, Δδ=0.22, 2H), 5.16 (d, J=3.7 Hz, 1H), 5.25 (d, J=4.8 Hz, 1H), 5.36 (d, J=4.8 Hz, 1H), 5.49 (d, J=3.1 Hz, 1H), 5.62 (d, J=6.6 Hz, 1H), 5.74 (s, 1H), 7.22 (dd, J=1.8, 8.1 Hz, 1H), 7.44 (d, J=8.3 Hz, 1H), 7.65 (s, 1H), 7.73 (d, J=8.8 Hz, 2H), 8.25 (dt, J=2.2, 9.0 Hz, 2H), 9.52 (s, 1H); IR (KBr) 3410, 2910, 2870, 1670, 1610, 1590, 1530, 1440, 1420, 1355, 1320, 1265, 1140, 1075, and 1035 cm$^{-1}$; mass spectrum [(-) FAB], m/z 655 (M-H$^-$); Anal. Calcd. for C$_{28}$H$_{33}$ClN$_2$O$_{14}$: C, 51.19; H, 5.06; N, 4.26, Found: C, 50.87; H, 4.87; N, 4.32.

EXAMPLE 11

N-(5-{[6-O-Benzoyl-4',6'-O-(4-nitro)-benzylidene-β-D-maltosyl]-oxy-methyl}-2-chloro-phenyl)-acetamide The title compound was prepared as a white solid (0.080 g, 35%) from N-(2-chloro-5-{[4',6'-O-(4-nitro)-benzylidene-β-D-maltosyl]-oxy-methyl}-phenyl)-acetamide using the procedure of Example 2, mp>167° C. (decomp.); $^1$H NMR (DMSO-d$_6$) δ2.04 (s, 3H), 3.15–3.22 (m, 1H), 3.37–3.43 (m, 2H), 3.51 (td, J=2.9, 8.8 Hz, 1H), 3.57–3.64 (m, 3H), 3.70–3.78 (m, 2H), 4.09 (dd, J=4.6, 9.9 Hz, 1H), 4.35 (dd, J=5.1, 12.3 Hz, 1H), 4.39 (d, J=7.7 Hz, 1H), 4.57–4.63 (m, 1H), 4.65 (ABq, J=12.3 Hz, Δδ=0.14, 2H), 5.15 (d, J=4.0 Hz, 1H), 5.36 (d, J=5.3 Hz, 1H), 5.41 (d, J=5.3 Hz, 1H), 5.57 (d, J=3.1 Hz, 1H), 5.70 (s, 1H), 5.81 (d, J=6.2 Hz, 1H), 7.19 (dd, J=1.8, 8.1 Hz, 1H), 7.40 (d, J=8.1 Hz, 1H), 7.50–7.56 (m, 2H), 7.62–7.72 (m, 4H), 7.97–8.01 (m, 2H), 8.24 (dt, J=2.4, 9.2 Hz, 2H), 9.45 (s, 1H); IR (KBr) 3410, 2850, 1725, 1660, 1610, 1590, 1530, 1445, 1420, 1355, 1270, 1120, 1075, 1025, and 715 cm$^{-1}$; mass spectrum [(+) FAB], m/z 783 (M+Na)$^+$; Anal. Calcd. for C$_{35}$H$_{37}$ClN$_2$O$_{15}$.1.0 H$_2$O: C, 53.95; H, 5.05; N, 3.60, Found: C, 53.86; H, 4.75; N, 3.51.

EXAMPLE 12

N-{2-Chloro-5-[(4',6'-O-(4-chloro)-benzylidene-β-D-maltosyl)-oxy-methyl]-phenyl}-acetamide The title compound was prepared as a white glass (0.315 g, 51%) from N-[2-chloro-5-(β-D-maltosyl-oxymethyl)-phenyl]-acetamide using p-chloro-benzaldehyde dimethyl acetal and the procedure of Example 10, mp>97° C. (decomp.); $^1$H NMR (DMSO-d$_6$) δ2.07 (s, 3H), 3.09 (t, J=8.8 Hz, 1H), 3.28–3.48 (m, 5H), 3.49–3.61 (m, 2H), 3.61–3.75 (m, 3H), 4.11 (d, J=5.3 Hz, 1H), 4.30 (d, J=7.7 Hz, 1H), 4.63–4.72 (bs, 1H), 4.68 (ABq, J=12.3 Hz, Δδ=0.22, 2H), 5.14 (d, J=4.0 Hz, 1H), 5.21–5.36 (bs, 2H), 5.47–5.53 (bs, 1H), 5.57–5.66 (bs, 1H), 5.59 (s, 1H), 7.22 (dd, J=2.0, 8.3 Hz, 1H), 7.42–7.48 (m, 5H), 7.65 (s, 1H), 9.52 (s, 1H); IR (KBr) 3390, 2920, 2850, 1670, 1590, 1530, 1500, 1450, 1420, 1365, 1300, 1140, 1070, 1030, and 815 cm$^{-1}$; mass spectrum [(+) FAB], m/z 668 (M+Na)$^+$; Anal. Calcd. for C$_{28}$H$_{33}$Cl$_2$NO$_{12}$.0.5 H$_2$O: C, 51.31; H, 5.23; N, 2.14, Found: C, 51.13; H, 5.44; N, 1.92.

EXAMPLE 13

N-{1 5-[(6-O-Benzoyl-4',6'-O-(4-chloro)-benzylidene-β-D-maltosyl)-oxy-methyl]-2-chloro-phenyl}-acetamide The title compound was prepared as a white solid (0.158 g, 50%) from N-{2-chloro-5-[(4',6'-O-(4-chloro)-benzylidene-β-D-maltosyl)-oxy-methyl]-phenyl}-acetamide using a procedure similar to Example 2, mp>182° C. (decomp.); $^1$H NMR (DMSO-d$_6$) δ2.05 (s, 3H), 3.15–3.22 (m, 1H), 3.28–3.43 (m, 2H), 3.48–3.63 (m, 4), 3.67–3.73 (m, 1H), 3.73–3.78 (m, 1H), 4.03–4.07 (m, 1H), 4.32–4.37 (m, 1H), 4.39 (d, J=7.9 Hz, 1H), 4.57–4.63 (m, 1H), 4.65 (ABq, J=12.5 Hz, Δδ=0.14, 2H), 5.14 (d, J=4.0 Hz, 1H), 5.36 (dd, J=2.6, 5.1 Hz, 2H), 5.54 (s, 1H), 5.56 (d, J=3.1 Hz, 1H), 5.79 (d, J=6.4 Hz, 1H), 7.19 (dd, J=2.0, 8.3 Hz, 1H), 7.40 (d, J=8.3 Hz, 1H), 7.43 (s, 4H), 7.53 (t, J=7.9 Hz, 2H), 7.63–7.68 (m, 2H), 7.99 (dd, J=0.9, 7.9 Hz, 2H), 9.50 (s, 1H); IR (KBr) 3450, 3380, 2960, 2900, 2860, 1730, 1700, 1665, 1590, 1530, 1495, 1440, 1415, 1365, 1310, 1280, 1140, 1075, 1050, 1035, 1015, 820, and 720 cm$^{-1}$; mass spectrum [(+) FAB], m/z 750 (M+H)$^+$, 772 (M+Na)$^+$; Anal. Calcd. for C$_{35}$H$_{37}$Cl$_2$NO$_{13}$: C, 56.01; H, 4.97; N, 1.87, Found: C, 55.67; H, 4.91; N, 1.87.

EXAMPLE 14

N-{2-Chloro-5-[(4',6'-O-isobutylidene-β-D-maltosyl)-oxy-methyl]-phenyl}-acetamide The title compound was prepared as a white solid (0.250 g, 45%) from N-[2-chloro-5-(β-D-maltosyl-oxymethyl)-phenyl]-acetamide using isobutyraldehyde diethyl acetal and the procedure of Example 10, mp>122° C. (decomp.); $^1$H NMR (DMSO-d$_6$) δ0.87 (dd, J=5.5, 6.6 Hz, 6H), 1.68–1.78 (m, 1H), 2.07 (s, 3H), 3.04–3.13 (m, 2H), 3.24–3.55 (m, 8H), 3.68 (dd, J=6.2, 10.5 Hz, 1H), 3.97 (dd, J=4.6, 9.7 Hz, 1H), 4.27 (s, 1H), 4.28 (d, J=3.7 Hz, 1H), 4.65 (t, J=5.9 Hz, 1H), 4.67 (ABq, J=12.5 Hz, Δδ=0.22, 2H), 5.06 (d, J=4.0 Hz, 1H), 5.17 (d, J=5.3 Hz, 1H), 5.24 (d, J=5.3 Hz, 1H), 5.50 (d, J=3.3 Hz, 1H), 5.59 (d, J=6.6 Hz, 1H), 7.22 (dd, J=1.5, 7.9 Hz, 1H), 7.44 (d, J=8.3 Hz, 1H), 7.65 (s, 1H), 9.52 (s, 1H); IR (KBr) 3420, 2960, 2910, 2830, 1670, 1590, 1530, 1460, 1420, 1370, 1310, 1255, 1145, 1080, 1055, and 1030 cm$^{-1}$; mass spectrum [(-) ESI], m/z 576 (M-H)$^-$; Anal. Calcd. for C$_{25}$H$_{36}$ClNO$_{12}$.0.5 H$_2$O: C, 51.15; H, 6.35; N, 2.39, Found: C, 51.06; H, 6.56; N, 2.45.

EXAMPLE 15

N-{5-[(6-O-Benzoyl-4',6'-O-isobutylidene-β-D-maltosyl)-oxy-methyl]-2-chloro-phenyl}-acetamide The title compound was prepared as a white solid (0.079 g, 41%) from N-{2-chloro-5-[(4',6'-O-isobutylidene-β-D- maltosyl)-oxy-methyl]-phenyl}-acetamide using the procedure of Example 2, mp>123° C. (decomp.); $^1$H NMR (DMSO-$d_6$) δ0.85 (t, J=6.4 Hz, 6H), 1.66–1.75 (m, 1H), 2.05 (s, 3H), 3.07 (t, J=9.4 Hz, 1H), 3.15–3.21 (m, 1H), 3.26–3.36 (m, 2H), 3.46–3.60 (m, 4H), 3.72–3.77 (m, 1H), 3.92 (dd, J=4.8, 10.1 Hz, 1H), 4.23 (d, J=4.8 Hz, 1H), 4.30 (dd, J=5.1, 12.1 Hz, 1H), 4.38 (d, J=7.7 Hz, 1H), 4.57 (d, J=10.5 Hz, 1H), 4.64 (ABq, J=12.5 Hz, Δδ=0.14, 2H), 5.06 (d, J=4.0 Hz, 1H), 5.21 (d, J=4.8 Hz, 1H), 5.34 (d, J=5.1 Hz, 1H), 5.57 (d, J=2.2 Hz, 1H), 5.76 (d, J=5.9 Hz, 1H), 7.18 (dd, J=1.5, 8.3 Hz, 1H), 7.40 (d, J=8.3 Hz, 1H), 7.53 (t, J=7.9 Hz, 2H), 7.61–7.68 (m, 2H), 7.96–8.01 (m, 2H), 9.50 (s, 1H); IR (KBr) 3410, 2960, 2910, 2840, 1725, 1660, 1610, 1590, 1530, 1440, 1425, 1375, 1270, 1080, 1055, 1025, and 715 cm$^{-1}$; mass spectrum [(−) APCI], m/z 681.0/683.1 (M)$^-$, Anal. Calcd. for $C_{32}H_{40}ClNO_{13}$·1.0 $H_2O$: C, 54.90; H, 6.05; N, 2.00, Found: C, 54.95; H, 5.90; N, 1.94.

EXAMPLE 16

N-{5-[(4',6'-O-((1R)-2-Phenyl-ethylidene)-β-D-maltosyloxy)-methyl]-2-chloro-phenyl}-acetamide The title compound was prepared as a white solid (0.210 g, 35%) from N-[2-chloro-5-(β-D-maltosyl-oxymethyl)-phenyl]-acetamide using phenylacetaldehyde dimethyl acetal and the procedure of Example 10, mp >106° C. (decomp.); $^1$H NMR (DMSO-$d_6$) δ2.07 (s, 3H), 2.81 (dd, J=6.4, 14.1, 1H), 2.91 (dd, J=4.0, 14.1 Hz, 1H), 3.04–3.11 (m, 1H), 3.16 (t, J=9.4 Hz, 1H), 3.26–3.54 (m, 7H), 3.58 (td, J=5.1, 10.1 Hz, 1H), 3.65–3.72 (m, 1H), 3.93 (dd, J=4.8, 9.9 Hz, 1H), 4.29 (d, J=7.7 Hz, 1H), 4.65 (t, J=5.9 Hz, 1H), 4.67 (ABq, J=12.3 Hz, Δδ=0.22, 2H), 4.75 (dd, J=4.2, 6.2 Hz, 1H), 5.09 (d, J=3.7 Hz, 1H), 5.23 (dd, J=5.3, 10.1 Hz, 2H), 5.47 (d, J=3.5 Hz, 1H), 5.57 (d, J=6.6 Hz, 1H), 7.17–7.30 (m, 6H), 7.44 (d, J=8.1 Hz, 1H), 7.65 (s, 1H), 9.52 (s, 1H); IR (KBr) 3400, 2920, 2850, 1670, 1590, 1530, 1450, 1420, 1375, 1310, 1250, 1150, 1130, 1060, 1025, and 750 cm$^{-1}$; mass spectrum [(+) FAB], m/z 648 (M+Na)$^+$; Anal. Calcd. for $C_{29}H_{36}ClNO_{12}$·2.75 $H_2O$: C, 51.56; H, 6.19; N, 2.07, Found: C, 51.47; H, 5.52; N, 2.13.

EXAMPLE 17

N-{5-[(6-O-Benzoyl-4',6'-O-((1R)-2-phenyl-ethylidene)-β-D-maltosyloxy)-methyl]-2-chloro-phenyl}-acetamide The title compound was prepared as a white solid (1.25 g, 63%) from N-{5-[(4',6'-O-((1R)-2-phenyl-ethylidene)-β-D-maltosyloxy)-methyl]-2-chloro-phenyl}-acetamide using the procedure of Example 2, mp 153–156° C.; $^1$H NMR (DMSO-$d_6$) δ2.05 (s, 3H), 2.78 (dd, J=6.2, 14.1 Hz, 1H), 2.89 (dd, J=4.2, 14.3 Hz, 1H), 3.10–3.21 (m, 2H), 3.26–3.37 (m, 2H), 3.47–3.64 (m, 4H), 3.71–3.77 (m, 1H), 3.89 (dd, J=4.8, 9.9 Hz, 1H), 4.31 (dd, J=5.3, 12.1 Hz, 1H), 4.38 (d, J=7.7 Hz, 1H), 4.53–4.60 (m, 2H), 4.68–4.77 (m, 2H), 5.07 (d, J=4.0 Hz, 1H), 5.27 (d, J=5.5 Hz, 1H), 5.34 (d, J=5.3 Hz, 1H), 5.55 (d, J=2.9 Hz, 1H), 5.77 (d, J=6.2 Hz, 1H), 7.16–7.28 (m, 6H), 7.40 (d, J=8.1 Hz, 1H), 7.52 (t, J=7.7 Hz, 2H), 7.62–7.67 (m, 2H), 7.98 (dd, J=0.7, 7.9 Hz, 2H), 9.50 (s, 1H); IR (KBr) 3480, 3370, 2910, 1725, 1695, 1590, 1525, 1450, 1425, 1380, 1355, 1310, 1275, 1250, 1235, 1140, 1120, 1075, 1050, 1035, and 715 cm$^{-1}$; mass spectrum [(−) FAB], m/z 728 (M−H)$^-$; Anal. Calcd. for $C_{36}H_{40}ClNO_{13}$: C, 59.22; H, 5.52; N, 1.92, Found: C, 58.93; H, 5.45; N, 1.86.

EXAMPLE 18

N-{2-Chloro-5[-(4',6'-O-((1R)-3-cyano-propylidene)-β-D-maltosyloxy)-methyl]-phenyl}-acetamide The title compound was prepared as a tan solid (0.101 g, 18%) from N-[2-chloro-5-(β-D-maltosyl-oxymethyl)-phenyl]-acetamide using 3-cyanopropionaldehyde dimethyl acetal and the procedure of Example 10, mp 185–188° C.; $^1$H NMR (DMSO-$d_6$) δ1.82–1.89 (m, 2H), 2.07 (s, 3H), 2.47–2.55 (m, 2H), 3.04–3.11 (m, 1H), 3.15 (t, J=9.2 Hz, 1H), 3.24–3.59 (m, 8H), 3.65–3.71 (m, 1H), 3.99 (dd, J=4.6, 9.9 Hz, 1H), 4.28 (d, J=7.7 Hz, 1H), 4.62–4.67 (m, 2H), 4.67 (ABq, J=12.5 Hz, Δδ=0.22, 2H), 5.10 (d, J=3.7 Hz, 1H), 5.24 (dd, J=5.3, 7.2 Hz, 2H), 5.48 (d, J=3.3 Hz, 1H), 5.58 (d, J=6.6 Hz, 1H), 7.22 (d, J=1.8, 8.1 Hz, 1H), 7.44 (8.1 Hz, 1H), 7.65 (s, 1H), 9.52 (s, 1H); IR (KBr) 3540, 3410, 3120, 2930, 2850, 2230, 1685, 1590, 1540, 1450, 1425, 1420, 1370, 1320, 1255, 1150, 1130, 1100, 1065, 1050, 1020, 995, and 890 cm$^{-1}$; mass spectrum [(+) FAB], m/z 611 (M+Na)$^+$; Anal. Calcd. for $C_{25}H_{33}ClN_2O_{12}$·0.5 $H_2O$: C, 50.21; H, 5.73; N, 4.68, Found: C, 50.32; H, 5.51; N, 4.84.

EXAMPLE 19

N-{5-{[6-O-Benzoyl-4',6'-O-((1R)-3-cyanopropylidene)-β-D-maltosyloxy]-methyl}-2-chloro-phenyl}-acetamide The title compound was prepared as a white solid (0.038 g, 46%) from N-{2-chloro-5-[(4',6'-O-((1R)-3-cyano-propylidene)-β-D-maltosyloxy)-methyl]-phenyl}-acetamide using the procedure of Example 2, mp 164–166° C.; $^1$H NMR (DMSO-$d_6$) δ1.79–1.86 (m, 2H), 2.04 (s, 3H), 2.48–2.52 (m, 2H), 3.13 (t, J=9.2 Hz, 1H), 3.14–3.20 (m, 1H), 3.27–3.40 (m, 2H), 3.46–3.60 (m, 4H), 3.71–3.77 (m, 1H), 3.93 (dd, J=4.6, 9.9 Hz, 1H), 4.30 (dd, J=5.3, 12.1 Hz, 1H), 4.38 (d, J=7.9 Hz, 1H), 4.55–4.62 (m, 2H), 4.64 (ABq, J=12.5 Hz, Δδ=0.14, 2H), 5.08 (d, J=3.7 Hz, 1H), 5.28 (d, J=5.1 Hz, 1H), 5.35 (d, J=5.3 Hz, 1H), 5.55 (d, J=2.9 Hz, 1H), 5.77 (d, J=6.2 Hz, 1H), 7.18 (dd, J=1.5, 8.1 Hz, 1H), 7.40 (d, J=8.1 Hz, 1H), 7.53 (t, J=7.9 Hz, 2H), 7.62–7.68 (m, 2H), 7.98 (dd, J=1.5, 8.3 Hz, 2H), 9.50 (s, 1H); IR (KBr) 3450, 3380, 3320, 2920, 2880, 2240, 1725, 1710, 1670, 1610, 1590, 1530, 1440, 1420, 1370, 1310, 1275, 1125, 1100, 1060, 1030, 1020, and 720 cm$^{-1}$; mass spectrum [(−) FAB], m/z 691 (M−H)$^-$; Anal. Calcd. for $C_{32}H_{37}ClN_2O_{13}$: C, 55.45; H, 5.38; N, 4.04, Found: C, 55.25; H, 5.44; N, 3.90.

EXAMPLE 20

N-{2-Chloro-5-[(4',6'-O-((1R)-3-ethoxy-propylidene)-β-D-maltosyloxy)-methyl]-phenyl}-acetamide The title compound was prepared as a white solid (0.080 g, 14%) from N-[2-chloro-5-(β-D-maltosyl-oxymethyl)-phenyl]-acetamide using 3-chloropropionaldehyde diethyl acetal and the procedure of Example 10, mp 149.5–153° C.; $^1$H NMR (DMSO-$d_6$) δ1.08 (t, J=7.0 Hz, 3H), 1.70–1.81 (m, 2H), 2.07 (s, 3H), 2.44–2.54 (m, 2H), 3.04–3.17 (m, 2H), 3.24–3.60 (m, 10H), 3.64–3.71 (m, 1H), 3.95 (dd, J=4.8, 9.9 Hz, 1H), 4.28 (d, J=7.7 Hz, 1H), 4.63 (dd, J=5.7, 9.7 Hz, 2H), 4.67 (ABq, J=12.3 Hz, Δδ=0.22, 2H), 5.09 (d, J=3.7 Hz, 1H), 5.19 (d, J=5.3 Hz, 1H), 5.23 (d, J=5.3 Hz, 1H), 5.46 (d, J=3.3 Hz, 1H), 5.56 (d, J=6.6 Hz, 1H), 7.22 (dd, J=1.8, 8.1 Hz, 1H), 7.44 (d, J=8.3 Hz, 1H), 7.65 (s, 1H), 9.51 (s, 1H); IR (KBr) 3500, 3420, 2970, 2920, 2840, 1690, 1590, 1530, 1440, 1420, 1370, 1320, 1250, 1110, 1070, and 1020 cm$^{-1}$; mass spectrum [(−) FAB], m/z 606 (M−H)$^-$; Anal. Calcd. for $C_{26}H_{38}ClNO_{13}$·1.5 $H_2O$: C, 49.17; H, 6.51; N, 2.21, Found: C, 48.89; H, 5.93; N, 2.27.

EXAMPLE 21

N-{5-{[6-O-Benzoyl-4',6'-O-((1R)-3-ethoxypropylidene)-β-D-maltosyloxy]-methyl}-2-chloro-phenyl}-acetamide The title compound was prepared as a off-white solid (0.015 g, 26%) from N-{2-chloro-5-[(4',6'-O-((1R)-3- ethoxy-propylidene)-β-D-maltosyloxy)-methyl]-phenyl}-acetamide using the procedure of Example 2, mp >94° C. (decomp.); ¹H NMR (DMSO-d₆) δ1.07 (t, J=7.0 Hz, 3H), 1.69–1.78 (m, 2H), 2.04 (s, 3H), 2.44–2.54 (m, 2H), 3.09 (t, J=9.7 Hz, 1H), 3.14–3.21 (m, 1H), 3.26–3.42 (m, 4H), 3.45–3.60 (m, 4H), 3.71–3.76 (m, 1H), 3.91 (dd, J=4.4, 9.7 Hz, 1H), 4.30 (dd, J=5.3, 12.3 Hz, 1H), 4.37 (d, J=7.7 Hz, 1H), 4.54–4.61 (m, 2H), 4.64 (ABq, J=12.5 Hz, Δδ=0.14, 2H), 5.07 (d, J=4.0 Hz, 1H), 5.25 (d, J=5.3 Hz, 1H), 5.34 (d, J=5.3 Hz, 1H), 5.55 (d, J=2.6 Hz, 1H), 5.77 (d, J=6.2 Hz, 1H), 7.18 (d, J=8.3 Hz, 1H), 7.40 (d, J=8.1 Hz, 1H), 7.53 (t, J=7.9 Hz, 2H), 7.62–7.68 (m, 2H), 7.98 (d, J=7.2 Hz, 2H), 9.50 (s, 1H); IR (KBr) 3410, 2910, 2850, 1720, 1670, 1590, 1530, 1440, 1420, 1370, 1280, 1115, 1060, 1025, and 720 cm⁻¹; mass spectrum [(+) FAB], m/z 734 (M+Na)⁺; Anal. Calcd. for $C_{33}H_{42}ClNO_{14} \cdot 4.0\ H_2O$: C, 50.54; H, 6.43; N, 1.79, Found: C, 50.22; H, 5.28; N, 1.77.

EXAMPLE 22

N-(2-Chloro-5-{[4',6'-O-(4-pyridinemethylidene)-β-D-maltosyl]-oxy-methyl}-phenyl)-acetamide To a stirred solution of N-[2-chloro-5-(β-D-maltosyl-oxymethyl)-phenyl]-acetamide (0.500 g, 0.954 mmol) in DMF (25 mL) at rt was added 4-pyridinecarboxaldehyde (0.446 mL, 4.67 mmol) followed by concentrated $H_2SO_4$ (0.105 mL, 3.78 mmol). The reaction mixture was heated to 110° C. for 18 h. The reaction was then quenched with $K_2CO_3$ (1.40 g, 10.1 mmol) with an additional 0.5 h heating at 60° C. At this point, the solution was filtered hot, and the solvent was distilled off using the high vac. The residue was purified by flash chromatography (80:6:3 to 5:2:1 EtOAc:EtOH:H₂O gradient) to afford the product (0.050 g, 9%) as a yellow solid, mp >112° C. (decomp.); ¹H NMR (DMSO-d₆) δ2.07 (s, 3H), 3.05–3.13 (m, 1H), 3.27–3.49 (m, 4H), 3.49–3.62 (m, 3H), 3.66–3.75 (m, 3H), 4.14 (dd, J=12.5, 17.5 Hz, 1H), 4.29 (d, J=7.7 Hz, 1H), 4.67 (t, J=5.9 Hz, 1H), 4.67 (ABq, J=12.3 Hz, Δδ=0.22, 2H), 5.16 (d, J=3.7 Hz, 1H), 5.25 (d, J=5.3 Hz, 1H), 5.35 (d, J=4.8 Hz, 1H), 5.50 (d, J=3.3 Hz, 1H), 5.61–5.65 (m, 2H), 7.22 (dd, J=1.8, 8.3 Hz, 1H), 7.42–7.47 (m, 3H), 7.65 (s, 1H), 8.60 (d, J=5.9 Hz, 2H), 9.52 (s, 1H); IR (KBr) 3390, 2920, 2830, 1670, 1620, 1590, 1530, 1450, 1420, 1380, 1310, 1270, 1245, 1180, 1145, 1075, 1055, 1030, and 755 cm⁻¹; mass spectrum [(-) FAB], m/z 611 (M−H)⁻; Anal. Calcd. for $C_{27}H_{33}ClN_2O_{12} \cdot 4.25\ H_2O$: C, 47.03; H, 6.07; N, 4.06, Found: C, 46.63; H, 5.00; N, 3.60.

EXAMPLE 23

Benzoic acid 6-(3-acetylamino-4-chloro-benzoyloxy)-3-(7,8-dihydroxy-2-pyridin-4-yl-hexahydro-pyrano[3,2-d][1,3]dioxin-6-yloxy)-4,5-dihydroxy-tetrahydro-pyran-2-ylmethyl ester The title compound was prepared as a off-white solid (0.025 g, 46%) from N-(2-chloro-5-{[4',6'-O-(4-pyridinemethylidene)-β-D-maltosyl]-oxy-methyl}-phenyl)-acetamide using the procedure of Example 2, mp 260–261.5° C.; ¹H NMR (DMSO-d₆) δ2.04 (s, 3H), 3.15–3.22 (m, 1H), 3.25–3.43 (m, 2H), 3.51 (td, J=2.9, 8.8 Hz, 1H), 3.55–3.64 (m, 3H), 3.68–3.77 (m, 2H), 4.07 (dd, J=4.6, 9.7 Hz, 1H), 4.34 (dd, J=5.3, 12.3 Hz, 1H), 4.39 (d, J=7.7 Hz, 1H), 4.56–4.62 (m, 1H), 4.65 (ABq, J=12.3 Hz, Δδ=0.14, 2H), 5.15 (d, J=4.0 Hz, 1H), 5.35 (d, J=5.3 Hz, 1H), 5.39 (d, J=5.1 Hz, 1H), 5.56 (d, J=3.1 Hz, 1H), 5.58 (s, 1H), 5.79 (d, J=6.2 Hz, 1H), 7.18 (dd, J=2.0, 8.3 Hz, 1H), 7.38–7.45 (m, 3H), 7.53 (t, J=7.9 Hz, 2H), 7.62–7.68 (m, 2H), 7.97–8.01 (m, 2H), 8.59 (d, J=4.6 Hz, 2H), 9.49 (s, 1H); IR (KBr) 3460, 3310, 3240, 2910, 2830, 1725, 1665, 1620, 1590, 1530, 1420, 1375, 1275, 1140, 1075, 1055, 1030, and 715 cm⁻¹; mass spectrum [(+) FAB], m/z 717 (M+H)⁺, 739 (M+Na)⁺; Anal. Calcd. for $C_{34}H_{37}ClN_2O_{13} \cdot 1.5\ H_2O$: C, 54.88; H, 5.42; N, 3.76, Found: C, 54.55; H, 4.98; N, 3.68.

EXAMPLE 24

N-{5-[(4',6'-O-Benzylidene-β-D-maltosyloxy)-methyl]-2-chloro-phenyl}-acetamide

To a stirred solution of N-[2-chloro-5-(β-D-maltosyl-oxymethyl)-phenyl]-acetamide (14.15 g, 27.0 mmol) in DMF (325 mL) at rt was added benzaldehyde dimethyl acetal (8.11 mL, 54.0 mmol) dropwise followed by TsOH.H₂O (2.57 g, 13.5 mmol). The reaction mixture was heated to 60° C. for 6 h and then quenched with $K_2CO_3$ (1.87 g, 13.5 mmol) with an additional 0.5 h heating at this temperature. At this point, the solution was filtered hot, and the solvent was distilled off using the high vac. The residue was purified by flash chromatography (80:2:1 to 20:2:1 EtOAc:EtOH:H₂O gradient) to afford the product (10.8 g, 65%) as a white solid, mp 143–147° C.; ¹H NMR (DMSO-d₆) δ2.08 (s, 3H), 3.07–3.12 (m, 1H), 3.28–3.50 (m, 5H), 3.51–3.60 (m, 2H), 3.64–3.75 (m, 3H), 4.10–4.12 (m, 1H), 4.30 (d, J=7.9 Hz, 1H), 4.67 (t, 5.9 Hz, 1H), 4.68 (ABq, J=12.5 Hz, Δδ=0.22, 2H), 5.14 (d, J=4.0 Hz, 1H), 5.25 (d, J=5.1 Hz, 1H), 5.30 (d, J=5.3 Hz, 1H), 5.51 (d, J=3.3 Hz, 1H), 5.57 (s, 1H), 5.63 (d, J=6.8 Hz, 1H), 7.22 (dd, J=1.5, 8.3 Hz, 1H), 7.35–7.38 (m, 3H), 7.42–7.46 (m, 3H), 7.66 (s, 1H), 9.53 (s, 1H); IR (KBr) 3500, 3410, 2910, 2850, 1700, 1600, 1550, 1440, 1425, 1375, 1310, 1230, 1150, 1070, and 1030 cm⁻¹; mass spectrum [(+) FAB], m/z 634 (M+Na)⁺; Anal. Calcd. for $C_{28}H_{34}ClNO_{12} \cdot 1.0\ H_2O$: C, 53.38; H, 5.76; N, 2.22, Found: C, 53.58; H, 5.62; N, 2.25.

EXAMPLE 25

N-{5-[(4',6'-O-Benzylidene-2,2',3,3',6-penta-O-acetyl-β-D-maltosyl-oxy)-methyl]-2-chloro-phenyl}-acetamide To a stirred solution of N-{5-[(4',6'-O-benzylidene-β-D-maltosyloxy)-methyl]-2-chloro-phenyl}-acetamide (0.230 g, 0.376 mmol) and triethylamine (0.576 mL, 4.14 mmol) in DMF (5 mL) at rt was added dropwise acetic anhydride (0.195 mL, 2.07 mmol) followed by a catalytic amount of DMAP (0.023 g, 0.188 mmol). After 18 h, the mixture was concentrated, and the resulting residue was diluted with EtOAc (100 mL). This layer was washed with 1 N HCl (10 mL), sat. aq. NaHCO₃ (10 mL), and brine (10 mL) and then dried (Na₂SO₄). After concentration, the residue was purified by flash chromatography (10:90 to 80:20 EtOAc:petroleum ether gradient) to afford the product (0.181 g, 59%) as an off-white solid, mp 99–102° C.; ¹H NMR (DMSO-d₆) δ1.92 (s, 3H), 1.94 (s, 3H), 1.97 (s, 3H), 1.98 (s, 3H), 1.99 (s, 3H), 2.08 (s, 3H), 3.67–3.75 (m, 1H), 3.89 (t, J=9.4 Hz, 1H), 3.95–4.04 (m, 3H), 4.12–4.19 (m, 2H), 4.39 (dd, J=1.5, 11.9 Hz, 1H), 4.54 (d, J=12.7 Hz, 1H), 4.68–4.74 (m, 2H), 4.85–4.89 (m, 2H), 5.24 (t, J=10.1 Hz, 1H), 5.28 (d, J=4.0 Hz, 1H), 5.32 (d, J=9.4 Hz, 1H), 5.62 (s, 1H), 7.07 (dd, J=1.8, 8.1 Hz, 1H), 7.36 (s, 5H), 7.45 (d, J=8.3 Hz, 1H), 7.62 (s, 1H), 9.50 (s, 1H); IR (KBr) 3390, 2920, 2850, 1755, 1690, 1600, 1530, 1410, 1375, 1230, and 1050 cm⁻¹; mass spectrum [(+) FAB], m/z 822 (M+H)⁺, 844 (M+Na)⁺; Anal. Calcd. for $C_{38}H_{44}ClNO_{17} \cdot 1.0\ H_2O$: C, 54.32; H, 5.52; N, 1.67, Found: C, 54.68; H, 5.44; N, 1.57.

EXAMPLE 26

N-{5-[(6-O-Benzoyl-4',6'-O-benzylidene-β-D-maltosyl-oxy)-methyl]-2-chloro-phenyl}-acetamide The title compound was prepared as a white solid (4.04 g, 69%) from N-{5-[(4',6'-O-benzylidene-β-D-maltosyloxy)- methyl]-2-chloro-phenyl}-acetamide using a procedure similar to Example 2, mp 185–187° C.; $^1$H NMR (DMSO-$d_6$) δ2.05 (s, 3H), 3.16–3.22 (m, 1H), 3.32–3.42 (m, 2H), 3.48–3.64 (m, 4H), 3.71 (dd, J=4.8, 9.7 Hz, 1H), 3.74–3.79 (m, 1H), 4.05 (dd, J=4.8, 10.3 Hz, 1H), 4.35 (dd, J=5.3, 12.3 Hz, 1H), 4.39 (d, J=7.7 Hz, 1H), 4.58–4.63 (m, 1H), 4.65 (ABq, J=12.5 Hz, Δδ=0.14, 2H), 5.14 (d, 4.0 Hz, 1H), 5.34 (t, J=5.1 Hz, 2H), 5.52 (s, 1H), 5.57 (d, J=3.1 Hz, 1H), 5.79 (d, J=6.2 Hz, 1H), 7.19 (dd, J=2.0, 8.3 Hz, 1H), 7.32–7.38 (m, 3H), 7.38–7.45 (m, 3H), 7.51–7.55 (m, 2H), 7.63–7.68 (m, 2H), 7.98–8.01 (m, 2H), 9.49 (s, 1H); IR (KBr) 3380, 3290, 2890, 2870, 1730, 1670, 1600, 1540, 1440, 1420, 1375, 1275, 1070, 1050, 1025, 975, and 710 cm$^{-1}$; mass spectrum [(+) FAB], m/z 716/718 (M+H)$^+$, 738/740 (M+Na)$^+$; Anal. Calcd. for $C_{35}H_{38}ClNO_{13}$: C, 58.70; H, 5.35; N, 1.96, Found: C, 58.53; H, 5.36; N, 1.94.

EXAMPLE 27

(R)-N-[2-Chloro-5-[[[2,3-di-O-acetyl-6-O-benzoyl-4-O-[2,3-di-O-acetyl-4,6-O-(phenylmethylene)-β-D-glucopyranoysl]-β-D-glucopyranosyl]oxy]-methyl]-phenyl]acetamide The title compound was prepared as a glassy white solid (0.048 g, 86%) from N-{5-[(6-O-benzoyl-4',6'-O-benzylidene-β-D-maltosyl-oxy)-methyl]-2-chloro-phenyl}-acetamide using a procedure similar to Example 25, mp 101–104° C.; $^1$H NMR (DMSO-$d_6$) δ1.94 (s, 3H), 1.95 (s, 3H), 1.98 (s, 3H), 1.99 (s, 3H), 2.05 (s, 3H), 3.61 (t, J=9.7 Hz, 1H), 3.70–3.76 (m, 1H), 3.80 (dd, J=4.6 Hz, 1H), 3.86 (t, J=9.4 Hz, 1H), 4.13–4.22 (m, 2H), 4.46 (dd, J=3.7, 12.5 Hz, 1H), 4.64 (ABq, J=12.7 Hz, Δδ=0.14, 2H), 4.68 (d, J=10.5 Hz, 1H), 4.79 (dd, J=8.1, 9.4 Hz, 1H), 4.87–4.91 (m, 2H), 5.27 (t, J=9.9 Hz, 1H), 5.33–5.38 (m, 2H), 5.54 (s, 1H), 7.04 (dd, J=1.8, 8.1 Hz, 1H), 7.28–7.36 (m, 5H), 7.41 (d, J=8.3 Hz, 1H), 7.52–7.57 (m, 2H), 7.61 (s, 1H), 7.65–7.71 (m, 1H), 8.03–8.07 (m, 2H), 9.48 (s, 1H); IR (KBr) 3400, 2950, 2850, 1755, 1600, 1540, 1440, 1420, 1375, 1240, 1070, and 1030 cm$^{-1}$; mass spectrum [(+) FAB], m/z 884 (M+H)$^+$, 906 (M+Na)$^+$; Anal. Calcd. for $C_{43}H_{46}ClNO_{17}$: C, 58.41; H, 5.24; N, 1.58, Found: C, 58.24; H, 5.31; N, 1.59.

EXAMPLE 28

(R)-N-[2-Chloro-5-[[[6-O-(5-methoxy-1,5-dioxopentyl)-4-O-[4,6-O-(phenylmethylene)-α-D-glucopyranoysl]-β-D-gluconyranosyl]oxy]methyl]-phenyl]acetamide The title compound was prepared as a white foam (0.149 g, 50%) from N-{5-[(4',6'-O-benzylidene-β-D-maltosyloxy)-methyl]-2-chloro-phenyl}-acetamide using methyl-4-(chloroformyl)-butyrate as the acid chloride and a procedure similar to Example 2, mp 79–81° C.; $^1$H NMR (CDCl$_3$) δ1.90–1.98 (m, 2H), 2.13 (s, 3H), 2.35–2.43 (m, 4H), 3.41 (t, J=9.4 Hz, 1H), 3.47–3.73 (m, 6H), 3.65 (s, 3H), 3.82–3.89 (m, 2H), 3.93 (t, d=9.4 Hz, 1H), 4.06–4.26 (bs, 1H), 4.20 (dd, J=4.6, 12.3 Hz, 1H), 4.28 (q, J=5.1, 10.5 Hz, 1H), 4.34–4.40 (m, 2H), 4.70 (ABq, J=12.5 Hz, Δδ=0.23, 2H), 4.76–4.94 (bs, 1H), 5.04 (d, J=4.0 Hz, 1H), 5.20–5.36 (bs, 1H), 5.47 (s, 1H), 7.01 (dd, J=1.8, 8.6 Hz, 1H), 7.30 (d, J=8.3 Hz, 1H), 7.33–7.35 (m, 3H), 7.46–7.48 (m, 2H), 7.64 (s, 1H), 8.32 (s, 1H); IR (KBr) 3400, 2930, 2880, 1735, 1600, 1540, 1450, 1420, 1375, 1310, 1250, 1200, 1160, 1070, and 1025 cm$^{-1}$; mass spectrum [(+) FAB], m/z 740 (M+H)$^+$, 762 (M+Na)$^+$; Anal. Calcd. for $C_{34}H_{42}ClNO_{15}$.1.0 H$_2$O: C, 53.86; H, 5.85; N, 1.85, Found: C, 53.51; H, 5.80; N, 1.73.

EXAMPLE 29

4-Chloro-3-nitro-benzyl-4',6'-O-benyzlidene-β-D-maltoside

Step 1

4-Chloro-3-nitro-benzyl-β-D-maltoside

The title compound was prepared as a yellow powder (1.04 g, 97%) from 4-chloro-3-nitro-benzyl-β-D-maltoside heptaacetate using a procedure similar to step 4 of Example 1, mp 168–169° C.; $^1$H NMR (DMSO-$d_6$) δ3.03–3.13 (m, 2H), 3.20–3.38 (m, 4H), 3.41–3.49 (m, 3H), 3.55–3.64 (m, 2H), 3.68–3.75 (m, 1H), 4.00–5.50 (bs, 7H), 4.31 (d, J=7.7 Hz, 1H), 4.79 (ABq, J=13.6 Hz, Δδ=0.17, 2H), 5.00 (d, J=3.7 Hz, 1H), 7.70–7.78 (m, 2H), 8.09 (d, J=1.8 Hz, 1H); IR (KBr) 3380, 2900, 1720, 1625, 1550, 1365, 1140, 1080, and 1030 cm$^{-1}$; mass spectrum [(+) FAB], m/z 533/535 (M+Na)$^+$; Anal. Calcd. for $C_{19}H_{26}ClNO_{13}$.1.0 H$_2$O: C, 43.07; H, 5.33; N, 2.64, Found: C, 43.11; H, 5.23; N, 2.58.

Step 2

4-Chloro-3-nitro-benzyl-4',6'-O-benyzlidene-β-D-maltoside

The title compound was prepared as a yellow solid (0.869 g, 74%) from 4-chloro-3-nitro-benzyl-β-D-maltoside using a procedure similar to Example 24, mp >122° C. (decomp.); $^1$H NMR (DMSO-$d_6$) δ3.11 (dd, J=4.8, 8.8 Hz, 1H), 3.30–3.42 (m, 4H), 3.46 (dd, J=3.3, 9.0 Hz, 1H), 3.49–3.60 (m, 2H), 3.64–3.75 (m, 3H), 4.12 (dd, J=2.9, 8.1 Hz, 1H), 4.33 (d, J=7.7 Hz, 1H), 4.65 (t, J=5.7 Hz, 1H), 4.80 (ABq, J=13.6 Hz, Δδ=0.16, 2H), 5.14 (d, J=4.0 Hz, 1H), 5.29 (d, J=5.1 Hz, 1H), 5.34 (d, J=5.1 Hz, 1H), 5.53 (d, J=3.1 Hz, 1H), 5.57 (s, 1H), 5.62 (d, J=6.6 Hz, 1H), 7.34–7.38 (m, 3H), 7.42–7.46 (m, 2H), 7.70–7.77 (m, 2H), 8.10 (d, J=1.6 Hz, 1H); IR (KBr) 3390, 2920, 2870, 1625, 1610, 1590, 1550, 1440, 1420, 1360, 1200, 1140, 1070, and 1030 cm$^{-1}$; mass spectrum [(+) FAB], m/z 600/602 (M+H)$^+$, 622/624 (M+Na)$^+$; Anal. Calcd. for $C_{26}H_{30}ClNO_{13}$.0.5 H$_2$O: C, 51.28; H, 5.13; N, 2.30, Found: C, 51.13; H, 5.21; N, 2.30.

EXAMPLE 30

4-Chloro-3-nitro-benzyl-6-O-benzoyl-4',6'-O-benzylidene-β-D-maltoside

The title compound was prepared as a off-white glass (0.155 g, 49%) from 4-chloro-3-nitro-benzyl-4',6'-O-benyzlidene-β-D-maltoside using a procedure similar to Example 2, mp 111–114° C.; $^1$H NMR (DMSO-$d_6$) δ3.19–3.26 (m, 1H), 3.28–3.43 (m, 2H), 3.51–3.65 (m, 4H), 3.68–3.75 (m, 1H), 3.77–3.81 (m, 1H), 4.04 (dd, J=4.6, 9.9 Hz, 1H), 4.34 (dd, J=5.1, 12.3 Hz, 1H), 4.45 (d, J=7.9 Hz, 1H), 4.59 (d, J=12.3 Hz, 1H), 4.79 (ABq, J=13.6 Hz, Δδ=0.10, 2H), 5.14 (d, J=3.7 Hz, 1H), 5.35 (d, J=5.3 Hz, 1H), 5.46 (d, J=5.1 Hz, 1H), 5.52 (s, 1H), 5.60 (d, J=3.1 Hz, 1H), 5.80 (d, J=6.2 Hz, 1H), 7.33–7.37 (m, 3H), 7.39–7.43 (m, 2H), 7.50–7.55 (m, 2H), 7.63–7.68 (m, 1H), 7.68–7.73 (m, 2H), 7.97 (dd, J=1.1, 8.1 Hz, 2H), 8.08 (s, 1H); IR (KBr) 3400, 2910, 2860, 1725, 1610, 1540, 1440, 1360, 1325, 1275, 1070, and 1025 cm$^{-1}$; mass spectrum [(+) FAB], m/z 704 (M+H)$^+$, 726 (M+Na)$^+$; Anal. Calcd. for $C_{33}H_{34}ClNO_{14}$.1.0 H$_2$O: C, 54.89; H, 5.03; N, 1.94, Found: C, 54.72; H, 4.56; N, 1.91.

EXAMPLE 31

(R)-(4-Chloro-3-nitrophenyl)methyl-2,3-di-O-acetyl-6-O-benzoyl-4-O-[2,3-di-O-acetyl-4,6-O-(phenylmethylene)-α-D-glucopyranosyl]-β-D-glucopyranoside The title compound was prepared as a off-white solid (0.0773 g, 84%) from 4-chloro-3-nitro-benzyl-6-O-benzoyl- 4',6'-O-benzylidene-β-D-maltoside using a procedure similar to Example 25, mp 138–140° C.; $^1$H NMR (DMSO-$d_6$) δ1.95 (s, 3H), 1.96 (s, 3H), 1.98 (s, 3H), 1.99 (s, 3H), 3.61 (t, J=9.4 Hz, 1H), 3.69–3.77 (m, 1H), 3.79 (dd, J=4.6, 9.4 Hz, 1H), 3.86 (t, J=9.4 Hz, 1H), 4.13–4.25 (m, 2H), 4.44 (dd, J=3.5, 12.3 Hz, 1H), 4.66–4.69 (m, 1H), 4.71 (d, J=13.6 Hz, 1H), 4.80–4.84 (m, 2H), 4.89 (dd, J=4.2, 10.3 Hz, 1H), 4.96 (d, J=7.9 Hz, 1H), 5.27 (t, J=9.9 Hz, 1H), 5.34–5.40 (m, 2H), 5.54 (s, 1H), 7.27–7.37 (m, 5H), 7.51–7.56 (m 2H), 7.57 (dd, J=2.0, 8.3 Hz, 1H), 7.65–7.70 (m, 1H), 7.72 (d, J=8.3 Hz, 1H), 7.93 (d, J=2.0 Hz, 1H), 8.01–8.05 (m, 2H); IR (KBr) 3440, 2950, 2830, 1755, 1620, 1550, 1440, 1410, 1370, 1320, 1240, 1160, 1120, 1070, 1030, and 990 cm$^{-1}$; mass spectrum [(+) FAB], m/z 872 (M+H)$^+$, 894 (M+Na)$^+$; Anal. Calcd. for $C_{41}H_{42}ClNO_{18} \cdot 0.5\ H_2O$: C, 55.88; H, 4.92; N, 1.59, Found: C, 55.90; H, 4.80; N, 1.56.

EXAMPLE 32

Nicotinic acid 6-(4-chloro-3-nitro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester The title compound was prepared as a white foam (0.211 g, 45%) from 4-chloro-3-nitro-benzyl-4',6'-O-benzylidene-β-D-maltoside using nicotinoyl chloride hydrochloride and a procedure similar to Example 2 (except compound purified directly with flash chromatography), mp >105° C. (decomp.); $^1$H NMR (DMSO-$d_6$) δ3.21–3.28 (m, 1H), 3.32–3.42 (m, 2H), 3.51–3.60 (m, 3H), 3.65 (t, J=9.2 Hz, 1H), 3.67–3.74 (m, 1H), 3.78–3.83 (m, 1H), 4.01–4.06 (m, 1H), 4.38 (dd, J=5.1, 12.3 Hz, 1H), 4.45 (d, J=7.9 Hz, 1H), 4.58–4.64 (m, 1H), 4.79 (ABq, J=13.6 Hz, Δδ=0.09, 2H), 5.17 (d, J=3.7 Hz, 1H), 5.35 (d, J=5.3 Hz, 1H), 5.46 (d, J=5.3 Hz, 1H), 5.52 (s, 1H), 5.61 (d, J=3.1 Hz, 1H), 5.82 (d, J=6.2 Hz, 1H), 7.34–7.37 (m, 3H), 7.39–7.43 (m, 2H), 7.54–7.59 (m, 1H), 7.68–7.71 (m, 2H), 8.08 (d, J=1.3 Hz, 1H), 8.31 (d, J=7.9 Hz, 1H), 8.78–8.88 (bs, 1H), 9.05–9.19 (bs, 1H); IR (KBr) 3400, 2900, 2870, 1725, 1600, 1540, 1440, 1410, 1360, 1285, 1070, 1030, 740, and 690 cm$^{-1}$; mass spectrum [(+) FAB], m/z 705/707 (M+H)$^+$; Anal. Calcd. for $C_{32}H_{33}ClN_2O_{14} \cdot 1.0\ H_2O$: C, 53.15; H, 4.88; N, 3.87, Found: C, 53.33; H, 4.78; N, 3.72.

EXAMPLE 33

(R)-(4-Chloro-3-nitrophenyl)methyl 4-[2,3-di-O-acetyl-4,6-O-(phenylmethylene)-α-D-glucopyranosyl]-β-D-glucopyranoside 2,3-diacetate 6-(3-pyridinecarboxylate)

The title compound was prepared as a white foam (0.123 g, 95%) from nicotinic acid 6-(4-chloro-3-nitro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester using a procedure similar to Example 25, mp >101° C. (decomp.); $^1$H NMR (DMSO-$d_6$) δ1.95 (s, 3H), 1.96 (s, 3H), 1.98 (s, 3H), 1.99 (s, 3H), 3.64 (t, J=9.4 Hz, 1H), 3.69–3.81 (m, 2H), 3.87 (t, J=9.4 Hz, 1H), 4.17 (dd, J=3.1, 5.7 Hz, 1H), 4.27 (t, J=9.4 Hz, 1H), 4.47 (dd, J=4.0, 12.5 Hz, 1H), 4.69–4.75 (m, 2H), 4.80–4.91 (m, 3H), 4.96 (d, J=8.1 Hz, 1H), 5.26 (t, J=10.1 Hz, 1H), 5.33–5.39 (m, 2H), 5.55 (s, 1H), 7.29–7.36 (m, 5H), 7.55–7.59 (m, 2H), 7.72 (d, J=8.3 Hz, 1H), 7.93 (d, J=2.0 Hz, 1H), 8.36 (dt, J=2.2, 7.9 Hz, 1H), 8.84 (dd, J=1.8, 4.8 Hz, 1H), 9.16 (dd, J=0.9, 2.2 Hz, 1H); IR (KBr) 3440, 2930, 2860, 1755, 1600, 1540, 1420, 1375, 1280, 1240, 1140, 1070, 1060, 1030, and 995 cm$^{-1}$; mass spectrum [(+) FAB], m/z 873/875 (M+H)$^+$, 895/897 (M+Na)$^+$; Anal. Calcd. for $C_{40}H_{41}ClN_2O_{18} \cdot 1.25\ H_2O$: C, 53.64; H, 4.89; N, 3.13, Found: C, 53.46; H, 4.51; N, 2.96.

EXAMPLE 34

4-Methoxy-benzoic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester The title compound was prepared as a white foam (0.284 g, 47%) from N-{5-[(4',6'-O-benzylidene-β-D-maltosyloxy)-methyl]-2-chloro-phenyl}-acetamide using p-anisoyl chloride and a procedure similar to Example 2, mp >117° C. (decomp.); $^1$H NMR (DMSO-$d_6$) δ2.05 (s, 3H), 3.15–3.21 (m, 1H), 3.35 (d, J=9.4 Hz, 1H), 3.35–3.42 (m, 1H), 3.48–3.61 (m, 4H), 3.67–3.76 (m, 2H), 3.82 (s, 3H), 4.05 (dd, J=4.8, 9.9 Hz, 1H), 4.29 (dd, J=5.5, 12.3 Hz, 1H), 4.38 (d, J=7.9 Hz, 1H), 4.55–4.60 (m, 1H), 4.65 (ABq, J=12.5 Hz, Δδ=0.14, 2H), 5.13 (d, J=3.7 Hz, 1H), 5.34 (dd, J=4.0, 5.3 Hz, 2H), 5.52 (s, 1H), 5.56 (d, J=2.9 Hz, 1H), 5.77 (d, J=6.2 Hz, 1H), 7.02–7.06 (m, 2H), 7.19 (dd, J=2.0, 8.3 Hz, 1H), 7.33–7.37 (m, 3H), 7.39–7.44 (m, 3H), 7.64 (s, 1H), 7.94 (dt, J=2.9, 9.9 Hz, 2H), 9.50 (s, 1H); IR (KBr) 3410, 3000, 2910, 2880, 1720, 1610, 1580, 1530, 1515, 1450, 1420, 1375, 1255, 1160, 1070, and 1025 cm$^{-1}$; mass spectrum [(+) FAB], m/z 746/748 (M+H)$^+$, 768/770 (M+Na)$^+$, 784/786 (M+K)$^+$; Anal. Calcd. for $C_{36}H_{40}ClNO_{14} \cdot 2.0\ H_2O$: C, 55.28; H, 5.67; N, 1.79, Found: C, 55.38; H, 5.28; N, 1.72.

EXAMPLE 35

4-Methoxy-benzoic acid 4,5-diacetoxy-6-(3-acetylamino-4-chloro-benzyloxy)-3-(7,8-diacetoxy-2-phenyl-hexahydro-pyrano[3,2-d][1,3]dioxin-6-yloxy)-tetrahydro-pyran-2-ylmethyl ester The title compound was prepared as a white foam (0.142 g, 81%) from 4-methoxy-benzoic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester using a procedure similar to Example 25, mp >110° C. (decomp.); $^1$H NMR (DMSO-$d_6$) δ1.94 (s, 3H), 1.95 (s, 3H), 1.98 (s, 3H), 1.99 (s, 3H), 2.06 (s, 3H), 3.61 (t, J=9.7 Hz, 1H), 3.68–3.75 (m, 1H), 3.80 (dd, J=4.6, 9.4 Hz, 1H), 3.82 (s, 3H), 3.82–3.89 (m, 1H), 4.11–4.16 (m, 1H), 4.17 (q, 9.7 Hz, 1H), 4.40 (dd, J=3.3, 12.3 Hz, 1H), 4.63 (ABq, J=12.7 Hz, Δδ=0.15, 2H), 4.64 (d, J=10.8 Hz, 1H), 4.77 (dd, J=7.9, 9.4 Hz, 1H), 4.86–4.91 (m, 2H), 5.26 (t, J=9.9 Hz, 1H), 5.32–5.38 (m, 2H), 5.54 (s, 1H), 7.06 (dt, J=2.9, 9.7 Hz, 3H), 7.29–7.37 (m, 5H), 7.42 (d, J=8.1 Hz, 1H), 7.61 (s, 1H), 7.99 (dt, J=2.9, 9.9 Hz, 2H), 9.4 (s, 1H); IR (KBr) 3400, 2950, 2840, 1755, 1700, 1600, 1580, 1535, 1515, 1450, 1420, 1375, 1240, 1165, 1110, 1070, 1055, and 1030 cm$^{-1}$; mass spectrum [(+) FAB], m/z 914/916 (M+H)$^+$, 936/938 (M+Na)$^+$; Anal. Calcd. for $C_{44}H_{48}ClNO_{18} \cdot 1.0\ H_2O$: C, 56.68; H, 5.41; N, 1.50, Found: C, 56.37; H, 5.08; N, 1.48.

EXAMPLE 36

4-Chloro-benzoic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester The title compound was prepared as a white foam (0.372 g, 61%) from N-{5-[(4',6'-O-benzylidene-β-D- maltosyloxy)-methyl]-2-chloro-phenyl}-acetamide using 4-chlorobenzoyl chloride and a procedure similar to Example 2, mp >113° C. (decomp.); $^1$H NMR (DMSO-$d_6$) δ2.05 (s, 3H), 3.16–3.21 (m, 1H), 3.28–3.41 (m, 2H), 3.48–3.62 (m, 4H), 3.69 (dd, J=5.1, 9.9 Hz, 1H), 3.76 (ddd, J=1.5, 4.6, 9.4 Hz, 1H), 4.04 (dd, J=4.8, 9.9 Hz, 1H), 4.33–4.40 (m, 2H), 4.55–4.60 (m, 2H), 4.73 (d, J=12.5 Hz, 1H), 5.13 (d, J=4.0 Hz, 1H), 5.35 (t, J=5.3 Hz, 2H), 5.52 (s, 1H), 5.58 (d, J=2.9 Hz, 1H), 5.81 (d, J=6.2 Hz, 1H), 7.19 (dd, J=2.0, 8.3 Hz, 1H), 7.33–7.37 (m, 3H), 7.38–7.43 (m, 3H), 7.59 (dt, J=2.4, 9.2 Hz, 2H), 7.64 (s, 1H), 7.99 (dt, J=2.4, 9.0 Hz, 2H), 9.50 (s, 1H); IR (KBr) 3410, 2910, 2870, 1725, 1590, 1530, 1440, 1420, 1375, 1270, 1070, 1025, and 760 cm$^{-1}$; mass spectrum [(+) FAB], m/z 750/752/754 (M+H)$^+$, 772 (M+Na)$^+$, 788/790/792 (M+K)$^+$; Anal. Calcd. for $C_{35}H_{37}Cl_2NO_{13}$.1.5 $H_2O$: C, 54.06; H, 5.18; N, 1.80, Found: C, 53.76; H, 4.78; N, 1.77.

EXAMPLE 37

4-Chloro-benzoic acid 4,5-diacetoxy-6-(3-acetylamino-4-chloro-benzyloxy)-3-(7,8-diacetoxy-2-phenyl-hexahydro-pyrano[3,2-d][1,3]dioxin-6-yloxy)-tetrahydro-pyran-2-ylmethyl ester The title compound was prepared as a white foam (0.225 g, 72%) from 4-chloro-benzoic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester using a procedure similar to Example 25, mp 114–115° C.; $^1$H NMR (DMSO-$d_6$) δ1.94 (s, 3H), 1.95 (s, 3H), 1.98 (s, 3H), 1.99 (s, 3H), 2.05 (s, 3H), 3.62 (t, J=9.2 Hz, 1H), 3.68–3.74 (m, 1H), 3.79 (dd, J=4.2, 9.2 Hz, 1H), 3.86 (t, J=9.4 Hz, 1H), 4.13–4.19 (m, 1H), 4.18 (q, J=9.4, 1H), 4.47 (dd, J=3.5, 12.3 Hz, 1H), 4.63 (ABq, J=12.7 Hz, Δδ=0.14, 2H), 4.66 (d, J=10.8 Hz, 1H), 4.79 (dd, J=8.1, 9.2 Hz, 1H), 4.86–4.91 (m, 2H), 5.26 (t, J=9.9 Hz, 1H), 5.32–5.38 (m, 2H), 5.54 (s, 1H), 7.05 (dd, J=1.8, 8.3 Hz, 1H), 7.27–7.31 (m, 2H), 7.32–7.36 (m, 3H), 7.42 (d, J=8.3 Hz, 1H), 7.58–7.63 (m, 3H), 8.02–8.06 (m, 2H), 9.49 (s, 1H); IR (KBr) 3410, 2950, 2860, 1755, 1690, 1600, 1530, 1450, 1420, 1375, 1260, 1140, 1070, 1055, and 1030 cm$^{-1}$; mass spectrum [(+) FAB], m/z 918/920/922 (M+H)$^+$, 940/942/944 (M+Na)$^+$; Anal. Calcd. for $C_{43}H_{45}Cl_2NO_{17}$.1.0 $H_2O$: C, 55.13; H, 5.06; N, 1.50, Found: C, 54.77; H, 4.73; N, 1.45.

EXAMPLE 38

(R)-N-[2-Chloro-5-[[[6-O-(4-chloro-3-nitrobenzoyl)-4-O-[4,6O-(phenylmethylene)-α-D-glucopyranosyl]-β-D-glucopyranosyl]oxy]methyl]phenyl]acetamide The title compound was prepared as a white solid (0.158 g, 52%) from N-{5-[(4',6'-O-benzylidene-β-D-maltosyloxy)-methyl]-2-chloro-phenyl}-acetamide using 4-chloro-3-nitrobenzoyl chloride and a procedure similar to Example 2; $^1$H NMR (DMSO-$d_6$) δ2.13 (s, 3H), 3.41 (apparant t, J=9.4 Hz, 1H), 3.55–3.69 (m, 6H), 3.77 (apparant t, J=9.0 Hz, 1H), 3.87–3.97 (m, 3H), 4.29 (dd, J=10.5, 4.8 Hz, 1H), 4.41 (d, J=7.7 Hz, 1H), 4.47 (dd, J=12.1, 5.3 Hz, 1H), 4.60 (d, J=12.7 Hz, 2H), 4.72 (dd, J=12.0, 2.0 Hz, 1H), 4.84 (d, J=12.5 Hz, 1H), 5.08 (d, J=3.7 Hz, 1H), 5.14 (bs, 1H), 5.47 (s, 1H), 6.99 (dd, J=8.3, 2.0 Hz, 1H), 7.29 (d, J=8.3 Hz, 1H), 7.32– 7.44 (m, 3H), 7.45–7.47 (m, 2H), 7.60 (s, 1H), 7.64 (d, J=8.6 Hz, 1H), 8.16 (dd, J=8.3, 2.0 Hz, 1H), 8.34 (s, 1H), 8.51 (d, J=2.0 Hz, 1H); IR (KBr) 3400, 2900, 1750, 1660, 1275 and 1075 cm$^{-1}$; mass spectrum [(+) FAB], m/z 795/797/799 (M+H)$^+$, 817/819/821 (M+Na)$^+$; Anal. Calcd. for $C_{35}H_{36}Cl_2N_2O_{15}$.1.0 $H_2O$: C, 51.67; H, 4.71; N, 3.44, Found: C, 51.87; H, 4.84; N, 3.60.

EXAMPLE 39

N-{5-[(2,2',3,-Tri-O-Acetyl-6-O-(4-chloro-3-nitrobenzoyl)-4',6'-O-(benzylidene)-β-D-maltosyl)-oxymethyl]-2-chloro-phenyl)-acetamide The title compound was prepared as a white solid from (R)-N-[2-chloro-5-[[[6-O-(4-chloro-3-nitrobenzoyl)-4-O-[4,6O-(phenylmethylene)-α-D-glucopyranosyl]-β-D-glucopyranosyl]oxy]methyl]phenyl]acetamide using a procedure similar to Example 25; $^1$H NMR (CDCl$_3$) δ2.04 (s, 3H), 2.05 (s, 3H), 2.06 (s, 3H), 2.22 (s, 3H), 3.11 (d, J=3.7 Hz, 1H), 3.62 (m, 4H), 3.81–3.99 (m, 2H), 4.29 (dd, J=10.3, 4.8 Hz, 1H), 4.48–4.61 (m, 3H), 4.98 (dd, J=10.3, 3.7 Hz, 1H), 5.35 (d, J=4.0 Hz, 1H), 5.44–5.52 (m, 2H), 6.99 (dd, J=8.1, 2.0 Hz, 1H), 7.31–7.42 (m, 6H), 7.58–7.59 (m, 2H), 7.63 (d, J=8.3 Hz, 1H), 8.14 (dd, J=8.3, 2.0 Hz, 1H), 8.31 (bs, 1H), 8.51 (d, J=2.0 Hz, 1H); IR (KBr) 3400, 2900, 1750, 1660, 1275 and 1075 cm$^{-1}$; mass spectrum [(+) FAB], m/z 921/923/925 (M+H)$^+$, 943/945/947 (M+Na)$^+$; Anal. Calcd. for $C_{41}H_{42}Cl_2N_2O_{18}$: C, 53.43; H, 4.59; N, 3.04, Found: C, 52.88; H, 5.11; N, 2.59.

EXAMPLE 40

(R)-N-[2-Chloro-5-[[[6-O-(4-cyanobenzoyl)-4-O-[4,6O-(phenylmethylene)-α-D-glucopyranosyl]-β-D-glucopyranosyl]oxy]methyl]phenyl]acetamide The title compound was prepared as a white solid from N-{5-[(4',6'-O-benzylidene-β-D-maltosyloxy)-methyl]-2-chloro-phenyl}-acetamide using 4-cyanobenzoyl chloride and a procedure similar to Example 2, mp 143–145° C.; $^1$H NMR (DMSO-$d_6$) δ2.04 (s, 3H), 3.17–3.22 (m, 2H), 3.28–3.41 (m, 3H), 3.48–3.80 (m, 5H), 4.03 (dd, J=9.4, 5.1 Hz, 1H), 4.38–4.42 (m, 2H), 4.62 (d, J=10.8 Hz, 1H), 4.65 (ABq, J=12.5 Hz, Δδ=0.13, 2H), 5.14 (d, J=4.80 Hz, 2H), 5.35 (apparant t, J=5.3 Hz, 2H), 5.52 (s, 1H), 5.59 (d, J=2.9 Hz, 1H), 5.83 (d, J=6.0 Hz, 1H), 7.19 (dd, J=8.3, 2.0 Hz, 1H), 7.34–7.39 (m, 3H), 7.39–7.42 (m, 2H), 7.63 (s, 1H), 8.0 (d, J=8.8 Hz, 2H), 8.13 (d, J=8.8 Hz, 2H), 9.49 (s, 1H); IR (KBr) 3400, 2900, 1725, 1660, 1275 and 1075 cm$^{-1}$; mass spectrum [(−) FAB], m/z 739/741 (M−H)$^-$; Anal. Calcd. for $C_{36}H_{37}ClN_2O_{13}$.0.5 $H_2O$: C, 57.64; H, 5.11; N, 3.73, Found: C, 57.47; H, 5.08; N, 3.57.

EXAMPLE 41

(R)-N-[2-Chloro-5-[[[6-O-(4-nitrobenzoyl)-4-O-[4,6O-(phenylmethylene)-α-D-glucopyranosyl]-β-D-glucopyranosyl]oxy]methyl]phenyl]acetamide The title compound was prepared as a white solid from N-{5-[(4',6'-O-benzylidene-β-D-maltosyloxy)-methyl]-2-chloro-phenyl}-acetamide using 4-nitrobenzoyl chloride and a procedure similar to Example 2; $^1$H NMR (CDCl$_3$) δ2.14 (s, 3H), 3.41 (apparant t, J=9.2 Hz, 1H), 3.54–3.69 (m, 5H), 3.84–3.99 (m, 5H), 4.30 (dd, J=10.1, 5.1 Hz, 1H), 4.41 (d, J=7.7 Hz, 1H), 4.50 (dd, J=7.5, 4.6 Hz, 2H), 4.72 (dd, J=12.1, 1.3 Hz, 1H), 4.73 (ABq, J=12.5 Hz, Δδ=0.21, 2H), 4.85 (d, J=3.4 Hz, 2H), 5.47 (s, 1H), 6.97–7.0 (m, 1H), 7.29 (d, J=2.9 Hz, 1H), 7.32–7.36 (m, 3H), 7.44–7.52 (m, 2H), 7.60 (bs, 1H), 8.20 (d, J=9.0 Hz, 2H), 8.29 (d, J=9.0 Hz, 2H), 8.36 (bs, 1H); IR (KBr) 3400, 2900, 1725, 1660, 1275 and 1075 cm$^-$; mass spectrum [(+) FAB], m/z 761/763 (M+H)$^+$, 783/785 (M+Na)$^+$; Anal. Calcd. for $C_{35}H_{37}ClN_2O_{15}$.2.0 $H_2O$: C, 52.74; H, 5.18; N, 3.51, Found: C, 52.92; H, 5.07; N, 3.45.

EXAMPLE 42

(R)-N-[2-Chloro-5-[[[6-O-(3-trifluoromethylbenzoyl)-4-O-[4,6O-(phenyl-methylene)-α-D-glucopyranosyl]-β-D-glucopyranosyl]oxy]methyl]phenyl]acetamide The title compound was prepared as a white solid from N-{5-[(4',6'-O-benzylidene-β-D-maltosyloxy)-methyl]-2-chloro-phenyl}-acetamide using 3-trifluoromethylbenzoyl chloride and a procedure similar to Example 2, mp 194° C.; $^1$H NMR (CDCl$_3$) δ2.11 (s, 3H), 3.40 (apparant t, J=9.4 Hz, 1H), 3.53–3.68 (m, 5H), 3.77 (apparant t, J=8.8 Hz, 1H), 3.88–3.93 (m, 2H), 3.97 (apparant t, J=9.4 Hz, 1H), 4.30 (dd, J=10.3, 5.1 Hz, 1H), 4.40 (d, J=7.7 Hz, 1), 4.71 (ABq, J=12.5 Hz, Δδ=0.22, 2H), 4.73 (d, J=11, Hz, 1H), 5.08 (d, J=3.7 Hz, 2H), 5.46 (s, 1H), 6.95 (dd, J=8.34, 1.8 Hz, 1H), 7.26 (d, J=8.3, Hz, 1H), 7.30–7.34 (m, 3H), 7.43–7.47 (m, 2H), 7.60 (bt, 7 Hz, 2H), 7.81 (bd, J=7.7 Hz, 1H), 8.22 (bd, J=8.0 Hz, 1H), 8.32 (bd, J=9.2 Hz, 2H); IR (KBr) 3400, 2900, 1725, 1660, 1250 and 1075 cm$^{-1}$; mass spectrum [(+) FAB], m/z 784/786 (M+H)$^+$, 806/808 (M+Na)$^+$; Anal. Calcd. for C$_{36}$H$_{39}$ClNF$_3$O$_{13}$·1.0 H$_2$O: C, 53.91; H, 4.90; N, 1.75, Found: C, 54.19; H, 4.67; N, 1.75.

EXAMPLE 43

N-{5-[(4',6'-O-Benzylidene-6-O-(2-iodo)-benzoyl-β-D-maltosyl)-oxy-methyl]-2-chloro-phenyl)-acetamide The title compound was prepared as a white solid from N-{5-[(4',6'-O-benzylidene-β-D-maltosyloxy)-methyl]-2-chloro-phenyl}-acetamide using o-iodobenzoyl chloride and a procedure similar to Example 2, mp 140–143° C.; $^1$H NMR (DMSO-d$_6$) δ2.05 (s, 3H), 3.15–3.17 (m, 1H), 3.28–3.65 (m, 6H), 3.75–3.79 (m, 3H), 4.14 (dd, J=9.1 Hz, 1H), 4.35 (dd, J=12.1, 5.7 Hz, 1H), 4.40 (d, J=7.9 Hz, 1H), 4.62 (d, J=10.8, Hz, 1H), 4.66 (ABq, J=12.3 Hz, Δδ=0.14, 2H), 5.15 (d, J=4.0 Hz, 1H), 5.36 (t, J=5.3 Hz, 2H), 5.55 (s, 1H), 5.60 (d, J=2.64 Hz, 1H), 5.87 (d, J=6.2 Hz, 1H), 7.18 (dd, J=8.1, 2.00 Hz, 1H), 7.26–7.30 (m, 1H), 7.34–7.50 (m, 6H), 7.51–7.53 (m, 1H), 7.63 (s, 1H), 7.78 (dd, J=7.9, 1.5 Hz, 1H), 8.02 (dd, J=7.9, 1.1 Hz, 1H), 9.50 (s, 1H); IR (KBr) 3400, 2930, 1750, 1550, 1245 and 1075 cm$^{-1}$; mass spectrum [(+) ESI], m/z 842/844 (M+H)$^+$, 859/861 (M+NH$_4$)$^+$; Anal. Calcd. for C$_{35}$H$_{37}$ClNO$_{13}$·1.0 H$_2$O: C, 48.84; H, 4.53; N, 1.66, Found: C,48.59.; H, 4.28; N, 1.58.

EXAMPLE 44

N-{5-[(4',6'-O-Benzylidene-6-O-(3-iodo)-benzoyl-β-D-maltosyl)-oxy-methyl]-2-chloro-phenyl}-acetamide The title compound was prepared as a white solid from N-{5-[(4',6'-O-benzylidene-β-D-maltosyloxy)-methyl]-2-chloro-phenyl}-acetamide using m-iodobenzoyl chloride and a procedure similar to Example 2, mp 175–177° C.; $^1$H NMR (DMSO-d$_6$) δ2.05 (s, 3H), 3.15–3.20 (m, 2H), 3.32–3.42 (m, 2H), 3.50–3.61 (m, 4H), 3.70–3.77 (m, 2H), 4.00–4.09 (m, 2H), 4.34 (dd, J=12.1, 5.7 Hz, 1H), 4.40 (d, J=7.9 Hz, 1H), 4.62 (d, J=10.5, Hz, 1H), 4.66 (ABq, J=12.3 Hz, Δδ=0.14, 2H), 5.14 (d, J=4.0 Hz, 1H), 5.35 (apparant t, J=5.7 Hz, 2H), 5.53 (s, 1H), 5.57 (d, J=2.9 Hz, 1H), 5.79 (d, J=6.4 Hz, 1H), 7.01 (dd, J=8.3, 1.8 Hz, 1H), 7.32–7.37 (m, 3H), 7.40–7.42 (m, 2H), 7.65 (s, 1H), 7.99–8.03 (m, 2H), 8.26 (t, J=1.8 Hz, 1H), 9.50 (s, 1H); IR (KBr) 3400, 2930, 1700, 1250 and 1075 cm$^{-1}$; mass spectrum [(−) FAB], m/z 840 (M–H)$^-$; Anal. Calcd. for C$_{35}$H$_{37}$ClNO$_{13}$·1.0 H$_2$O: C, 48.88; H, 4.57; N, 1.63, Found: C, 49.02; H, 4.49; N, 1.54.

EXAMPLE 45

N-{5-[(4',6'-O-Benzylidene-6-(4-iodo-benzoyl)-oxy-β-D-maltosyl)-oxy-methyl]-2-chloro-phenyl}-acetamide The title compound was prepared as a white solid (0.410 g, 60%) from N-{5-[(4',6'-O-benzylidene-β-D-maltosyloxy)-methyl]-2-chloro-phenyl}-acetamide using p-iodobenzoyl chloride and a procedure similar to Example 2, mp >187° C. (decomp.); $^1$H NMR (DMSO-d$_6$) δ2.05 (s, 3H), 3.15–3.22 (m, 1H), 3.28–3.42 (m, 2H), 3.48–3.62 (m, 4H), 3.66–3.73 (m, 1H), 3.75 (ddd, J=1.5, 4.8, 9.7 Hz, 1H), 4.01–4.06 (m, 1H), 4.35 (dd, J=5.3, 12.3 Hz, 1H), 4.39 (d, J=7.7 Hz, 1H), 4.57 (d, J=10.3 Hz, 1H), 4.65 (ABq, J=12.5 Hz, Δδ=0.14, 2H), 5.12 (d, J=4.0 Hz, 1H), 5.35 (t, J=5.3 Hz, 2H), 5.52 (s, 1H), 5.58 (d, J=2.9 Hz, 1H), 5.81 (d, J=6.2 Hz, 1H), 7.19 (dd, J=1.8, 8.1 Hz, 1H), 7.33–7.38 (m, 3H), 7.38–7.43 (m, 3H), 7.64 (s, 1H), 7.73 (dt, J=2.0, 8.8 Hz, 2H), 7.91 (dt, J=2.2, 8.8 Hz, 2H), 9.50 (s, 1H); IR (KBr) 3420, 3270, 2920, 2880, 1725, 1660, 1590, 1530, 1450, 1425, 1385, 1375, 1280, 1140, 1110, 1070, 1050, 1030, 1005, and 750 cm$^{-1}$; mass spectrum [(+) FAB], m/z 864/866 (M+Na)$^+$; Anal. Calcd. for C$_{35}$H$_{37}$ClNO$_{13}$: C, 49.93; H, 4.43; N, 1.66, Found: C, 49.65; H, 4.51; N, 1.77.

EXAMPLE 46

(R)-N-[-2-Chloro-5-[[[6-O-(phenylacetyl)-4-O-[4,6-O-(phenylmethylene)-α-D-glucopyranosyl]-β-D-glucopyranosyl]oxy]methyl]phenyl]acetamide The title compound was prepared as a white glass (0.249 g, 42%) from N-{5-[(4',6'-O-benzylidene-β-D-maltosyloxy)-methyl]-2-chloro-phenyl}-acetamide using phenylacetyl chloride and a procedure similar to Example 2, mp >98° C. (decomp.); $^1$H NMR (DMSO-d$_6$) δ2.08 (s, 3H), 3.08–3.13 (m, 1H), 3.27–3.49 (m, 4H), 3.54 (dd, J=5.3, 9.2 Hz, 1H), 3.56–3.63 (m, 2H), 3.66 (dd, J=4.4, 9.4 Hz, 1H), 3.71 (s, 2H), 4.06 (dd, J=4.4, 9.4 Hz, 1H), 4.12 (dd, J=5.7, 12.3 Hz, 1H), 4.32 (d, J=7.7 Hz, 1H), 4.37 (d, J=11.0 Hz, 1H), 4.58 (ABq, J=12.5 Hz, Δδ=0.16, 2H), 5.02 (d, J=3.7 Hz, 1H), 5.32 (d, J=5.3 Hz, 1H), 5.35 (d, J=5.3 Hz, 1H), 5.55 (s, 1H), 5.57 (d, J=2.9 Hz, 1H), 5.83 (6.2 Hz, 1H), 7.18–7.31 (m, 6H), 7.34–7.36 (m, 3H), 7.41–7.46 (m, 3H), 7.65 (s, 1H), 9.53 (s, 1H); IR (KBr) 3390, 2910, 2880, 1740, 1670, 1590, 1535, 1460, 1420, 1375, 1310, 1250, 1140, 1070, and 1025 cm$^{-1}$; mass spectrum [(+) FAB], m/z 730/732 (M+H)$^+$, 752/754 (M+Na)$^+$; 768/770 (M+K)$^+$; Anal. Calcd. for C$_{36}$H$_{40}$ClNO$_{13}$·2.0 H$_2$O: C, 56.43; H, 5.79; N, 1.83, Found: C, 56.62; H, 5.35; N, 1.79.

EXAMPLE 47

(R)-N-[2-Chloro-5-[[[2,3-di-O-acetyl-4-O-[2,3-di-O-acetyl-4,6-O-(phenylmethylene)-α-D-glucopyranosyl]-6-O-(phenylacetyl)-β-D-glucopyranosyl]-oxy]methyl]phenyl]acetamide The title compound was prepared as a white foam (0.125 g, 73%) from (R)-N-[-2-chloro-5-[[[6-O-(phenylacetyl)-4-O-[4,6-O-(phenylmethylene)-α-D-glucopyranosyl]-β-D-glucopyranosyl]oxy]methyl]phenyl]acetamide using a procedure similar to Example 25, mp >98° C. (decomp.); $^1$H NMR (DMSO-d$_6$) δ1.93 (s, 3H), 1.94 (s, 3H), 1.97 (s, 3H), 1.99 (s, 3H), 2.08 (s, 3H), 3.69–3.78 (m, 4H), 3.86–3.94 (m, 2H), 4.01 (ddd, J=2.6, 4.4, 9.7 Hz, 1H), 4.10 (d, J=5.3 Hz, 1H), 4.20 (dd, J=5.1, 12.3 Hz, 1H), 4.44–4.50 (m, 2H), 4.63–4.70 (m, 2H), 4.83 (d, J=8.1 Hz, 1H), 4.88 (dd, J=4.2, 10.3 Hz, 1H), 5.21–5.27 (m, 2H), 5.30 (t, J=9.2 Hz, 1H), 5.61 (s, 1H), 7.05 (dd, J=1.8, 8.1 Hz, 1H), 7.19–7.30 (m, 5H), 7.35 (s, 5H), 7.45 (d, J=8.3 Hz, 1H), 7.62 (s, 1H), 9.51 (s, 1H); IR (KBr) 3400, 3030, 2940, 2840, 1755, 1690, 1600, 1530, 1445, 1420, 1375, 1240, 1140, 1060, and 1030 cm$^{-1}$; mass spectrum [(+) FAB], m/z 898/900 (M+H)$^+$, 920/922 (M+Na)$^+$; Anal. Calcd. for $C_{44}H_{48}ClNO_{17}$. 1.75 H$_2$O: C, 56.84; H, 5.58; N, 1.51, Found: C, 56.44; H, 5.11; N, 1.59.

EXAMPLE 48

N-{5-[(4',6'-O-Benzylidene-6-O-phenyl-ethyl-carboxyl-β-D-maltosyl)-oxy-methyl]-2-chloro-phenyl}-acetamide The title compound was prepared as a white solid (0.352 g, 63%) from N-{5-[(4',6'-O-benzylidene-β-D-maltosyloxy)-methyl]-2-chloro-phenyl}-acetamide using hydrocinnamoyl chloride and a procedure similar to Example 2, mp 192–193; $^1$H NMR (DMSO-d$_6$) δ2.06 (s, 3H), 2.66 (t, J=7.7 Hz, 2H), 2.84 (t, J=7.7 Hz, 2H), 3.08–3.16 (m, 1H), 3.33–3.49 (m, 4H), 3.53–3.59 (m, 2H), 3.61–3.72 (m, 2H), 4.05–4.12 (m, 2H), 4.32–4.37 (m, 2H), 4.62 (ABq, J=12.3 Hz, Δδ=0.16, 2H), 5.09 (d, J=4.0 Hz, 1H), 5.35 (d, J=5.1 Hz, 1H), 5.33 (d, J=5.3 Hz, 1H), 5.54–5.58 (m, 1H), 5.56 (s, 1H), 5.82 (d, J=6.2 Hz, 1H), 7.12–7.18 (m, 1H), 7.18–7.26 (m, 5H), 7.34–7.40 (m, 3H), 7.42–7.46 (m, 3H), 7.65 (s, 1H), 9.51 (s, 1H); IR (KBr) 3560, 3390, 3260, 3080, 2900, 2880, 1745, 1660, 1590, 1540, 1450, 1425, 1370, 1320, 1280, 1200, 1180, 1140, 1070, 1050, 1025, 970, 755, and 695 cm$^{-1}$; mass spectrum [(+) FAB], m/z 744 (M+H)$^+$, 766 (M+Na)$^+$; Anal. Calcd. for $C_{37}H_{42}ClNO_{13}$: C, 59.72; H, 5.69; N, 1.88, Found: C, 59.75; H, 5.75; N, 2.03.

EXAMPLE 49

N-{5-[(4',6'-O-Benzylidene-6-O-phenyl-propyl-carboxyl-β-D-maltosyl)-oxy-methyl]-2-chloro-phenyl}-acetamide The title compound was prepared as a white solid (0.210 g, 68%) from N-{5-[(4',6'-O-benzylidene-β-D-maltosyloxy)-methyl]-2-chloro-phenyl}-acetamide using 4-phenylbutyryl chloride (prepared from 4-phenylbutyric acid and oxalyl chloride) and a procedure similar to Example 2, mp 184–185° C.; $^1$H NMR (MSO-d$_6$) δ1.77–1.86 (m, 2H), 2.07 (s, 3H1), 2.34 (t, J=7.2 Hz, 2H), 2.58 (t, J=7.5 Hz, 2H), 3.08–3.16 (m, 1H), 3.29–3.51 (m, 4H), 3.53–3.73 (m, 4H), 4.07–4.14 (m, 2H), 4.33–4.38 (m, 2H), 4.62 (ABq, J=12.3 Hz, Δδ=0.16, 2H), 5.09 (d, J=4.0 Hz, 1H), 5.28–5.37 (bs, 2H), 5.56 (s, 2H), 5.82 (d, J=5.3 Hz, 1H), 7.13–7.19 (m, 4H), 7.21–7.27 (m, 2H), 7.33–7.37 (m, 3H), 7.40–7.46 (m, 3H), 7.63 (s, 1H), 9.51 (s, 1H); IR (KBr) 3560, 3390, 3260, 3080, 2930, 2900, 2880, 1745, 1665, 1590, 1540, 1450, 1420, 1370, 1320, 1275, 1175, 1140, 1070, 1050, 1025, and 690 cm$^{-1}$; mass spectrum [(+) FAB], m/z 780/782 (M+Na)$^+$; Anal. Calcd. for $C_{38}H_{44}ClNO_{13}$: C, 60.20; H, 5.85; N, 1.85, Found: C, 60.13; H, 5.73; N, 1.99.

EXAMPLE 50

Diphenyl-acetic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester The title compound was prepared as a white foam (0.510 g, 77%) from N-{5-[(4',6'-O-benzylidene-β-D-maltosyloxy)-methyl]-2-chloro-phenyl}-acetamide using diphenylacetyl chloride and a procedure similar to Example 2, mp >106° C. (decomp.); $^1$H NMR (DMSO-d$_6$) δ2.08 (s, 3H), 3.03–3.09 (m, 1H), 3.26–3.38 (m, 3H), 3.41–3.47 (m, 1H), 3.51–3.62 (m, 3H), 3.66–3.73 (m, 1H), 4.02–4.07 (m, 1H), 4.15 (q, J=6.2 Hz, 1H), 4.27 (d, J=7.7 Hz, 1H), 4.46 (ABq, J=12.5 Hz, Δδ=0.15, 2H), 4.50 (d, J=10.8 Hz, 1H), 4.90 (d, J=4.0 Hz, 1H), 5.27 (s, 1H), 5.3 (d, J=5.3 Hz, 1H), 5.35 (d, J=5.3 Hz, 1H), 5.54–5.56 (m, 2H), 5.81 (d, J=6.4 Hz, 1H), 7.14 (dd, J=1.8, 8.3 Hz, 1H), 7.19–7.25 (m, 2H), 7.25–7.34 (m, 8H), 7.34–7.38 (m, 3H), 7.40–7.45 (m, 3H), 7.61 (s, 1H), 9.52 (s, 1H); IR (KBr) 3400, 3050, 2900, 2860, 1730, 1680, 1600, 1530, 1500, 1450, 1420, 1375, 1310, 1275, 1240, 1150, 1070, 1025, 750, and 690 cm$^{-1}$; mass spectrum [(+) FAB], m/z 806/808 (M+H)$^+$, 828/830 (M+Na)$^+$, 844/846 (M+K)$^+$; Anal. Calcd. for $C_{42}H_{44}ClNO_{13}$·1.0 H$_2$O: C, 61.20; H, 5.63; N, 1.70, Found: C, 61.17; H, 5.48; N, 1.59.

EXAMPLE 51

Diphenyl-acetic acid 4,5-diacetoxy-6-(3-acetylamino-4-chloro-benzyloxy)-3-(7,8-diacetoxy-2-phenyl-hexahydro-pyrano[3,2-d][1,3]dioxin-6-yloxy)-tetrahydro-pyran-2-ylmethyl ester The title compound was prepared as a white foam (0.289 g, 76%) from diphenyl-acetic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester using a procedure similar to Example 25, mp >99° C. (decomp.); $^1$H NMR (DMSO-d$_6$) δ1.92 (s, 3H), 1.94 (s, 3H), 1.96 (s, 3H), 1.99 (s, 3H), 2.08 (s, 3H), 3.66 (t, J=9.9 Hz, 1H), 3.72–3.78 (m, 1H), 3.78 (t, J=9.0 Hz, 1H), 3.87 (t, J=9.7 Hz, 1H), 3.98–4.05 (m, 2H), 4.18–4.24 (m, 1H), 4.44 (ABq, J=12.7 Hz, Δδ=0.16, 2H), 4.61–4.67 (m, 2H), 4.80 (d, J=7.9 Hz, 1H), 4.88 (dd, J=4.2, 10.3 Hz, 1H), 5.16 (d, J=4.0 Hz, 1H), 5.22 (t, J=9.9 Hz, 1H), 5.29 (t, J=9.2 Hz, 1H), 5.31 (s, 1H), 5.60 (s, 1H), 6.99 (dd, J=1.5, 8.1 Hz, 1H), 7.20–7.25 (m, 2H), 7.27–7.35 (m, 8H), 7.35 (s, 5H), 7.43 (d, J=8.1 Hz, 1H), 7.59 (s, 1H), 9.51 (s, 1H); IR (KBr) 3410, 3070, 3025, 2930, 2860, 1755, 1690, 1600, 1525, 1450, 1410, 1375, 1240, 1140, 1055, and 1030 cm$^{-1}$; mass spectrum [(+) FAB], m/z 974 (M+H)$^+$, 996 (M+Na)$^+$; Anal. Calcd. for $C_{50}H_{52}ClNO_{17}$·1.25 H$_2$O: C, 60.24; H, 5.51; N, 1.40, Found: C, 59.97; H, 5.10; N, 1.37.

EXAMPLE 52

(3,4-Dimethoxy-phenyl)-acetic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester The title compound was prepared as a white foam (0.316 g, 49%) from N-{5-[(4',6'-O-benzylidene-β-D-maltosyloxy)-methyl]-2-chloro-phenyl}-acetamide using 3,4-dimethoxyphenylacetyl chloride and a procedure similar to Example 2, mp >116° C. (decomp.); $^1$H NMR (DMSO-d$_6$) δ2.07 (s, 3H), 3.07–3.14 (m, 1H), 3.28–3.50 (m, 6H), 3.52–3.65 (m, 4H), 3.67 (s, 3H), 3.68 (s, 3H), 4.07 (dd, J=4.4, 9.7 Hz, 1H), 4.11 (dd, J=5.5, 12.3 Hz, 1H), 4.31–4.38 (m, 2H), 4.58 (ABq, J=12.3 Hz, Δδ=0.16, 2H), 4.99 (d, J=3.7 Hz, 1H), 5.34 (dd, J=5.3, 9.2 Hz, 2H), 5.55 (s, 1H), 5.57 (d, J=2.9 Hz, 1H), 5.82 (d, J=6.2 Hz, 1H), 6.76 (dd, J=2.0, 8.3 Hz, 1H), 6.82 (d, J=8.3 Hz, 1H), 6.85 (d, J=2.0 Hz, 1H), 7.18 (dd, J=2.0, 8.3 Hz, 1H), 7.34–7.37 (m, 3H), 7.41–7.46 (m, 3H), 7.64 (s, 1H), 9.53 (s, 1H); IR (KBr) 3410, 2920, 1735, 1675, 1600, 1520, 1450, 1420, 1375, 1265, 1230, 1140, 1070, and 1025 cm$^{-1}$; mass spectrum [(+) FAB], m/z 790/792 (M+H)$^+$; Anal. Calcd. for $C_{38}H_{44}ClNO_{15}.0.5\ H_2O$: C, 57.11; H, 5.68; N, 1.75, Found: C, 56.95; H, 5.55; N, 1.71.

EXAMPLE 53

(3,4-Dimethoxy-phenyl)-acetic acid 4,5-diacetoxy-6-(3-acetylamino-4-chloro-benzyloxy)-3-(7,8-diacetoxy-2-phenyl-hexahydro-pyrano[3,2-d][1,3]dioxin-6-yloxy)-tetrahydro-pyran-2-ylmethyl ester The title compound was prepared as a white foam (0.105 g, 89%) from (3,4-dimethoxy-phenyl)-acetic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester using a procedure similar to Example 25, mp >98° C. (decomp.); $^1$H NMR (DMSO-d$_6$) δ1.92 (s, 3H), 1.94 (s, 3H), 1.97 (s, 3H), 1.99 (s, 3H), 2.07 (s, 3H), 3.62–3.77 (m, 4H), 3.66 (s, 3H), 3.67 (s, 3H), 3.89 (t, J=9.2 Hz, 2H), 3.99–4.03 (m, 1H), 4.10 (dd, J=10.5, 16.0 Hz, 1H), 4.19 (dd, J=4.4, 11.9 Hz, 1H), 4.44–4.50 (m, 2H), 4.64–4.70 (m, 2H), 4.84 (d, J=8.1 Hz, 1H), 4.87 (dd, J=4.0, 10.1 Hz, 1H), 5.21 (d, J=3.7 Hz, 1H), 5.25 (d, J=9.9 Hz, 1H), 5.30 (t, J=9.2 Hz, 1H), 5.62 (s, 1H), 6.77 (dd, J=1.8, 8.1 Hz, 1H), 6.81 (d, J=8.3 Hz, 1H), 6.86 (d, J=1.8 Hz, 1H), 7.04 (dd, J=1.8, 8.3 Hz, 1H), 7.35 (s, 5H), 7.44 (d, J=8.1 Hz, 1H), 7.61 (s, 1H), 9.51 (s, 1H); IR (KBr) 3370, 2930, 2860, 1755, 1690, 1600, 1520, 1450, 1420, 1370, 1240, 1140, 1055, and 1030 cm$^{-1}$; mass spectrum [(+) FAB], m/z 958/960 (M+H)$^+$, 980/982 (M+Na)$^+$; Anal. Calcd. for $C_{46}H_{52}ClNO_{19}.1.75\ H_2O$: C, 55.81; H, 5.65; N, 1.41, Found: C, 55.60; H, 5.14; N, 1.38.

EXAMPLE 54

Nicotinic acid 6-(3-acetylamino-4-chloro-benzyloxy)-3-(7,8-dihydroxy-2-phenyl-hexahydro-pyrano[32-d][1,3]dioxin-6-yloxy)-4,5-dihydroxy-tetrahydro-pyran-2-ylmethyl ester The title compound was prepared as a white solid (0.278 g, 47%) from N-{5-[(4',6'-O-benzylidene-β-D-maltosyloxy)-methyl]-2-chloro-phenyl}-acetamide using nicotinoyl chloride hydrochloride and a procedure similar to Example 2, mp >133° C. (decomp.); $^1$H NMR (DMSO-d$_6$) δ2.04 (s, 3H), 3.16–3.23 (m, 1H), 3.36 (d, J=9.4 Hz, 1H), 3.36–3.42 (m, 1H), 3.48–3.61 (m, 3H), 3.63 (t, J=9.4 Hz, 1H), 3.68–3.75 (m, 1H), 3.76–3.80 (m, 1H), 4.04 (dd, J=4.6, 9.9 Hz, 1H), 4.36–4.41 (m, 2H), 4.64 (d, J=10.5 Hz, 1H), 4.65 (ABq, J=12.5 Hz, Δδ=0.14, 2H), 5.16 (d, J=4.0 Hz, 1H), 5.35 (dd, J=4.0, 5.1 Hz, 2H), 5.52 (s, 1H), 5.58 (d, J=2.9 Hz, 1H), 5.8 (d, J=6.2 Hz, 1H), 7.19 (dd, J=1.8, 8.3 Hz, 1H), 7.34–7.38 (m, 3H), 7.39–7.43 (m, 3H), 7.57 (ddd, J=0.7, 4.8, 7.9 Hz, 1H), 7.64 (s, 1H), 8.33 (dt, J=2.0, 7.9 Hz, 1H), 8.82 (dd, J=1.8, 4.8 Hz, 1H), 9.12 (d, J=2.2 Hz, 1H), 9.49 (s, 1H); IR (KBr) 3410, 2910, 2870, 1730, 1625, 1600, 1530, 1455, 1425, 1380, 1290, 1130, 1110, 1070, 1025, 740, and 690 cm$^{-1}$; mass spectrum [(+) FAB], m/z 717/719 (M+H)$^+$; Anal. Calcd. for $C_{34}H_{37}ClN_2O_{13}.1.0\ H_2O$: C, 55.55; H, 5.35; N, 3.81, Found: C, 55.55; H, 5.30; N, 3.78.

EXAMPLE 55

Nicotinic acid 4,5-diacetoxy-6-(3-acetylamino-4-chloro-benzyloxy)-3-(7,8-diacetoxy-2-phenyl-hexahydro-pyrano[3,2-d][1,3]dioxin-6-yloxy)-tetrahydro-pyran-2-ylmethyl ester The title compound was prepared as a white foam (0.157 g, 73%) from nicotinic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester using a procedure similar to Example 25, mp >112° C. (decomp.); $^1$H NMR (DMSO-d$_6$) δ1.94 (s, 3H), 1.95 (s, 3H), 1.98 (s, 3H), 1.99 (s, 3H), 2.05 (s, 3H), 3.64 (t, J=9.4 Hz, 1H), 3.69–3.76 (m, 1H), 3.79 (dd, J=4.2, 9.2 Hz, 1H), 3.87 (t, J=9.4 Hz, 1H), 4.13–4.19 (m, 1H), 4.26 (t, J=9.4 Hz, 1H), 4.48 (dd, J=4.0, 12.3 Hz, 1H), 4.64 (ABq, J=12.7 Hz, Δδ=0.14, 2H), 4.71–4.76 (m, 1H), 4.82 (dd, J=8.1, 9.2 Hz, 1H), 4.87–4.92 (m, 2H), 5.26 (t, J=10.1 Hz, 1H), 5.32–5.38 (m, 2H), 5.5 (s, 1H), 7.04 (dd, J=1.8, 8.1 Hz, 1H), 7.29–7.36 (m, 5H), 7.42 (d, J=8.1 Hz, 1H), 7.58 (dd, J=4.8, 8.1 Hz, 1H), 7.61 (s, 1H), 8.39 (dt, J=2.0, 7.9 Hz, 1H), 8.84 (dd, J=1.5, 4.6 Hz, 1H), 9.17–9.19 (m, 1H), 9.49 (s, 1H); IR (KBr) 3410, 2940, 2860, 1755, 1690, 1600, 1530, 1450, 1420, 1380, 1290, 1240, 1140, 1055, 1030, and 995 cm$^{-1}$; mass spectrum [(+) FAB], m/z 885 (M+H)$^+$, 907 (M+Na)$^+$; Anal. Calcd. for $C_{42}H_{45}ClN_2O_{17}.1.0\ H_2O$: C, 55.85; H, 5.24; N, 3.10, Found: C, 55.61; H, 4.89; N, 2.99.

EXAMPLE 56

(R)-N-[5-[[[6-O-(4-Benzoylbenzoyl)-4-O-[4,6-O-(phenylmethylene)-α-D-glucopyranosyl]-β-D-glucopyranosyl]oxy]methyl]-2-chlorophenyl]acetamide The title compound was prepared as a white powder (0.347 g, 52%) from N-{5-[(4',6'-O-benzylidene-β-D-maltosyloxy)-methyl]-2-chloro-phenyl}-acetamide using p-benzoylbenzoyl chloride (prepared from p-benzoylbenzoic acid and oxalyl chloride) and a procedure similar to Example 2, mp >117° C. (decomp.); $^1$H NMR (DMSO-d$_6$) δ2.03 (s, 3H), 3.17–3.23 (m, 1H), 3.27–3.43 (m, 2H), 3.49–3.66 (m, 4H), 3.70–3.82 (m, 2H), 4.08 (4.8, 10.1 Hz, 1H), 4.39–4.44 (m, 2H), 4.64 (d, J=10.5 Hz, 1H), 4.66 (ABq, J=12.3 Hz, Δδ=0.14, 2H), 5.16 (d, J=4.0 Hz, 1H), 5.36 (t, J=5.3 Hz, 2H), 5.53 (s, 1H), 5.60 (d, J=2.9 Hz, 1H), 5.83 (d, J=6.2 Hz, 1H), 7.20 (dd, J=1.8, 8.1 Hz, 1H), 7.33–7.37 (m, 3H), 7.39–7.43 (m, 3H), 7.54–7.59 (m, 2H), 7.65 (s, 1H), 7.67–7.73 (m, 1H), 7.73–7.77 (m, 2H), 7.82–7.86 (m, 2H), 8.13–8.17 (m, 2H), 9.49 (s, 1H); IR (KBr) 3410, 3080, 2910, 2850, 1725, 1660, 1600, 1530, 1450, 1420, 1400, 1365, 1270, 1140, 1070, and 1025 cm$^{-1}$; mass spectrum [(−) ESI], m/z 818.1 (M−H)$^-$; Anal. Calcd. for $C_{42}H_{42}ClNO_{14}.0.5\ H_2O$: C, 60.83; H, 5.23; N, 1.69, Found: C, 60.71; H, 5.28; N, 1.61.

EXAMPLE 57

N-{5-[(4',6'-O-Benzylidene-β-D-maltosyl)-oxy-methyl]-2-methyl-phenyl}-acetamide

Step 1

5-[(Hepta-O-acetyl-β-D-maltosyl)-oxy-methyl]-2-methyl-1-nitrobenzene

The title compound was prepared as a colorless solid (8.02 g, 53%) from 4-methyl-3-nitrobenzyl alcohol and acetobromomaltose using a procedure similar to step 1 of Example 1, mp 68–74° C.; $^1$H NMR (DMSO-d$_6$) δ1.93 (s, 3 H), 1.94 (s, 3 H), 1.95 (s, 3 H), 1.96 (s, 3 H), 1.97 (s, 3 H), 2.012 (s, 3 H), 2.07 (s, 3 H), 3.93–4.01 (m, 4 H), 4.13–4.21 (m, 2 H), 4.37 (d, 2 H), 4.64–4.90 (m, 5 H), 4.97 (t, 1 H), 5.20 (dd, 1 H), 5.27–5.33 (m, 2 H), 7.48 (d, 1 H), 7.52 (d, 1H), 7.88 (s, 1 H). IR (KBr) 2950, 1750, 1230 and 1050 cm$^{-1}$, mass spectrum [(+FAB)], m/z 808 (M+H)$^+$. Anal. Calcd. for $C_{34}H_{43}NO_2$: C, 51.98; H,5.52; N, 1.78. Found: C, 51.59; H, 5.45; N, 1.86.

Step 2

5-(Hepta-O-acetyl-β-D-maltosyloxymethyl)-2-methylphenylamine

The title compound was prepared as a white foam (5.39 g, 79%) from 5-(hepta-O-acetyl-β-D-maltosyloxymethyl)-2-methyl-1-nitrobenzene using a procedure similar to step 2 of Example 1; $^1$H NMR (DMSO-d$_6$) δ1.93 (s, 3 H), 1.94 (s, 3 H), 1.95 (s, 3 H), 1.97 (s, 3 H), 1.98 (s, 3 H), 2.03 (s. 6 H), 2.10 (s, 3 H), 3.93–4.03 (m, 4 H), 4.14–4.23 (m, 2 H), 4.32–4.41 (m, 2 H), 4.58 (d, 1 H), 4.68 (t, 1 H), 4.76–4.88 (m, 4 H), 4.98 (t, 1 H), 5.22 (t, 1 H), 5.28–5.31 (m, 2 H), 6.37 (d, 2 H), 6.49 (s, 1 H), 6.87 (d, 1 H).

Step 3

N-[5-(Hepta-O-acetyl-β-D-maltosyloxymethyl)-2-methylphenyl]acetamide

The title compound was prepared as a white foam (6.60 g, 91%) from 5-(hepta-O-acetyl-β-D-maltosyloxymethyl)-2-methylphenylamine using a procedure similar to step 3 of Example 1; $^1$H NMR (DMSO-d$_6$) δ1.93 (s, 3 H), 1.94 (s, 3 H), 1.95 (s, 3 H), 1.979 (s, 3 H), 1.984 (s, 3 H), 2.03 (s, 3 H), 2.10 (s, 3 H), 2.18 (s, 3 H), 3.94–4.02 (m, 4 H), 4.14–4.24 (m, 2 H), 4.40 (d, 1 H), 4.48 (d, 1 H), 4.67–4.74 (m 2 H), 4.81–4.89 (m 2 H), 4.98 (t, 1 H), 5.19–5.32 (m, 3 H), 6.98 (d, 1 H), 7.17 (d, 1 H),7.33 (s, 1 H), 9.27 (s, 1 H).

Step 4

N-[5-(β-D-Maltosyloxy-methyl)-2-methyl-phenyl]-acetamide

A solution containing N-[5-(hepta-O-acetyl-β-D-maltosyloxymethyl)-2-methylphenyl]acetamide (6.60 g, 8.27 mnmol) and 25 weight % NaOMe in MeOH (0.893 g, 4.14 mmol) in MeOH (198 mL) was refluxed for 2.5 h. The reaction was cooled to room temperature and concentrated to give 4.09 g (98%) of the product as a white foam. This material was used without any additional purification.

An analytical sample was obtained by reverse phase HPLC (C18, 15% CH$_3$CN/H$_2$O) to give a white solid, mp 115° C.; $^1$H NMR (DMSO-d$_6$) δ2.03 (s, 3 H), 2.16 (s, 3 H), 3.04–3.09 (m, 2 H), 3.21–3.56 (m, 7 H), 3.57–3.62 (m, 2 H), 3.70–3.73 (m, 1 H), 4.26 (d, 1 H), 4.48–4.54 (m, 3 H), 4.76 (d, 1 H), 4.86–4.89 (m, 2 H), 5.01 (d, 1 H), 5.17 (d, 1 H), 5.42 (d, 1 H), 5.49 (d, 1 H), 7.10 (d, 1 H), 7.15 (d, 1 H), 7.35 (s, 1 H), 9.28 (s, 1 H). IR (KBr) 3375, 2900, 1670 and 1025 cm$^{-1}$, mass spectrum [(+) FAB], m/z 504 (M+H)$^+$, 526 (M+Na)$^+$. Anal. Calcd. for C$_{22}$H$_{33}$NO$_{12}$.0.5 H$_2$O: C, 51.56; H, 6.67; N, 2.73. Found: C, 51.78; H, 6.81; N, 2.75.

Step 5

N-{5-[(4',6'-O-Benzylidene-β-D-maltosyl)-oxy-methyl]-2-methyl-phenyl}-acetamide A solution containing N-{5-[(β-D-maltosyl)-oxy-methyl]-2-methyl-phenyl}-acetamide (1.88 g, 3.83 mmol), benzaldehyde dimethyl acetal (0.807 mL, 5.36 mmol) and p-toluenesulfonic acid monohydrate (72.7 mg, 0.383 mmol) was heated at 60° C. After 4 h, additional benzaldehyde dimethyl acetal (0.403 mL, 2.68 mmol) and p-toluenesulfonic acid monohydrate (36.4 mg, 0.192 mmol) was added and the reaction was heated at 60° C. for 16 h. To the reaction was added K$_2$CO$_3$ and heating was continued for 0.5 h. The hot solution was filtered and the filtrate concentrated. Purification by reverse phase HPLC (C18, 15% CH$_3$CN:H$_2$O) gave 1.26 g (56%) of the title compound as a white solid, mp 190–197° C.; $^1$H NMR (DMSO-d$_6$) δ2.04 (s, 3H), 2.16 (s, 3H), 3.08 (t, 1H), 3.35–3.40 (m, 3H), 3.45 (t, 1H), 3.53–3.59 (m 2H), 3.64–3.75 (m, 3H), 4.11 (dd, J=5.1, 2.4 Hz, 1H), 4.28 (d, 1H), 4.50 (d,1H), 4.67 (t, 1H), 4.77 (d, 1H), 5.13 (d, 1H), 5.21 (br. s, 1H), 5.29 (br. s, 1H), 5.49 (br. s, 1H), 5.57 (s, 1H), 5.61 (br. s, 1H), 7.10 (d, 1H), 7.16 (d, 1H), 7.34–7.38 (m, 4H), 7.42–7.45 (s, 2H), 9.28 (s, 1H); IR (KBr) 3400, 2900, 1650 and1075 cm$^{-1}$; mass spectrum [(+) ESI], m/z 609 (M+NH$_4$)$^+$, 614 (M+Na)$^+$; Anal. Calcd. for C$_{29}$H$_{37}$NO$_{12}$.0.5 H$_2$O: C, 57.99; H, 6.30; N, 2.37, Found: C, 57.80; H, 6.39; N, 2.50. Found: C, 57.85; H, 6.33; N, 2.27.

EXAMPLE 58

N-Acetyl-{5-[(2,2',3,3',6-penta-O-acetyl-4',6'-O-benzylidene-β-D-maltosyl)-oxy-methyl]-2-methyl-phenyl}acetamide At 0° C., to a stirred solution containing N-{5-[(4',6'-O-benzylidene-β-D-maltosyl)-oxy-methyl]-2-methyl-phenyl}-acetamide (0.406 g, 0.686 mmol), pyridine (1.66 nL, 20.6 mmol) and 4-dimethylaminopyridine (0.768 g, 6.86 mmol) was added dropwise acetic anhydride (1.28 mL, 13.7 mmol). After 6 h, with reaction eventually warmed to room temperature, the solution was diluted with diethyl ether (100 mL), washed successively with H$_2$O (2×), sat. aq. NaHCO$_3$ (2×), sat. aq. CuSO$_4$ (2×), brine (2×), dried (Na$_2$SO4) and concentrated. Purification by flash chromatography (3, 4 and 5% MeOH:CHCl$_3$ gradient) gave 0.194 g, (34%), of a white solid after cryatallization from CH$_2$Cl$_2$:petroleum ether, mp 97° C.; $^1$H NMR (DMSO-d$_6$) δ1.90 (s, 3H), 1.92 (s, 3H), 1.98 (s, 3H), 1.99 (s, 3H), 2.06 (s, 3H), 2.08 (s, 3H), 2.13 (s, 3H), 2.17 (s, 3H), 3.71–3.80 (m, 2H), 3.95–4.02 (m, 2H), 4.12–4.18 (m, 2H), 4.39 (dd, J=9.9, 2.2 Hz, 1H), 4.56 (d, 1H), 4.67–4.75 (m, 2H), 4.86–4.90 (m, 2H), 5.22–5,33 (m, 3H), 5.61 (s, 1H), 7.11 (s, 1H), 7.24 (d, 1H), 7.34 (d, 1H), 7.36 (s, 5H); IR (KBr) 3450, 2900, 1750 and 1240 cm$^{-1}$; mass spectrum [(+) FAB], m/z 844 (M+H)$^+$, 866 (M+Na)$^+$; Anal. Calcd. for C$_{41}$H$_{49}$NO$_{18}$: C, 58.36; H, 5.85; N, 1.66, Found: C, 57.99; H, 5.76; N, 1.67.

EXAMPLE 59

N-(5-{[4',6'-O-Benzylidene-6-O-(4-toluenesulfonyl)-β-D-maltosyl]-oxy-methyl}-2-methyl-phenyl)-acetamide At 0° C., to a stirred solution of N-{5-[(4',6'-O-benzylidene-β-D-maltosyl)-oxy-methyl]-2-methyl-phenyl}-acetamide (0.711 g, 1.20 mmol) in pyridine (2.4 mL) was added a solution of p-toluenesulfonyl chloride (0.275 g, 1.44 mmol) in CH$_2$Cl$_2$ (1.5 mL). After 2 h, additional p-toluenesulfonyl chloride (0.275 g, 1.44 mmol) in CH$_2$Cl$_2$ (1.5 mL) was added and the solution was stirred at 0° C. for 2 h. The reaction was quenched with ice cold H$_2$O (50 nmL) and extracted with EtOAc. The combined organic extracts were washed successively with sat. aq. NaHCO$_3$ (2×), sat. aq. CuSO$_4$ (2×), brine (2×), dried (Na$_2$SO$_4$) and concentrated. Purification by reverse phase HPLC (C18, 50% CH$_3$CN:H$_2$O) gave 0.421 g, (47%) of a colorless solid, mp 115–121° C.; $^1$H NMR (DMSO-d$_6$) δ2.05 (s, 3H), 2.17 (s, 3H), 2.33 (s, 3H), 3.05 (t, 1H), 3.24–3.44 (m, 4H), 3.52 (t, 1H), 3.58–3.62 (m, 3H), 3.95 (d, 1H), 4.13 (dd, 1H), 4.28 (d, 1H), 4.33 (d, 1H), 4.41 (d, 1H), 4.59 (d, 1H), 5.05 (d, 1H), 5.57 (s, 1H), 7.06 (d, 1H), 7.16 (d, 1H), 7.33–7.47 (m, 8H), 7.78 (d, 2H), 9.29 (s, 1H); IR (KBr) 3375, 2900, 1650, 1350, 1175 and 1075 cm$^{-1}$; mass spectrum [(+) FAB], m/z 746 (M+H)$^+$, 768 (M+Na)$^+$; Anal. Calcd. for C$_{36}$H$_{43}$NO$_{14}$S.H$_2$O: C, 56.61; H, 5.94; N, 1.83, Found: C, 56.61; H, 5.77; N, 1.80.

EXAMPLE 60

N-{5-[(4',6'-O-Benzylidene-6-O-phenyl-β-D-maltosyl)-oxy-methyl]-2-chloro-phenyl}-acetamide At ambient temperature, to a stirred solution of phenol (0.0784 g, 0.833 mmol) in DMF (10 mL) was added potassium-t-butoxide (0.0982 g, 0.833 mmol). After 0.5 h, to the reaction was added a solution of N-(5-{[2,3,2',3'-tetra-O-acetyl-4',6'-O-benzylidene-6-O-(4-toluenesulfonyl)-β-D-maltosyl]-oxy-methyl}-2-chloro-phenyl)-acetamide (0.389 g, 0.417 mmol) in DMF (4 mL) and the reaction was heated at 65° C. for 3 h. The reaction was cooled to ambient temperature, quenched with $H_2O$ (40 mL), extracted with EtOAc, dried ($Na_2SO_4$) and concentrated. The crude product was dissolved in MeOH (10 mL) and treated with 25 weight % NaOMe in MeOH (45 mg) at 65° C. for 3 h. The reaction was cooled to ambient temperature and concentrated. Purification by flash chromatography (5 and 10% MeOH:$CHCl_3$ gradient) gave 0.149 g (39%) of title compound as a solid; $^1H$ NMR (DMSO-$d_6$) δ2.05 (s, 3H), 3.13–3.19 (m, 1H), 3.27–3.40 (m, 2H), 3.44–3.66 (m, 5H), 3.70–3.73 (m, 2H), 4.14 (dd, J=10.8, 4.4 Hz, 1H), 4.23 (d, J=10.9 Hz, 1H), 4.39 (d, J=7.7 Hz, 1H), 4.64 (ABq, J=12.3 Hz, Δδ=0.08, 2H), 5.16 (d, J=3.7 Hz, 1H), 5.28 (d, J=5.1 Hz, 1H), 5.33 (d, J=5.3 Hz, 1H), 5.47 (s, 1H), 5.56 (d, J=3.3 Hz, 1H), 5.67 (d, J=6.4 Hz, 1H), 6.90–6.97 (m, 3H), 7.20 (dd, J=8.2, 1.9 Hz, 1H), 7.25–7.29 (m, 2H), 7.32–7.36 (m, 5H), 7.42 (d, J=8.3 Hz, 1H), 7.65 (s, 1H), 9.50 (s, 1H); IR (KBr) 3400, 2900, 1650 and 1070 cm$^{-1}$; mass spectrum [(+) FAB], m/z 710 (M+Na)$^+$; Anal. Calcd. for $C_{34}H_{38}NClO_{12}$: C, 59.34; H, 5.57; N, 2.03, Found: C, 58.96; H, 5.78; N, 2.16.

EXAMPLE 61

(R)-N-[2-Chloro-5-[[[4-O-[4',6'-O-(phenylmethylene)-α-D-glucopyranosyl]-β-D-glucopyranosyl]oxy]methyl]phenyl]-3-pyridinecarboxamide Step 1

N-[2-Chloro-5-[[[2,3,6-tri-O-acetyl-4-O-(2,3,4,6-tetra-O-acetyl-α-D-glucopyranoysl)-β-D-glucopyranosyl]oxy]methyl]phenyl]-3-pyridinecarboxamide To a stirred solution of 2-chloro-5-(hepta-O-acetyl-β-D-maltosyl-oxymethyl)-phenylamine (0.200 g, 0.258 mmol) and triethylamine (0.119 mL, 0.851 mmol) in THF (3 mL) at 0° C. was added nicotinoyl chloride hydrochloride (0.0551 mg, 0.310 mmol). After 0.5 h at this temperature, it was warmed to rt and stirred an additional 18 h. At this point, the solid was filtered off and washed with additional THF (10 mL). The filtrate was then concentrated and taken up in EtOAc (100 mL). This organic solution was washed with $H_2O$ (10 mL) and brine (10 mL) and then dried ($Na_2SO_4$). After concentration, the residue was purified by preparatory plate chromatography (10:90 MeOH:$CHCl_3$) to afford the product (0.183 g, 80%) as a white foam, mp 83–86° C.; $^1H$ NMR (CDCl$_3$) δ1.99 (s, 3H), 2.00 (s, 3H), 2.02 (s, 3H), 2.03 (s, 3H), 2.04 (s, 3H), 2.10 (s, 3H), 2.16 (s, 3H), 3.67–3.72 (m, 1H), 3.93–3.98 (m, 1H), 4.04 (dd, J=2.2, 11.9 Hz, 1H), 4.25 (dt, J=3.7, 12.5 Hz, 2H), 4.53 (d, J=2.9, 12.3 Hz, 1H), 4.60 (d, J=7.7 Hz, 1H), 4.64 (d, J=12.5 Hz, 1H), 4.83–4.93 (m, 3H), 5.05 (t, J=10.1 Hz, 1H), 5.23 (t, J=9.4 Hz, 1H), 5.34 (dd, J=9.7, 10.5 Hz, 1H), 5.41 (d, J=4.2 Hz, 1H), 7.07 (dd, J=2.0 Hz, 1H), 7.41 (d, J=8.1 Hz, 1H), 7.48 (ddd, J=0.9, 4.8, 7.9 Hz, 1H), 8.23 (ddd, J=1.5, 2.2, 7.9 Hz, 1H), 8.43 (s, 1H), 8.48 (d, J=2.0 Hz, 1H), 8.82 (dd, J=1.5, 4.8 Hz, 1H), 9.15 (dd, J=0.7, 2.2 Hz, 1H); IR (KBr) 3400, 2950, 1755, 1675, 1600, 1550, 1420, 1375, 1235, and 1050 cm$^{-1}$; mass spectrum [(+) FAB], m/z 881 (M+H)$^+$, 903 (M+Na)$^+$; Anal. Calcd. for $C_{39}H_{45}ClN_2O_{19}$.2.0 $H_2O$: C, 51.07; H, 5.38; N, 3.05, Found: C, 50.80; H, 4.83; N, 2.89.

Step 2

N-[2-chloro-5-[[(4-O-α-D-glucopyranosyl-β-D-glucopyranosyl)oxy]methyl]phenyl]-3-pyridinecarboxamide The title compound was prepared as a white foam (1.97 g, 57%) from N-[2-chloro-5-[[[2,3,6-tri-O-acetyl-4-O-(2,3,4,6-tetra-O-acetyl-α-D-glucopyranoysl)-β-D-glucopyranosyl]oxy]methyl]phenyl]-3-pyridinecarboxamide using a procedure similar to step 4 of Example 1, mp >106° C. (decomp.); $^1H$ NMR (DMSO-$d_6$) δ3.02–3.13 (m, 2H), 3.19–3.29 (m, 2H), 3.31–3.39 (m, 1H), 3.39–3.50 (m, 3H), 3.55–3.63 (m, 2H), 3.70–3.76 (m, 1H), 4.09 (q, J=5.3 Hz, 1H), 4.31 (d, J=7.9 Hz, 1H), 4.49–4.55 (m, 2H), 4.60 (d, J=12.5 Hz, 1H), 4.84–4.91 (m, 3H), 5.01 (d, J=3.7 Hz, 1H), 5.26 (d, J=5.1 Hz, 1H), 5.43 (d, J=6.4 Hz, 1H), 5.52 (d, J=3.1 Hz, 1H), 7.35 (dd, J=2.0, 8.3 Hz, 1H), 7.54 (d, J=8.1 Hz, 1H), 7.56–7.60 (m, 2H), 8.31 (dt, J=2.0, 7.9 Hz, 1H), 8.77 (dd, J=1.5, 4.8 Hz, 1H), 9.12–9.14 (m, 1H), 10.34 (s, 1H); IR (KBr) 3390, 2910, 2320, 1660, 1590, 1525, 1475, 1450, 1420, 1360, 1310, 1190, 1140, 1080, and 1030 cm$^{-1}$; mass spectrum [(+) FAB], m/z 587 (M+H)$^+$, 609 (M+Na)$^+$, Anal. Calcd. for $C_{25}H_{31}ClN_2O_{12}$.1.5 $H_2O$: C, 48.90; H, 5.58; N, 4.56, Found: C, 49.18; H, 5.52; N, 4.32.

Step 3

(R)-N-[2-Chloro-5-[[[4-O-[4',6'-O-(phenylmethylene)-α-D-glucopyranosyl]-β-D-glucopyranosyl]oxy]methyl]phenyl]-3-pyridinecarboxamide The title compound was prepared as a white solid (1.25 g, 57%) from N-[2-chloro-5-[[(4-O-α-D-glucopyranosyl-β-D-glucopyranosyl)oxy]methyl]phenyl]-3-pyridinecarboxamide using a procedure similar to Example 24, mp 208–210° C.; $^1H$ NMR (DMSO-$d_6$) δ3.08–3.15 (m, 1H), 3.30–3.42 (m, 4H), 3.42–3.51 (m, 1H), 3.51–3.60 (m, 2H), 3.64–3.76 (m, 3H), 4.12 (dd, J=3.3, 8.6 Hz, 1H), 4.33 (d, J=7.7 Hz, 1H), 4.68 (t, J=5.7 Hz, 1H), 4.74 (ABq, J=12.5 Hz, Δδ=0.22, 2H), 5.14 (d, J=3.7 Hz, 1H), 5.30 (t, J=4.4 Hz, 2H), 5.52 (d, J=3.3 Hz, 1H), 5.57 (s, 1H), 5.63 (d, J=6.6 Hz, 1H), 7.34–7.38 (m, 4H), 7.42–7.46 (m, 2H), 7.54 (d, J=8.3 Hz, 1H), 7.55–7.60 (m, 2H), 8.31 (dt, J=1.8, 7.9 Hz, 1H), 8.77 (dd, J=1.8, 4.8 Hz, 1H), 9.13 (dd, J=0.7, 2.2 Hz, 1H), 10.34 (s, 1H); IR (KBr) 3530, 3400, 2920, 2830, 1680, 1590, 1540, 1460, 1420, 1380, 1320, 1275, 1150, 1120, 1070, and 1025 cm$^{-1}$; mass spectrum [(+) FAB], m/z 675/677 (M+H)$^+$, 697/699 (M+Na)$^+$; Anal. Calcd. for $C_{32}H_{35}ClN_2O_{12}$.0.5 $H_2O$: C, 56.18; H, 5.30; N, 4.09, Found: C, 56.31; H, 5.13; N, 4.19.

EXAMPLE 62

(R)-N-[5-[[[6-O-Benzoyl-4-O-[4',6'-O-(phenylmethylene)-α-D-glucopyranosyl]-β-D-glucopyranosyl]oxy]methyl]-2-chlorophenyl]-3-pyridinecarboxamide The title compound was prepared as a off-white glassy solid (0.628 g, 44%) from (R)-N-[2-chloro-5-[[[4-O-[4,6-O-(phenylmethylene)-α-D-glucopyranosyl]-β-D-glucopyranosyl]oxy]methyl]phenyl]-3-pyridinecarboxamide using a procedure similar to Example 2, mp 190–193° C.; $^1$H NMR (DMSO-d$_6$) δ3.17–3.24 (m, 1H), 3.30–3.43 (m, 2H), 3.50–3.64 (m, 4H), 3.68–3.76 (m, 1H), 3.78 (ddd, J=1.5, 5.1, 9.7 Hz, 1H), 4.50 (dd, J=4.8, 9.9 Hz, 1H), 4.36 (dd, J=5.1, 12.1 Hz, 1H), 4.43 (d, J=7.7 Hz, 1H), 4.59–4.64 (m, 1H), 4.71 (ABq, J=12.7 Hz, Δδ=0.14, 2H), 5.14 (d, J=3.7 Hz, 1H), 5.35 (d, J=5.1 Hz, 1H), 5.39 (d, J=5.3 Hz, 1H), 5.52 (s, 1H), 5.59 (d, J=3.1 Hz, 1H), 5.80 (d, J=6.4 Hz, 1H), 7.31–7.37 (m, 4H), 7.39–7.43 (m, 2H), 7.51 (dd, J=5.9, 7.9 Hz, 3H), 7.54–7.58 (m, 2H), 7.60–7.66 (m, 1H), 7.98 (dd, J=1.1, 8.1 Hz, 2H), 8.29 (dt, J=1.8, 7.9 Hz, 1H), 8.77 (dd, J=1.8, 4.8 Hz, 1H), 9.11 (d, J=2.0 Hz, 1H), 10.31 (s, 1H); IR (KBr) 3410, 3080, 2900, 2850, 1720, 1680, 1590, 1530, 1440, 1420, 1375, 1320, 1275, 1070, 1025, 755, and 710 cm$^{-1}$; mass spectrum [(+) FAB], m/z 779/781 (M+H)$^+$, 801/803 (M+Na)$^+$; Anal. Calcd. for C$_{39}$H$_{39}$ClN$_2$O$_{13}$.0.5 H$_2$O: C, 59.43; H, 5.12; N, 3.55, Found: C, 59.34; H, 4.91; N, 3.45.

EXAMPLE 63

Furan-2-carboxylic acid {5-[(4',6'-O-benzylidene-β-D-maltosyl)-oxy-methyl]-2-chloro-phenyl}-amide Step 1

Furan-2-carboxylic acid {5-[(2,2',3,3',4',6,6'-hepta-O-acetyl-β-D-maltosyl)-oxymethyl]-2-chloro-phenyl}-amide The title compound was prepared as a white foam (1.47 g, 94%) from 2-chloro-5-(hepta-O-acetyl-β-D-maltosyl-oxymethyl)-phenylamine using a procedure similar to step 3 of Example 1, mp >85° C. (decomp.); $^1$H NMR (DMSO-d$_6$) δ1.93 (s, 6H), 1.94 (s, 3H), 1.969 (s, 3H), 1.972 (s, 3H), 2.01 (s, 3H), 2.07 (s, 3H), 3.92–4.02 (m, 4H), 4.12–4.23 (m, 2H), 4.38 (dd, J=2.2, 12.1 Hz, 1H), 4.67 (ABq, J=13.0 Hz, Δδ=0.15, 2H), 4.73 (dd, J=7.9, 9.4 Hz, 1H), 4.83–4.90 (m, 2H), 4.97 (t, J=9.7 Hz, 1H), 5.21 (t, J=10.1 Hz, 1H), 5.27 (d, J=4.2 Hz, 1H), 5.31 (d, J=9.2 Hz, 1H), 6.70 (q, J=1.8 Hz, 1H), 7.18 (dd, J=2.0, 8.3 Hz, 1H), 7.32 (d, J=3.5 Hz, 1H), 7.53 (d, J=8.1 Hz, 1H), 7.57 (d, J=2.0 Hz, 1H), 7.93–7.95 (m, 1H), 9.84 (s, 1H); IR (KBr) 3390, 3130, 2950, 1755, 1690, 1590, 1530, 1445, 1420, 1375, 1320, 1230, 1140, and 1040 cm$^{-1}$; mass spectrum [(+) FAB], m/z 870 (M+H)$^+$, 892 (M+Na)$^+$, Anal. Calcd. for C$_{38}$H$_{44}$ClNO$_{20}$.1.0 H$_2$O: C, 51.39; H, 5.22; N, 1.58, Found: C, 51.00; H, 4.93; N, 1.51.

Step 2

Furan-2-carboxylic acid {2-chloro-5-[(β-D-maltosyl)-oxy-methyl]-phenyl}-amide

A solution containing furan-2-carboxylic acid {5-[(2,2',3,3',4',6,6'-hepta-O-acetyl-β-D-maltosyl)-oxymethyl]-2-chloro-phenyl}-amide (1.36 g, 1.56 mmol) and 25 weight % NaOMe in MeOH (26.8 μL, 0.468 mmol) in MeOH (41 ml) was stirred at rt for 18 h. At this point, the mixture was concentrated, and the resulting residue was triturated with Et$_2$O to afford the product (0.890 g, 99%) as a white foam, mp >127° C. (decomp.); $^1$H NMR (DMSO-d$_6$) δ3.01–3.12 (m, 2H), 3.21 (dd, J=3.7, 9.7 Hz, 1H), 3.24–3.29 (m, 1H), 3.29–3.38 (m, 2H), 3.38–3.50 (m, 3H), 3.54–3.63 (m, 2H), 3.73 (d, J=12.3 Hz, 1H), 4.30 (d, J=7.7 Hz, 1H), 4.45–4.58 (m, 2H), 4.71 (ABq, J=12.5 Hz, Δδ=0.22, 2H), 4.83–4.93 (bs, 2H), 5.01 (d, J=4.0 Hz, 1H), 5.18–5.32 (bs, 1H), 5.34–5.58 (bs, 2H), 6.69 (dd, J=1.5, 3.3 Hz, 1H), 7.26–7.33 (m, 2H), 7.50 (d, J=8.3 Hz, 1H), 7.62 (d, J=2.0 Hz, 1H), 7.92–7.94 (m, 1H), 9.82–9.94 (bs, 1H); IR (KBr) 3400, 2920, 2880, 1675, 1590, 1530, 1445, 1425, 1365, 1315, 1140, 1080, 1030, and 755 cm$^{-1}$; mass spectrum [(+) FAB], m/z 598/600 (M+Na)$^+$, Anal. Calcd. for C$_{24}$H$_{30}$ClNO$_{13}$.0.5 H$_2$O: C, 49.28; H, 5.34; N, 2.39, Found: C, 49.06; H, 5.34; N, 2.21.

Step 3

Furan-2-carboxylic acid {5-[(4',6'-O-benzylidene-β-D-maltosyl)-oxy-methyl]-2-chloro-phenyl}-amnide The title compound was prepared as a white solid (0.352 g, 63%) from furan-2-carboxylic acid {2-chloro-5-[(β-D-maltosyl)-oxy-methyl]-phenyl}-amide using a procedure similar to Example 24, mp 224–226° C.; $^1$H NMR (DMSO-d$_6$) δ3.07–3.14 (m, 1H), 3.27–3.42 (m, 4H), 3.42–3.49 (m, 1H), 3.51–3.59 (m, 2H), 3.63–3.7 (m, 3H), 4.11 (dd, J=2.4, 7.9 Hz, 1H), 4.32 (d, J=7.7 Hz, 1H), 4.67 (t, J=5.9 Hz, 1H), 4.72 (ABq, J=12.5 Hz, Δδ=0.22, 2H), 5.14 (d, J=3.7 Hz, 1H), 5.29 (t, J=6.2 Hz, 2H), 5.51 (d, J=3.3 Hz, 1H), 5.57 (s, 1H), 5.62 (d, J=6.8 Hz, 1H), 6.68–6.72 (M, 1H), 7.30–7.34 (m, 2H), 7.34–7.38 (m, 3H), 7.41–7.46 (m, 2H), 7.52 (d, J=8.1 Hz, 1H), 7.62 (s, 1H), 7.94 (t, J=0.9 Hz, 1H), 9.88 (s, 1H); IR (KBr) 3390, 2920, 2850, 1680, 1600, 1590, 1530, 1455, 1430, 1385, 1320, 1280, 1140, 1070, 1050, 1025, and 750 cm$^{-1}$; mass spectrum [(−) FAB], m/z 662 (M−H)$^-$; Anal. Calcd. for C$_{31}$H$_{34}$ClNO$_{13}$.1.0 H$_2$O: C, 54.59; H, 5.32; N, 2.05, Found: C, 54.82; H, 4.91; N, 2.03.

EXAMPLE 64

Furan-2-carboxylic acid {5-[(6-O-benzoyl-4',6'-O-benzylidene-β-D-maltosyl)-oxy-methyl]-2-chloro-phenyl}-amide The title compound was prepared as a white solid (0.130 g, 47%) from furan-2-carboxylic acid {5-[(4',6'-O-benzylidene-β-D-maltosyl)-oxy-methyl]-2-chloro-phenyl}-amide using a procedure similar to Example 2, mp >142° C. (decomp.); $^1$H NMR (DMSO-d$_6$) δ3.16–3.23 (m, 1H), 3.27–3.42 (m, 2H), 3.49–3.64 (m, 4H), 3.71 (dd, J=5.1, 10.1 Hz, 1H), 3.75–3.80 (m, 1H), 4.05 (dd, J=4.8, 9.9 Hz, 1H), 4.36 (dd, J=5.3, 12.3 Hz, 1H), 4.42 (d, J=7.9 Hz, 1H), 4.58–4.63 (m, 2H), 4.78 (d, J=12.7 Hz, 1H), 5.14 (d, J=3.7 Hz, 1H), 5.34 (d, J=5.3 Hz, 1H), 5.38 (d, J=5.3 Hz, 1H), 5.52 (s, 1H), 5.58 (d, J=2.9 Hz, 1H), 5.79 (d, J=6.2 Hz, 1H), 6.69 (q, J=1.8 Hz, 1H), 7.26–7.32 (m, 2H), 7.33–7.38 (m, 3H), 7.38–7.44 (m, 2H), 7.47 (d, J=8.3 Hz, 1H), 7.51 (t, J=7.9 Hz, 2H), 7.61 (d, J=2.0 Hz, 1H), 7.61–7.66 (m, 1H), 7.93 (dd, J=0.7, 2.6 Hz, 1H), 7.99 (dd, J=5.3, 7.0 Hz, 2H), 9.85 (s, 1H); IR (KBr) 3460, 3380, 3140, 3080, 2880, 1730, 1660, 1590, 1535, 1445, 1425, 1375, 1320, 1275, 1140, 1120, 1075, 1025, 980, and 715 cm$^{-1}$; mass spectrum [(+) ESI], m/z 768 (M+H)$^+$, 790 (M+Na)$^+$; Anal. Calcd. for C$_{38}$H$_{38}$ClNO$_{14}$.1.0 H$_2$O: C, 58.05; H, 5.13; N, 1.78, Found: C, 57.96; H, 4.93; N, 1.76.

EXAMPLE 65

N-{2-Chloro-5-[(4',6'-O-benzylidene-β-D-maltosyl)-oxy-methyl]-phenyl}-pent-4-enamide Step 1

N-[2-Chloro-5-[[[2,3,6-tri-O-acetyl-4-O-(2,3,4,6-tetra-O-acetyl-α-D-glucopyranosyl)-β-D-glucopyranosyl]oxy]methyl]phenyl]-4-pentenamide To a stirred solution of 4-pentenoic acid (57.9 μL, 0.567 mmol) and DMF (cat. amt.) in CH$_2$Cl$_2$ (3 mL) at rt was added oxalyl chloride (49.4 μL, 0.567 mmol) dropwise. After 5 min. at this temperature, it was heated to 40° C. for an additional 10 min. This completed the preparation of the acid chloride starting material. At this point, to a second stirred solution of NaH (0.0206 g, 0.515 mmol) and CH$_2$Cl$_2$ (3 mL) at rt was added 2-chloro-5-(hepta-O-acetyl-β-D- maltosyl-oxymethyl)-phenylamine (0.400 mg, 0.515 mmol). After 10 min., the acid chloride solution was added to this solution dropwise. The reaction was stirred at rt for 1 h and then diluted with EtOAc (100 mL). This layer was washed with 1N HCl (10 mL), sat. NaHCO$_3$ (10 mL), and brine (10 mL) and then dried (MgSO$_4$). After concentration, the oilly residue was purified by flash chromatography (10:90 to 70:30 EtOAc:petroleum ether gradient) to afford the product (0.321 g, 73%) as a white foam, mp >68° C. (decomp.); $^1$H NMR (DMSO-d$_6$) δ1.93 (s, 3H), 1.94 (s, 6H), 1.969 (s, 3H), 1.972 (s, 3H), 2.01 (s, 3H), 2.08 (s, 3H), 2.29–2.36 (m, 2H), 2.44–2.49 (m, 2H), 3.92–4.02 (m, 4H), 4.13–4.22 (m, 2H), 4.38 (d, J=10.1 Hz, 1H), 4.53 (d, J=12.7 Hz, 1H), 4.69–4.75 (m, 2H), 4.84 (d, J=3.7 Hz, 1H), 4.87 (d, J=2.9 Hz, 1H), 4.94–5.01 (m, 2H), 5.07 (dd, J=2.0, 17.4 Hz, 1H), 5.21 (t, J=9.7 Hz, 1H), 5.27 (d, J=3.7 Hz, 1H), 5.31 (d, J=8.8 Hz, 1H), 5.80–5.91 (m, 1H), 7.08 (dd, J=2.0, 8.3 Hz, 1H), 7.46 (d, J=8.1 Hz, 1H), 7.61 (s, 1H), 9.49 (s, 1H); IR (KBr) 3400, 2950, 1755, 1690, 1630, 1590, 1525, 1420, 1370, 1235, and 1050 cm$^{-1}$; mass spectrum [(+) FAB], m/z 858/860 (M+H)$^+$, 880/882 (M+Na)$^+$, Anal. Calcd. for C$_{38}$H$_{48}$ClNO$_{19}$·0.5 H$_2$O: C, 52.63; H, 5.69; N, 1.62, Found: C, 52.65; H, 5.66; N, 1.59.

Step 2

N-{2-Chloro-5-[(β-D-maltosyl)-oxy-methyl]-phenyl}-pent-4-enylamide

The title compound was prepared as an off-white solid (0.0614 g, 93%) from N-[2-chloro-5-[[[2,3,6-tri-O-acetyl-4-O-(2,3,4,6-tetra-O-acetyl-α-D-glucopyranosyl)-β-D-glucopyranosyl]oxy]methyl]phenyl]-4-pentenamide and a procedure similar to step 4 of Example 1, mp >103° C. (decomp.); $^1$H NMR (DMSO-d$_6$) δ2.30–2.37 (m, 2H), 2.43–2.49 (m, 2H), 3.02–3.10 (m, 2H), 3.19–3.28 (m, 2H), 3.30–3.49 (m, 5H), 3.54–3.63 (m, 2H), 3.72 (d, J=10.8 Hz, 1H), 4.28 (d, J=7.7 Hz, 1H), 4.40–4.67 (m, 2H), 4.54 (d, J=12.3 Hz, 1H), 4.72–4.96 (m, 2H), 4.80 (d, J=12.3 Hz, 1H), 4.96–5.04 (m, 2H), 5.08 (dd, J=1.5, 17.1 Hz, 1H), 5.13–5.33 (bs, 1H), 5.33–5.59 (bs, 2H), 5.80–5.92 (m, 1H), 7.22 (dd, J=1.5, 8.1 Hz, 1H), 7.44 (d, J=8.1 Hz, 1H), 7.63 (s, 1H), 9.51 (s, 1H); IR (KBr) 3400, 2910, 1665, 1590, 1530, 1440, 1420, 1370, 1310, 1140, 1070, and 1035 cm$^{-1}$; mass spectrum [(+) FAB], m/z 564/566 (M+H)$^+$, 586/588 (M+Na)$^+$, Anal. Calcd. for C$_{24}$H$_{34}$ClNO$_{12}$: C, 51.11; H, 6.06; N, 2.48, Found: C, 51.17; H, 6.06; N, 2.36.

Step 3

N-{2-Chloro-5-[(4',6'-O-benzylidene-β-D-maltosyl)-oxy-methyl]-phenyl}-pent-4-enamide The title compound was prepared as a white powder (0.1502 g, 88%) from N-{2-chloro-5-[(β-D-maltosyl)-oxy-methyl]-phenyl}-pent-4-enylamide using a procedure similar to Example 24, mp 191–193° C.; $^1$H NMR (DMSO-d$_6$) δ2.30–2.37 (m, 2H), 2.43–2.49 (m, 2H), 3.06–3.13 (m, 1H), 3.28–3.33 (m, 1H), 3.34–3.41 (m, 3H), 3.43–3.49 (m, 1H), 3.51–3.60 (m, 2H), 3.64–3.75 (m, 3H), 4.11 (dd, J=2.9, 8.1 Hz, 1H), 4.30 (d, J=7.7 Hz, 1H), 4.67 (t, J=5.9 Hz, 1H), 4.68 (ABq, J=12.3 Hz, Δδ=0.22, 2H), 4.99 (dd, J=2.0, 10.3 Hz, 1H), 5.08 (dd, J=1.8, 17.1 Hz, 1H), 5.14 (d, J=3.7 Hz, 1H), 5.25 (d, J=5.3 Hz, 1H), 5.30 (d, J=5.3 Hz, 1H), 5.51 (d, J=3.3 Hz, 1H), 5.57 (s, 1H), 5.63 (d, J=6.6 Hz, 1H), 5.81–5.91 (m, 1H), 7.23 (dd, J=2.0, 8.3 Hz, 1H), 7.34–7.38 (m, 3H), 7.42–7.47 (m, 3H), 7.64 (d, J=1.5 Hz, 1H), 9.51 (s, 1H); IR (KBr) 3410, 2900, 2870, 1670, 1640, 1590, 1535, 1445, 1420, 1375, 1370, 1325, 1310, 1270, 1150, 1070, and 1030 cm$^{-1}$; mass spectrum [(+) FAB], m/z 652/654 (M+H)$^+$, 674/676 (M+Na)$^+$; Anal. Calcd. for C$_{31}$H$_{38}$ClNO$_{12}$: C, 57.10; H, 5.87; N, 2.15, Found: C, 56.76; H, 5.81; N, 2.31.

EXAMPLE 66

N-{2-Chloro-5-[(6-O-benzoyl-4',6'-O-benzilidene-β-D-maltosyl)-oxy-methyl]-phenyl}-pent-4-enamide The title compound was prepared as a white solid (1.10 g, 84%) from N-{2-chloro-5-[(4',6'-O-benzylidene-β-D-maltosyl)-oxy-methyl]-phenyl}-pent-4-enamide using a procedure similar to Example 2, mp >110° C. (decomp.); $^1$H NMR (DMSO-d$_6$) δ2.28–2.35 (m, 2H), 2.41–2.46 (m, 2H), 3.16–3.23 (m, 1H), 3.28–3.43 (m, 2H), 3.48–3.64 (m, 4H), 3.68–3.73 (m, 1H), 3.73–3.79 (m, 1H), 4.03–4.08 (m, 1H), 4.33–4.38 (m, 1H), 4.39 (d, J=7.7 Hz, 1H), 4.58–4.63 (m, 1H), 4.65 (ABq, J=12.5 Hz, Δδ=0.14, 2H), 4.95–4.99 (m, 1H), 5.06 (dd, J=2.0, 17.4 Hz, 1H), 5.13 (d, J=4.0 Hz, 1H), 5.35 (t, J=4.8 Hz, 2H), 5.52 (s, 1H), 5.57 (d, J=2.9 Hz, 1H), 5.80 (d, J=6.4 Hz, 1H), 5.81–5.90 (m, 1H), 7.20 (dd, J=2.0, 8.1 Hz, 1H), 7.33–7.37 (m, 3H), 7.38–7.43 (m, 3H), 7.50–7.55 (m, 2H), 7.62 (d, J=1.5 Hz, 1H), 7.63–7.68 (m, 1H), 7.99 (dd, J=1.1, 8.3 Hz, 2H), 9.49 (s, 1H); IR (KBr) 3400, 3270, 3080, 2910, 2880, 1725, 1660, 1590, 1530, 1445, 1425, 1375, 1325, 1275, 1140, 1070, 1025, 990, and 715 cm$^{-1}$; mass spectrum [(+) FAB], m/z 756/758 (M+H)$^+$, 778/780 (M+Na)$^+$; Anal. Calcd. for C$_{38}$H$_{42}$ClNO$_{13}$·0.5 H$_2$O: C, 59.65; H, 5.66; N, 1.83, Found: C, 59.73; H, 5.64; N, 1.75.

EXAMPLE 67

5-(6-O-Benzoyl-4',6'-O-benzylidene-β-D-maltosyl)-oxy-methyl-2-chloro-phenylamine To a stirred solution of N-{2-chloro-5-[(6-O-benzoyl-4',6'-O-benzilidene-β-D-maltosyl)-oxy-methyl]-phenyl}-pent-4-enamide (0.681 g, 0.901 mmol) in THF:H$_2$O (1:1, 50 mL) at rt was added iodine (0.685 g, 2.70 mmol). After 5 min. at this temperature, it was quenched with solid Na$_2$S$_2$O$_3$ until brown color went clear. The mixture was diluted with EtOAc (100 mL), washed with brine (10 mL), and then dried (Na$_2$SO$_4$). After concentration, the oilly residue was purified by flash chromatography (1:99 to 13:87 MeOH:CHCl$_3$ gradient) to afford the product (0.483 g, 80%) as a white solid, mp 168–171° C.; $^1$H NMR (DMSO-d$_6$) δ3.17 (t, J=8.3 Hz, 1H), 3.31–3.43 (m, 2H), 3.48–3.63 (m, 4H), 3.68–3.77 (m, 2H), 4.05 (dd, J=4.8, 9.9 Hz, 1H), 4.32–4.38 (m, 2H), 4.52 (ABq, J=11.9 Hz, Δδ=0.18, 2H), 4.61 (d, J=10.5 Hz, 1H), 5.14 (d, J=3.7 Hz, 1H), 5.22–5.32 (bs, 3H), 5.32–5.39 (bs, 1H), 5.52 (s, 1H), 5.57 (s, 1H), 5.76–5.83 (bs, 1H), 6.53 (dd, J=1.8, 8.1 Hz, 1H), 6.75 (d, J=2.0 Hz, 1H), 7.08 (7.9 Hz, 1H), 7.33–7.37 (m, 3H), 7.38–7.44 (m, 2H), 7.51–7.56 (m, 2H), 7.63–7.68 (m, 1H), 8.00 (dd, J=0.7, 7.9 Hz, 2H); IR (KBr) 3390, 2920, 2860, 1730, 1620, 1590, 1495, 1440, 1430, 1370, 1315, 1270, 1070, 1025, 1000, and 710 cm$^{-1}$; mass spectrum [(+) FAB], m/z 674/676 (M+H)$^+$, 696/698 (M+Na)$^+$; Anal. Calcd. for C$_{33}$H$_{36}$ClNO$_{12}$·1.0 H$_2$O: C, 57.27; H, 5.53; N, 2.02, Found: C, 57.28; H, 5.39; N, 1.99.

EXAMPLE 68

(4-Chloro)-benzyl-4',6'-O-benzylidene-β-D-maltoside

Step 1

(4-Chloro-benzyl)-2,2',3,3',4',6,6'-hepta-O-acetyl-β-D-maltoside

The title compound was prepared as white needles (3.96 g, 73%) from acetobromomaltose using 4-chloro-benzyl alcohol and a procedure similar to step 1 of Example 1, mp 138–141° C.; $^1$H NMR (DMSO-d$_6$) δ1.994 (s, 3H), 1.999 (s, 3H), 2.00 (s, 3H), 2.025 (s, 3H), 2.029 (s, 3H), 2.10 (s, 3H), 2.16 (s, 3H), 3.66 (ddd, J=2.9, 4.4, 9.9 Hz, 1H), 3.96 (ddd, J=2.4, 4.0, 10.1 Hz, 1H), 4.00–4.07 (m, 2H), 4.21–4.28 (m, 2H), 4.51 (dd, J=2.9, 12.3 Hz, 1H), 4.56 (d, J=2.4 Hz, 1H), 4.58 (d, J=6.8 Hz, 1H), 4.80–4.92 (m, 3H), 5.05 (t, J=9.9 Hz, 1H), 5.22 (t, J=9.2 Hz, 1H), 5.35 (dd, J=9.4, 10.3 Hz, 1H), 5.41 (d, J=4.0 Hz, 1H), 7.21 (d, J=8.6 Hz, 2H), 7.32 (d, J=8.3 Hz, 2H); IR (KBr) 3480, 2960, 2880, 1755, 1650, 1610, 1495, 1440, 1375, 1335, 1240, 1170, 1135, 1050, 935, 910, 820, and 615 cm$^{-1}$; mass spectrum [(+) FAB], m/z 761/763 (M+H)$^+$, 783/785 (M+Na)$^+$, Anal. Calcd. for C$_{33}$H$_{41}$ClO$_{18}$: C, 52.08; H, 5.43; N, 0.00, Found: C, 51.88; H, 5.37; N, 0.01.

Step 2

(4-Chloro-benzyl)-β-D-maltoside

The title compound was prepared as a white foam (1.55 g, 95%) from (4-chloro-benzyl)-2,2',3,3',4',6,6'-hepta-O-acetyl-β-D-maltoside using a procedure similar to step 4 of Example 1, mp >102° C. (decomp.); $^1$H NMR (DMSO-d$_6$) δ3.02–3.11 (m, 2H), 3.19–3.26 (m, 2H), 3.29–3.36 (m, 2H), 3.37–3.49 (m, 3H), 3.54–3.64 (m, 2H), 3.72 (d, J=11.0 Hz, 1H), 4.27 (d, J=7.7 Hz, 1H), 4.39–4.65 (bs, 2H), 4.69 (ABq, J=12.5 Hz, Δδ=0.20, 2H), 4.76–5.03 (bs, 1H), 5.01 (d, J=3.7 Hz, 1H), 5.10–5.63 (bs, 4H), 7.37–7.43 (m, 4H); IR (KBr) 3340, 2920, 2890, 1625, 1600, 1490, 1450, 1400, 1365, 1150, 1075, 1030, and 820 cm$^{-1}$; mass spectrum [(+) ESI], m/z 484.4/486.4 (M+NH$_4$)$^+$, Anal. Calcd. for C$_{19}$H$_{27}$ClO$_{11}$.0.5 H$_2$O: C, 47.96; H, 5.93; N, 0.00, Found: C, 47.62; H, 5.82; N, 0.24.

Step 3

(4-Chloro)-benzyl-4',6'-O-benzylidene-β-D-maltoside

The title compound was prepared as a white foam (1.20 g, 65%) from (4-chloro-benzyl)-β-D-maltoside using a procedure similar to Example 24, mp 187–188° C.; $^1$H NMR (DMSO-d$_6$) δ3.10 (t, J=8.3 Hz, 1H), 3.27–3.41 (m, 4H), 3.46 (t, J=8.8 Hz, 1H), 3.51–3.59 (m, 2H), 3.64–3.75 (m, 3H), 4.12 (dd, J=3.1, 8.1 Hz, 1H), 4.29 (d, J=7.7 Hz, 1H), 4.62–4.71 (bs, 1H), 4.70 (ABq, J=12.5 Hz, Δδ=0.20, 2H), 5.14 (d, J=3.7 Hz, 1H), 5.21–5.36 (bs, 2H), 5.47–5.55 (bs, 1H), 5.57 (s, 1H), 5.59–5.67 (bs, 1H), 7.34–7.39 (m, 3H), 7.39–7.46 (m, 6H); IR (KBr) 3570, 3430, 3080, 2870, 1615, 1495, 1450, 1435, 1375, 1360, 1340, 1255, 1160, 1120, 1070, 1030, 1000, and 755 cm$^{-1}$; mass spectrum [(+) ESI], m/z 555/557 (M+H)$^+$, 572/574 (M+NH$_4$)$^+$, 1126/1128 (2M+NH$_4$)$^+$; Anal. Calcd. for C$_{26}$H$_{31}$ClO$_{11}$: C, 56.27; H, 5.63; N, 0.00, Found: C, 56.09; H, 5.73; N, 0.23.

EXAMPLE 69

Benzoic acid 1-O-(4-chloro)-benzyl-4',6'-O-benzylidene-6-deoxy-β-D-malto-6-yl ester The title compound was prepared as a white solid (0.800 g, 66%) from (4-chloro)-benzyl-4',6'-O-benzylidene-β-D-maltoside using a procedure similar to Example 2, mp >110° C. (decomp.); $^1$H NMR (DMSO-d$_6$) δ3.16–3.23 (m, 1H), 3.27–3.43 (m, 2H), 3.49–3.64 (m, 4H), 3.68–3.78 (m, 2H), 4.02–4.08 (m, 1H), 4.35 (dd, J=5.5, 12.5 Hz, 1H), 4.39 (d, J=7.9 Hz, 1H), 4.57–4.62 (m, 1H), 4.67 (ABq, J=12.5 Hz, Δδ=0.14, 2H), 5.14 (d, J 3.7 Hz, 1H), 5.36 (dd, J=5.1, 10.5 Hz, 2H), 5.52 (s, 1H), 5.58 (d, J=2.9 Hz, 1H), 5.80 (d, J=6.2 Hz, 1H), 7.33–7.43 (m, 9H), 7.53 (t, J=7.5 Hz, 2H), 7.66 (td, J=1.1, 7.7 Hz, 1H), 7.99 (dd, J=0.9, 8.1 Hz, 2M); IR (KBr) 3410, 2890, 1725, 1630, 1610, 1495, 1440, 1380, 1320, 1275, 1075, 1025, and 710 cm$^{-1}$; mass spectrum [(−) FAB], m/z 657/659 (M−H)$^-$; Anal. Calcd. for C$_{33}$H$_{35}$ClO$_{12}$.1.0 H$_2$O: C, 58.54; H, 5.51; N, 0.00, Found: C, 58.75; H, 5.36; N, 0.14.

EXAMPLE 70

4-Benzoyl-N-{5-[(4',6'-O-benzylidene-β-D-maltosyl)-oxy-methyl]-2-chloro-phenyl}-benzamide Step 1

4-Benzoyl-N-{2-chloro-5-[(2,2',3,3',4',6,6'-hepta-O-acetyl-β-D-maltosyl)-oxy-methyl]-phenyl}-benzamide The title compound was prepared as a white foam (0.240 g, 94%) from 2-chloro-5-(hepta-O-acetyl-β-D-maltosyl-oxymethyl)-phenylamine using p-benzoylbenzoic acid and a procedure similar to step 1 of Example 65, mp >84° C. (decomp.); $^1$H NMR (DMSO-d$_6$) δ1.93 (s, 3H), 1.94 (s, 6H), 1.97 (s, 6H), 2.01 (s, 3H), 2.08 (s, 3H), 3.93–4.03 (m, 4H), 4.15 (dd, J=4.6, 12.3 Hz, 1H), 4.21 (dd, J=4.6, 12.1 Hz, 1H), 4.39 (dd, J=2.2, 11.9 Hz, 1H), 4.70 (ABq, J=12.7 Hz, Δδ=0.14, 2H), 4.74 (dd, J=8.1, 9.7 Hz, 1H), 4.86 (dd, J=4.0, 10.5 Hz, 1H), 4.90 (d, J=8.1 Hz, 1H), 4.98 (t, J=9.7 Hz, 1H), 5.21 (dd, J=9.7, 10.5 Hz, 1H), 5.28 (d, J=4.0 Hz, 1H), 5.31 (dd, J=8.6, 9.4 Hz, 1H), 7.22 (dd, J=2.0, 8.3 Hz, 1H), 7.52 (d, J=2.0 Hz, 1H), 7.55–7.62 (m, 3H), 7.69–7.74 (m, 1H), 7.76–7.80 (m, 2H), 7.85–7.88 (m, 2H), 8.11–8.14 (m, 2H), 10.30 (s, 1H); IR (KBr) 3400, 3010, 2950, 1755, 1675, 1650, 1590, 1530, 1440, 1420, 1370, 1230, 1130, and 1040 cm$^{-1}$; mass spectrum [(+) FAB], m/z 984/986 (M+H)$^+$, 1006/1008 (M+Na)$^+$, Anal. Calcd. for C$_{47}$H$_{50}$ClNO$_{20}$: C, 57.35; H, 5.12; N, 1.42, Found: C, 57.11; H, 5.03; N, 1.32.

Step 2

4-Benzoyl-N-{2-chloro-5-[3,4-dihydroxy-6-hydroxymethyl-5-(3,4,5-trihydroxy-6-hydroxymethyl-tetrahydro-pyran-2-yloxy)-tetrahydro-pyran-2-yloxymethyl]-phenyl}-benzamide The title compound was prepared as a off-white glassy solid (1.50 g, 95%) from 4-benzoyl-N-{2-chloro-5-[(2,2',3,3',4',6,6'-hepta-O-acetyl-β-D-maltosyl)-oxy-methyl]-phenyl}-benzamide using a procedure similar to step 4 of Example 1, mp >131° C. (decomp.); $^1$H NMR (DMSO-d$_6$) δ3.02–3.32 (m, 4H), 3.32–3.40 (m, 2H), 3.40–3.50 (m, 3H), 3.55–3.64 (m, 2H), 3.73 (d, J=10.8 Hz, 1H), 4.31 (d, J=7.9 Hz, 1H), 4.48–4.53 (bs, 1H), 4.53–4.59 (bs, 1H), 4.61 (d, J=12.5 Hz, 1H), 4.83–4.92 (m, 3H), 5.02 (d, J=4.0 Hz, 1H), 5.21–5.31 (bs, 1H), 5.36–5.48 (bs, 1H), 5.48–5.56 (bs, 1H), 7.32 (dd, J=2.0, 8.3 Hz, 1H), 7.53 (d, J=8.1 Hz, 1H), 7.56–7.62 (m, 3H), 7.69–7.74 (m, 1H), 7.78 (dd, J=1.3, 8.3 Hz, 2H), 7.86 (d, J=8.6 Hz, 2H), 8.14 (d, J=8.6 Hz, 2H), 10.33 (s, 1H); IR (KBr) 3410, 2910, 1660, 1590, 1530, 1440, 1420, 1370, 1325, 1275, 1140, 1100, 1080, 1030, 910, and 710 cm$^{-1}$; mass spectrum [(+) FAB], m/z 690/692 (M+H)$^+$, 712/714 (M+Na)$^+$, Anal. Calcd. for C$_{33}$H$_{36}$ClNO$_{13}$.1.0 H$_2$O: C, 55.97; H, 5.41; N, 1.98, Found: C, 55.98; H, 5.36; N, 1.97.

Step 3

4-Benzoyl-N-{5-[(4',6'-O-benzylidene-β-D-maltosyl)-oxy-methyl]-2-chloro-phenyl}-benzamide The title compound was prepared as a white solid (1.07 g, 66%) from 4-benzoyl-N-{2-chloro-5-[3,4-dihydroxy-6- hydroxymethyl-5-(3,4,5-trihydroxy-6-hydroxymethyl-tetrahydro-pyran-2-yloxy)-tetrahydro-pyran-2-yloxymethyl]-phenyl}-benzamide using a procedure similar to Example 24, mp 208–211° C.; $^1$H NMR (DMSO-$d_6$) δ3.09–3.15 (m, 1H), 3.29–3.42 (m, 4H), 3.47 (td, J=3.1, 8.8 Hz, 1H), 3.52–3.60 (m, 2H), 3.64–3.76 (m, 3H), 4.12 (dd, J=3.1, 8.3 Hz, 1H), 4.34 (d, J=7.7 Hz, 1H), 4.68 (t, J=7.5 Hz, 1H), 4.75 (ABq, J=12.5 Hz, Δδ=0.22, 2H), 5.14 (d, J=4.0 Hz, 1H), 5.30 (dd, J=1.8, 5.3 Hz, 2H), 5.52 (d, J=3.3 Hz, 1H), 5.57 (s, 1H), 5.63 (d, J=6.6 Hz, 1H), 7.34–7.38 (m, 4H), 7.42–7.46 (m, 2H), 7.55 (d, J=8.1 Hz, 1H), 7.56–7.62 (m, 3H), 7.69–7.74 (m, 1H), 7.76–7.80 (m, 2H), 7.87 (d, J=8.3 Hz, 2H), 8.14 (d, J=8.3 Hz, 2H), 10.33 (s, 1H); IR (KBr) 3410, 3070, 2920, 2860, 1655, 1590, 1530, 1445, 1425, 1380, 1330, 1275, 1145, 1070, 1030, 1000, 910, and 700 cm$^{-1}$; mass spectrum [(+) FAB], m/z 778/780 (M+H)$^+$, 800/802 (M+Na)$^+$; Anal. Calcd. for $C_{40}H_{40}ClNO_{13}$.0.5 $H_2O$: C, 61.03; H, 5.25; N, 1.78, Found: C, 61.11; H, 4.86; N, 1.74.

EXAMPLE 71

4-Benzoyl-N-{5-[(6-benzoyl-oxy-4',6'-O-benzylidene-β-D-maltosyl)-oxy-methyl]-2-chloro-phenyl}-benzoic acid amide The title compound was prepared as a white solid (0.352 g, 63%) from 4-benzoyl-N-{5-[(4',6'-O-benzylidene-β-D-maltosyl)-oxy-methyl]-2-chloro-phenyl}-benzamide using a procedure similar to Example 2, mp >135° C. (decomp.); $^1$H NMR (DMSO-$d_6$) δ3.18–3.24 (m, 1H), 3.32–3.43 (m, 2H), 3.50–3.65 (m, 4H), 3.72 (td, J=5.3, 10.1 Hz, 1H), 3.77–3.82 (m, 1H), 4.05 (dd, J=4.8, 10.1 Hz, 1H), 4.36 (dd, J=4.8, 12.1 Hz, 1H), 4.43 (d, J=7.9 Hz, 1H), 4.62 (d, J=10.3 Hz, 1H), 4.72 (ABq, J=12.7 Hz, Δδ=0.14, 2H), 5.14 (d, J=3.7 Hz, 1H), 5.32–5.37 (m, 1H), 5.40 (d, J=4.4 Hz, 1H), 5.52 (s, 1H), 5.59 (s, 1H), 5.80 (d, J=5.5 Hz, 1H), 7.31–7.37 (m, 4H), 7.39–7.43 (m, 2H), 7.48–7.53 (m, 3H), 7.56–7.66 (m, 4H), 7.71 (tt, J=1.1, 6.8 Hz, 1H), 7.77 (dd, J=1.1, 7.9 Hz, 2H), 7.85 (d, J=8.6 Hz, 2H), 7.99 (dd, J=0.9, 8.1 Hz, 2H), 8.12 (d, J=8.6 Hz, 2H), 10.33 (s, 1H); IR (KBr) 3420, 3080, 2850, 1720, 1660, 1600, 1530, 1440, 1420, 1370, 1320, 1275, 1140, 1070, 1030, and 715 cm$^{-1}$; mass spectrum [(+) FAB], m/z 882 (M+H)$^+$, 904/906 (M+Na)$^+$; Anal. Calcd. for $C_{47}H_{44}ClNO_{14}$.1.0 $H_2O$: C, 62.70; H, 5.15; N, 1.56, Found: C, 62.83; H, 5.02; N, 1.70.

EXAMPLE 72

4-Benzoyl-N-{5-[(4',6'-O-benzylidene-6-O-(2-iodo)-benzoyl-β-D-maltosyl)-oxy-methyl]-2-chloro-phenyl}-benzamide The title compound was prepared as a white solid (0.145 g, 32%) from 4-benzoyl-N-{5-[(4',6'-O-benzylidene-β-D-maltosyl)-oxy-methyl]-2-chloro-phenyl}-benzamide using o-I-BzCl and a procedure similar to Example 2, mp >122° C. (decomp.); $^1$H NMR (DMSO-$d_6$) δ3.16–3.23 (m, 1H), 3.28–3.45 (m, 2H), 3.49–3.67 (m, 4), 3.75 (dd, J=4.8, 7.5 Hz, 1H), 3.78–3.84 (m, 1H), 4.14 (dd, J=4.6, 9.7 Hz, 1H), 4.36 (dd, J=5.5, 12.1 Hz, 1H), 4.44 (d, J=7.7 Hz, 1H), 4.61–4.67 (m, 1H), 4.73 (ABq, J=12.7 Hz, Δδ=0.15, 2H), 5.16 (d, J=4.0 Hz, 1H), 5.38 (dd, J=5.3, 10.5 Hz, 2H), 5.55 (s, 1H), 5.60 (d, J=2.6 Hz, 1H), 5.88 (d, J=6.2 Hz, 1H), 7.26 (td, J=1.8, 7.9 Hz, 1H), 7.31–7.38 (m, 4H), 7.40–7.45 (m, 2H), 7.48–7.53 (m, 2H), 7.56–7.62 (m, 3H), 7.71 (tt, J=1.3, 6.8 Hz, 1H), 7.75–7.79 (m, 3H), 7.85 (d, J=1.8, 6.6 Hz, 2H), 8.00 (dd, J=1.1, 8.1 Hz, 1H), 8.12 (d, J=1.8, 6.6 Hz, 2H), 10.30 (s, 1H); IR (KBr) 3410, 3070, 2850, 1730, 1655, 1590, 1525, 1440, 1420, 1375, 1280, 1250, 1140, 1070, 1025, and 705 cm$^{-1}$; mass spectrum [(+) FAB], m/z 1008 (M+H)$^+$, 1030 (M+Na)$^+$; Anal. Calcd. for $C_{47}H_{43}ClINO_{14}$.0.5 $H_2O$: C, 55.50; H, 4.36; N, 1.38, Found: C, 55.14; H, 4.22; N, 1.36.

EXAMPLE 73

4-Benzoyl-N-{5-[(4',6'-O-benzylidene-6-O-(3-iodo-benzoyl)-β-D-maltosyl)-oxy-methyl]-2-chloro-phenyl}-benzamide The title compound was prepared as a white solid (0.244 g, 54%) from 4-benzoyl-N-{5-[(4',6'-O-benzylidene-β-D-maltosyl)-oxy-methyl]-2-chloro-phenyl}-benzamide using m-I-BzCl (prepared from m-I-benzoic acid and oxalyl chloride) and a procedure similar to Example 2, mp 185–188.5° C.; $^1$H NMR (DMSO-$d_6$) δ3.18–3.24 (m, 1H), 3.27–3.43 (m, 2H), 3.50–3.63 (m, 4H), 3.71 (td, J=4.6, 9.9 Hz, 1H), 3.77–3.82 (m, 1H), 4.06 (dd, J=4.8, 9.9 Hz, 1H), 4.35 (dd, J=5.5, 12.1 Hz, 1H), 4.44 (d, J=7.7 Hz, 1H), 4.61–4.67 (m, 1H), 4.73 (ABq, J=12.5 Hz, Δδ=0.13, 2H), 5.14 (d, J=4.0 Hz, 1H), 5.34 (d, J=5.3 Hz, 1H), 5.39 (d, J=5.1 Hz, 1H), 4.53 (s, 1H), 5.58 (d, J=2.9 Hz, 1H), 5.79 (d, J=6.2 Hz, 1H), 7.31 (d, J=7.9 Hz, 1H), 7.33–7.37 (m, 4H), 7.38–7.43 (m, 2H), 7.51 (d, J=8.1 Hz, 1H), 7.56–7.62 (m, 3H), 7.71 (tt, J=1.3, 6.8 Hz, 1H), 7.76–7.80 (m, 2H), 7.85 (dd, J=1.8, 6.6 Hz, 2H), 7.99 (dt, J=1.5, 7.7 Hz, 2H), 8.11 (dd, J=1.8, 6.8 Hz, 2H), 8.25 (t, J=1.8 Hz, 1H), 10.29 (s, 1H); IR (KBr) 3410, 3080, 2910, 2850, 1725, 1650, 1590, 1570, 1530, 1440, 1420, 1375, 1280, 1255, 1140, 1070, 1030, 750, and 700 cm$^{-1}$; mass spectrum [(+) FAB], m/z 1030 (M+Na)$^+$; Anal. Calcd. for $C_{47}H_{43}ClINO_{14}$.0.5 $H_2O$: C, 55.50; H, 4.36; N, 1.38, Found: C, 55.13; H 4.15; N, 1.38.

EXAMPLE 74

4-Benzoyl-N-{5-[(4',6'-O-benzylidene-6-(4-iodo-benzoyl)-oxy-β-D-maltosyl)-oxy-methyl]-2-chloro-phenyl}-benzoic acid amide The title compound was prepared as a white solid (0.378 g, 59%) from 4-benzoyl-N-{5-[(4',6'-O-benzylidene-β-D-maltosyl)-oxy-methyl]-2-chloro-phenyl}-benzamide using p-iodobenzoyl chloride and a procedure similar to Example 2, mp >151° C. (decomp.); $^1$H NMR (DMSO-$d_6$) δ3.18–3.24 (m, 1H), 3.32–3.42 (m, 2H), 3.49–3.63 (m, 4H), 3.71 (td, J=4.8, 9.9 Hz, 1H), 3.78 (ddd, J=1.1, 4.6, 9.2 Hz, 1H), 4.04 (dd, J=4.8, 9.9 Hz, 1H), 4.35 (dd, J=4.8, 12.1 Hz, 1H), 4.42 (d, J=7.7 Hz, 1H), 4.59 (d, J=10.8 Hz, 1H), 4.72 (ABq, J=12.7 Hz, Δδ=0.13, 2H), 5.13 (d, J=4.0 Hz, 1H), 5.34 (d, J=5.3 Hz, 1H), 5.39 (d, J=5.1 Hz, 1H), 5.52 (s, 1H), 5.59 (d, J=2.4 Hz, 1H), 5.82 (d, J=5.9 Hz, 1H), 7.31–7.37 (m, 4H), 7.38–7.42 (m, 2H), 7.51 (d, J=8.3 Hz, 1H), 7.56–7.61 (m, 3H), 7.69–7.75 (m, 3H), 7.76–7.79 (m, 2H), 7.85 (d, J=8.6 Hz, 2H), 7.89 (d, J=8.6 Hz, 2H), 8.12 (d, J=8.6 Hz, 2H), 10.30 (s, 1H); IR (KBr) 3420, 3080, 2890, 2840, 1725, 1655, 1590, 1530, 1440, 1420, 1380, 1365, 1325, 1280, 1160, 1120, 1070, 1030, 1005, 750, and 700 cm$^{-1}$; mass spectrum [(+) FAB], m/z 1030/1032 (M+Na)$^+$; Anal. Calcd. for $C_{47}H_{43}ClINO_{14}$: C, 55.01; H, 4.42; N, 1.36, Found: C, 54.99; H, 4.38; N, 1.40.

EXAMPLE 75

(1-{5-[(4',6'-O-Benzylidene-β-D-maltosyl)-oxy-methyl]-2-chloro-phenyl-carbamoyl}ethyl)-carbamic acid 9H-fluoren-9ylmethyl ester Step 1

N-{2-Chloro-5-[(2,2',3,3',4',6,6')-hepta-O-acetyl-β-D-maltosyl-oxymethyl]-phenyl}-(9H-fluoren-9-ylmethoxycarbonyl)-L-alaninamide The title compound was prepared as a white foam (2.50 g, 36%) from 2-chloro-5-(hepta-O-acetyl-β-D-maltosyloxymethyl)-phenylamine using N-(9H-fluoren-9-ylmethyoxycarbonylamino)-L-alanine and a procedure similar to step 1 of Example 65, mp >96° C. (decomp.); $^1$H NMR (DMSO-d$_6$) δ1.33 (dd, J=7.2 Hz, 3H), 1.918 (s, 3H), 1.919 (s, 3H), 1.94 (s, 3H), 1.966 (s, 3H), 1.97 (s, 3H), 2.01 (s, 3H), 2.07 (s, 3H), 3.91–4.02 (m, 4H), 4.12–4.24 (m, 3H), 4.24–4.34 (m, 3H), 4.34–4.40 (m, 1H), 4.53 (d, J=12.7 Hz, 1H), 4.68–4.75 (m, 2H), 4.84 (d, J=4.0 Hz, 1H), 4.86 (d, J=2.6 Hz, 1H), 4.97 (t, J=9.7 Hz, 1H), 5.21 (t, J=9.7 Hz, 1H), 5.27 (d, J=3.7 Hz, 1H), 5.27–5.32 (m, 1H), 7.08 (dd, J=1.8, 8.1 Hz, 1H), 7.32 (t, J=7.2 Hz, 2H), 7.40 (t, J=7.5 Hz, 2H), 7.47 (d, J=8.1 Hz, 1H), 7.69–7.78 (m, 4H), 7.88 (d, J=7.5 Hz, 2H), 9.42 (s, 1H); IR (KBr) 3360, 3010, 2950, 1755, 1590, 1535, 1440, 1420, 1370, 1230, 1050, and 755 cm$^{-1}$; mass spectrum [(+) ESI], m/z 1069.2 M+H)$^+$, 1086.2/1088.2 (M+NH$_4$)$^+$, Anal. Calcd. for C$_{51}$H$_{57}$ClN$_2$O$_{21}$·3.5 H$_2$O: C, 54.09; H, 5.70; N, 2.47, Found: C, 53.67; H, 5.11; N, 2.34.

Step 2

N-[2-Chloro-5-(β-D-maltosyl-oxymethyl)-phenyl]-(9H-fluoren-9-ylmethoxycarbonyl)-L-alaninamide To a stirred solution of KCN (0.032 g, 0.491 mmol) in MeOH (10 mL) at 0° C. was added (1-{5-[(4',6'-O-benzylidene-β-D-maltosyl)-oxy-methyl]-2-chloro-phenyl-carbamoyl}ethyl)-carbamic acid 9H-fluoren-9ylmethyl ester (1.05 g, 0.982 mmol). The reaction mixture was stirred at this temperature for 24 h and then concentrated. The resulting residue was diluted with THF:sat. aq. NaHCO$_3$ (1:1, 20 mL) followed by addition of Fmoc-Cl (0.170 g, 0.658 mmol). This solution was stirred at rt for 0.5 h, and the resulting mixture filtered to remove the solid that formed. The filtrate was concentrated, and the residue was purified by flash chromatgraphy (80:2:1 to 4:2:1 EtOAc:EtOH: H$_2$O) to afford the product (0.600 g, 79%) which was used in the next Step without further purification.

Step 3

(1-{5-[(4',6'-O-Benzylidene-β-D-maltosyl)-oxy-methyl]-2-chloro-phenyl-carbamoyl}ethyl)-carbamic acid 9H-fluoren-9ylmethyl ester The title compound was prepared as a off-white solid (0.295 g, 41%) from N-[2-chloro-5-(β-D-maltosyl-oxymethyl)-phenyl]-(9H-fluoren-9-ylmethoxycarbonyl)-L-alaninamide using a procedure similar to Example 24, mp >190° C. (decomp.); $^1$H NMR (DMSO-d$_6$) δ1.34 (d, J=7.0 Hz, 3H), 3.06–3.14 (m, 1H), 3.28–3.42 (m, 3H), 3.41 (td, J=2.2, 9.2 Hz, 1H), 3.51–3.60 (m, 2H), 3.64–3.76 (m, 4H), 4.11 (dd, J=2.4, 7.7 Hz, 1H), 4.22 (t, J=6.6 Hz, 1H), 4.26–4.35 (m, 4H), 4.67 (t, J=5.7 Hz, 1H), 4.69 (ABq, J=12.5 Hz, Δδ=0.22, 2H), 5.14 (d, J=3.7 Hz, 1H), 5.26 (d, J=4.8 Hz, 1H), 5.31 (d, J=5.1 Hz, 1H), 5.52 (d, J=2.6 Hz, 1H), 5.57 (s, 1H), 5.64 (d, J=6.2 Hz, 1H), 7.24 (d, J=7.7 Hz, 1H), 7.28–7.48 (m, 10H), 7.69–7.79 (m, 4H), 7.88 (d, J=7.5 Hz, 2H), 9.46 (s, 1H); IR (KBr) 3390, 3080, 2920, 2870, 2350, 1705, 1590, 1525, 1445, 1420, 1375, 1340, 1310, 1255, 1140, 1070, 1030, and 740 cm$^{-1}$; mass spectrum [(+) ESI], m/z 880 (M+NH$_4$)$^+$; Anal. Calcd. for C$_{44}$H$_{47}$ClN$_2$O$_{14}$·1.0 H$_2$O: C, 59.96; H, 5.60; N, 3.18, Found: C, 60.23; H, 5.53; N, 3.45.

EXAMPLE 76

N-(9H-Fluoren-9ylmethoxycarbonyl)-N'-{5-[(6-O-benzoyl-4',6'-O-benzylidene-β-D-maltosyl)-oxy-methyl]-2-chloro-phenyl}-L-alaninamide The title compound was prepared as a white solid (0.083 g, 62%) from (1-{5-[(4',6'-O-benzylidene-β-D-maltosyl)-oxy-methyl]-2-chloro-phenylcarbamoyl}ethyl)-carbamic acid 9H-fluoren-9ylmethyl ester using a procedure similar to Example 2, mp 224–226° C.; $^1$H NMR (DMSO-d$_6$) δ1.32 (d, J=7.2 Hz, 3H), 3.19 (t, J=8.3 Hz, 1H), 3.26–3.37 (m, 4H), 3.48–3.63 (m, 3H), 3.70 (dd, J=5.1, 9.9 Hz, 1H), 3.73–3.78 (m, 1H), 4.05 (dd, J=4.8, 9.9 Hz, 1H), 4.21 (t, J=6.8 Hz, 1H), 4.24–4.38 (m, 3H), 4.40 (d, J=7.7 Hz, 1H), 4.56–4.63 (m, 1H), 4.65 (ABq, J=12.5 Hz, Δδ=0.15, 2H), 5.13 (d, J=3.7 Hz, 1H), 5.27–5.41 (bs, 2H), 5.52 (s, 1H), 5.54–5.61 (bs, 1H), 5.75–5.84 (bs, 1H), 7.21 (d, J=8.6 Hz, 1H), 7.28–7.37 (m, 5H), 7.37–7.45 (m, 5H), 7.51 (t, J=7.9 Hz, 2H), 7.63 (t, J=7.5 Hz, 1H), 7.68–7.77 (m, 4H), 7.88 (d, J=7.7 Hz, 2H), 7.98 (d, J=7.2 Hz, 2H), 9.43 (s, 1H); IR (KBr) 3400, 3080, 2920, 2850, 1725, 1590, 1530, 1440, 1420, 1375, 1320, 1275, 1070, 1025, 745, and 715 cm$^{-1}$; mass spectrum [(+) FAB], m/z 989/991 (M+Na)$^+$; Anal. Calcd. for C$_{51}$H$_{51}$ClN$_2$O$_{15}$·1.0 H$_2$O: C, 62.16; H, 5.42; N, 2.84, Found: C, 61.99; H, 5.23; N, 3.06.

EXAMPLE 77

N'-{5-[(6-O-benzoyl-4',6'-O-benzylidene-β-D-maltosyl)-oxy-methyl]-2-chloro-phenyl}-L-alaninamide To a stirred solution of 20% piperidine (2.00 mL, 20.2 mmol) in DMF (10 mL) at rt was added N-(9H-fluoren-9ylmethoxycarbonyl)-N'-{5-[(6-O-benzoyl-4',6'-O-benzylidene-β-D-maltosyl)-oxy-methyl]-2-chloro-phenyl}-L-alaninamnide (0.300 g, 0.256 mmol). After 2 h at this temperature, the solution was concentrated on the high vacuum. The residue was purified by preparatory plate chromatography (10:2:1 EtOAc:EtOH:H$_2$O) to afford the product (0.018 g, 78%) as an off-white solid, mp 131–133° C.; $^1$H NMR (DMSO-d$_6$) δ1.26 (d, J=7.0 Hz, 3H), 3.15–3.22 (m, 1H), 3.26–3.42 (m, 5H), 3.47–3.64 (m, 4H), 3.70 (dd, J=4.6, 9.7 Hz, 1H), 3.73–3.79 (m, 1H), 4.05 (dd, J=4.8, 9.9 Hz, 1H), 4.35 (dd, J=5.1, 12.1 Hz, 1H), 4.40 (d, J=7.7 Hz, 1H), 4.60 (d, J=12.7 Hz, 1H), 4.66 (ABq, J=12.3 Hz, Δδ=0.14, 2H), 5.13 (d, J=3.7 Hz, 1H), 5.34 (dd, J=0.9, 5.3 Hz, 2H), 5.52 (s, 1H), 5.57 (d, J=2.9 Hz, 1H), 5.80 (d, J=6.2 Hz, 1H), 7.15 (dd, J=2.0, 8.1 Hz, 1H), 7.33–7.38 (m, 3H), 7.38–7.45 (m, 3H), 7.53 (t, J=7.7 Hz, 2H), 7.63–7.68 (m, 2H), 7.98 (d, J=1.3 Hz, 1H), 8.00 (s, 1H), 8.20 (s, 1H); IR (KBr) 3410, 2920, 2850, 1720, 1625, 1590, 1525, 1445, 1420, 1375, 1275, 1070, 1025, and 715 cm$^{-1}$; mass spectrum [(+) FAB], m/z 745 (M+H)$^+$, 767 (M+Na)$^+$; Anal. Calcd. for C$_{36}$H$_{41}$ClN$_2$O$_{13}$·2.0 H$_2$O: C, 55.35; H, 5.81; N, 3.59, Found: C, 55.63; H, 5.77; N, 3.23.

EXAMPLE 78

N-{5-[(4',6'-O-Benzylidene-β-D-maltosyl)-oxymethyl]-2-chloro-phenyl}-N-methyl-acetamide Step 1

N-[5-(2,2',3,3',4',6,6'-Hepta-O-acetyl-β-D-maltosyl)-oxy-methyl-2-chloro-phenyl]-N-methyl-acetamide To a stirred solution of N-[2-chloro-5-(hepta-O-acetyl-β-D-maltosyl-oxymethyl)-phenyl]-acetamide (0.100 g, 0.122 mmol) in THF (2.0 mL) at −78° C. was added NaHMSA (0.183 mL, 1.0 M in THF). After 0.5 h at this temperature, methyl iodide (0.0152 mL, 0.244 mmol) was added, and the reaction was warmed to rt for 2 h. At this point, the reaction was diluted with EtOAc (100 mL), washed with 1 N HCl (10 mL), sat. aq. NAHCO$_3$ (10 mL), and brine (10 mL), and then dried (MgSO$_4$). After concentration, the resulting oilly residue was purified by preparatory plate chromatography using 50:50 EtOAc:petroleum ether as the eluant to afford the product (0.0408 g, 40%) as a white foam, mp >252° C. (decomp.); $^1$H NMR (CDCl$_3$) δ1.81 (s, 3H), 2.00 (s, 3H), 2.01 (s, 6H), 2.02 (s, 3H), 2.04 (s, 3H), 2.10 (s, 3H), 2.15 (s, 3H), 3.19 (d, J=2.9 Hz, 3H), 3.67–3.72 (m, 1H), 3.94–3.99 (m, 1H), 4.03 (t, J=9.4 Hz, 1H), 4.07 (d, J=2.2 Hz, 1H), 4.21–4.28 (m, 2H), 4.54 (dd, J=2.9, 12.3 Hz, 1H), 4.59 (d, J=11.6 Hz, 1H), 4.64 (d, J=7.5 Hz, 1H), 4.83–4.93 (m, 3H), 5.06 (t, J=10.1 Hz, 1H), 5.26 (td, J=3.3, 9.0 Hz, 1H), 5.36 (t, J=9.7 Hz, 1H), 5.42 (d, J=4.0 Hz, 1H), 7.20 (d, J=2.0 Hz, 1H), 7.24 (dt, J=2.0, 8.1 Hz, 1H), 7.47 (dd, J=1.1, 8.1 Hz, 1H); IR (KBr) 3470, 2950, 1755, 1620, 1480, 1420, 1380, 1230, 1140, and 1045 cm$^{-1}$; mass spectrum [(+) ESI], m/z 832 (M+H)$^+$, Anal. Calcd. for C$_{36}$H$_{46}$ClNO$_{19}$.1.5 H$_2$O: C, 50.32; H, 5.75; N, 1.63, Found: C, 50.17; H, 5.38; N, 1.67.

Step 2

N-{2-Chloro-5-[(β-D-maltosyl)-oxymethyl]-phenyl}-N-methyl-acetamide

The title compound was prepared as a white solid (0.475 g, 99%) from N-[5-(2,2',3,3',4',6,6'-hepta-O-acetyl-β-D-maltosyl)-oxy-methyl-2-chloro-phenyl]-N-methyl-acetamide using a procedure similar to step 4 of Example 1, mp >96° C. (decomp.); $^1$H NMR (DMSO-d$_6$) δ1.67 (s, 3H), 3.05 (d, J=1.1 Hz, 3H), 3.06–3.14 (m, 1H), 3.18–3.28 (m, 2H), 3.30–3.38 (m, 2H), 3.38–3.49 (m, 4H), 3.53–3.63 (m, 2H), 3.68–3.75 (m, 1H), 4.28 (dd, J=7.9, 9.7 Hz, 1H), 4.48–4.53 (m, 2H), 4.62 (dd, J=3.3, 13.2 Hz, 1H), 4.84 (d, J=13.0 Hz, 1H), 4.89 (dd, J=5.5, 7.7 Hz, 2H), 5.01 (d, J=3.7 Hz, 1H), 5.30 (dd, J=4.8, 7.7 Hz, 1H), 5.42 (dd, J=2.4, 6.2 Hz, 1H), 5.52 (d, J=3.1 Hz, 1H), 7.43 (dt, J=1.8, 8.1 Hz, 1H), 7.57 (s, 1H), 7.60 (d, J=8.3 Hz, 1H); IR (KBr) 3400, 3000, 2910, 1645, 1580, 1480, 1420, 1385, 1320, 1255, 1195, 1145, 1120, 1075, 1035, and 755 cm$^{-1}$; mass spectrum [(+) FAB], m/z 538 (M+H)$^+$, 560 (M+Na)$^+$, Anal. Calcd. for C$_{22}$H$_{32}$ClNO$_{12}$.1.0 H$_2$O: C, 47.53; H, 6.16; N, 2.52, Found: C, 47.18; H, 6.01; N, 2.38.

Step 3

N-{5-[(4',6'-O-Benzylidene-β-D-maltosyl)-oxymethyl]-2-chloro-phenyl}-N-methyl-acetamide The title compound was prepared as a white foam (0.315 g, 63%) from N-{2-chloro-5-[(β-D-maltosyl)-oxymethyl]-phenyl}-N-methyl-acetamide using a procedure similar to Example 24, mp >125° C. (decomp.); $^1$H NMR (DMSO-d$_6$) δ1.68 (d, J=1.3 Hz, 3H), 3.06 (d, J=1.3 Hz, 3H), 3.09–3.16 (m, 1H), 3.28–3.42 (m, 4H), 3.42–3.50 (m, 1H), 3.50–3.60 (m, 2H), 3.64–3.75 (m, 3H), 4.09–4.14 (m, 1H), 4.30 (dd, J=7.7, 10.3 Hz, 1H), 4.60–4.69 (m, 2H), 4.85 (d, J=13.2 Hz, 1H), 5.14 (d, J=4.0 Hz, 1H), 5.30 (d, J=5.1 Hz, 1H), 5.33 (dd, J=5.1, 7.9 Hz, 1H), 5.53 (d, J=3.3 Hz, 1H), 5.57 (s, 1H), 5.63 (dd, J=2.9, 6.8 Hz, 1H), 7.34–7.38 (m, 3H), 7.41–7.46 (m, 3H), 7.58 (s, 1H), 7.60 (d, J=8.3 Hz, 1H); IR (KBr) 3410, 2920, 2860, 1640, 1610, 1580, 1480, 1440, 1410, 1380, 1320, 1185, 1150, 1070, 1030, 955, and 755 cm$^{-1}$; mass spectrum [(−) FAB], m/z 624 (M−H)$^−$; Anal. Calcd. for C$_{29}$H$_{36}$ClNO$_{12}$.2.5 H$_2$O: C, 51.90; H, 6.16; N, 2.09, Found: C, 51.92; H, 5.48; N, 2.09.

EXAMPLE 79

N-{5-[(6-O-Benzoyl-4',6'-O-benzylidene-β-D-maltosyl)-oxymethyl]-2-chloro-phenyl}-N-methyl-acetamide The title compound was prepared as a white solid (0.087 g, 37%) from N-{5-[(4',6'-O-benzylidene-β-D-maltosyl)-oxymethyl]-2-chloro-phenyl}-N-methyl-acetamide using a procedure similar to Example 2, mp 180–183° C.; $^1$H NMR (DMSO-d$_6$) δ1.64 (d, J=4.0 Hz, 3H), 3.02 (s, 3H), 3.17–3.25 (m, 1H), 3.35 (d, J=9.4 Hz, 1H), 3.37–3.43 (m, 1H), 3.49–3.65 (m, 4H), 3.70 (dd, J=4.6, 9.9 Hz, 1H), 3.73–3.79 (m, 1H), 4.04 (d, J=5.1, 9.9 Hz, 1H), 4.34 (ddd, J=2.4, 4.8, 12.1 Hz, 1H), 4.41 (dd, J=7.9, 10.1 Hz, 1H), 4.58 (d, J=11.4 Hz, 1H), 4.72 (ABq, J=12.5 Hz, Δδ=0.12, 2H), 5.14 (d, J=3.7 Hz, 1H), 5.34 (d, J=4.8 Hz, 1H), 5.43 (dd, J=5.3, 7.2 Hz, 1H), 5.52 (s, 1H), 5.59 (d, J=2.6 Hz, 1H), 5.79 (dd, J=2.0, 5.7 Hz, 1H), 7.33–7.37 (m, 3H), 7.38–7.43 (m, 3H), 7.50–7.55 (m, 3H), 7.56 (d, J=8.3 Hz, 1H), 7.63–7.68 (m, 1H), 7.96–8.00 (m, 2H); IR (KBr) 3495, 3400, 3090, 2930, 2890, 1730, 1645, 1600, 1575, 1480, 1445, 1420, 1385, 1360, 1320, 1270, 1200, 1160, 1110, 1070, 1050, 1020, 985, and 715 cm$^{31}$; mass spectrum [(+) FAB], m/z 730 (M+H)$^+$, 752 (M+Na)$^+$; Anal. Calcd. for C$_{36}$H$_{40}$ClNO$_{13}$.H$_2$O: C, 59.22; H, 5.52; N, 1.92, Found: C, 59.02; H, 5.50; N, 1.79.

EXAMPLE 80

N-{5-[(4',6'-O-Benzylidene-β-D-maltosyl)-oxy-methyl]-2-chloro-phenyl}-carbamic acid methyl ester Step 1

N-{5-[(2,2',3,3',4',6,6'-Hepta-O-acetyl-β-D-maltosyl)-oxymethyl]-2-chloro-phenyl}-carbamic acid methyl ester To a stirred solution of 2-chloro-5-(hepta-O-acetyl-β-D-maltosyl-oxymethyl)-phenylamine (1.40 g, 1.80 mmol) in THF (18 mL) at 0° C. was added NaH (0.108 g, 2.70 mmol). After 10 min. at this temperature, methyl chloroformate (0.167 mL, 2.16 mmol) was added, and then the reaction was warmed to rt for 3 h. At this point, the reaction was concentrated, and the residue was diluted with EtOAc (300 mL). This solution was washed with 1N HCl (30 mL), sat. aq. NaHCO$_3$ (30mL), and brine (30 mL) and then dried (MgSO$_4$). After concentration, the resulting oily residue was purified by flash chromatography (2:98 to 10:90 acetone:CHCl$_3$ gradient) to afford the product (1.33 g, 88%) as a white foam, mp >79° C. (decomp.); $^1$H NMR (DMSO-d$_6$) δ1.93 (s, 3H), 1.94 (s, 6H), 1.970 (s, 3H), 1.973 (s, 3H), 2.01 (s, 3H), 2.08 (s, 3H), 3.64 (s, 3H), 3.91–4.03 (m, 4H), 4.12–4.23 (m, 2H), 4.38 (dd, J=1.8, 11.9 Hz, 1H), 4.54 (d, J=12.7 Hz, 1H), 4.69–4.75 (m, 2H), 4.83–4.88 (m, 2H), 4.97 (t, J=9.7 Hz, 1H), 5.21 (dd, J=9.7, 10.3 Hz, 1H), 5.27 (d, J=3.7 Hz, 1H), 5.30 (dd, J=8.6, 9.2 Hz, 1H), 7.07 (dd, J=2.0, 8.3 Hz, 1H), 7.44 (d, J=8.1 Hz, 1H), 7.48 (d, J=1.8 Hz, 1H), 9.08 (s, 1H); IR (KBr) 3420, 2950, 1755, 1590, 1530, 1450, 1420, 1375, 1230, 1130, and 1040 cm$^{-1}$; mass spectrum [(+) FAB], m/z 834 (M+H)$^+$, 856 (M+Na)$^+$, Anal. Calcd. for C$_{35}$H$_{44}$ClNO$_{20}$.0.5 H$_2$O: C, 49.86; H, 5.38; N, 1.66, Found: C, 49.68; H, 5.14; N, 1.58.

Step 2

{2-Chloro-5-[(β-D-maltosyl)-oxy-methyl]-phenyl}-carbamic acid methyl ester

The title compound was prepared as a white foam (0.753 g, 99%) from N-{5-[(2,2',3,3',4',6,6'-hepta-O-acetyl-β-D-maltosyl)-oxymethyl]-2-chloro-phenyl}-carbamic acid methyl ester using a procedure similar to step 2 of Example 63, mp >109° C. (decomp.); $^1$H NMR (DMSO-d$_6$) δ3.01–3.11 (m, 2H), 3.19–3.27 (m, 2H), 3.28–3.38 (m, 2H), 3.38–3.50 (m, 3H), 3.52–3.64 (m, 2H), 3.64 (s, 3H), 3.72 (d, J=11.2 Hz, 1H), 4.28 (d, J=7.9 Hz, 1H), 4.44–4.57 (m, 2H), 4.67 (ABq, J=12.5 Hz, Δδ=0.22, 2H), 4.83–4.96 (bs, 2H), 5.01 (d, J=4.0 Hz, 1H), 5.16–5.32 (bs, 1H) 5.34–5.58 (bs, 2H), 7.21 (dd, J=2.0, 8.1 Hz, 1H), 7.43 (d, J=8.1 Hz, 1H), 7.53 (d, J=1.8 Hz, 1H), 9.07 (s, 1H); IR (KBr) 3420, 2920, 1725, 1590, 1530, 1450, 1425, 1370, 1310, 1255, 1230, 1140, 1070, and 1030 cm$^{-1}$; mass spectrum [(+) FAB], m/z 562/564 (M+Na)$^+$, Anal. Calcd. for $C_{21}H_{30}ClNO_{13}$.0.5 $H_2O$: C, 45.95; H, 5.69; N, 2.55, Found: C, 45.81; H, 5.82; N, 2.39.

Step 3

N-{5-[(4',6'-O-Benzylidene-β-D-maltosyl)-oxy-methyl]-2-chloro-phenyl}-carbamic acid methyl ester The title compound was prepared as a white solid (0.552 g, 71%) from {2-chloro-5-[(β-D-maltosyl)-oxy-methyl]-phenyl}-carbamic acid methyl ester using a procedure similar to Example 24, mp 142–145° C.; $^1$H NMR (DMSO-d$_6$) δ3.06–3.13 (m, 1H), 3.28–3.41 (m, 4H), 3.46 (td, J=2.4, 8.8 Hz, 1H), 3.50–3.61 (m, 2H), 3.65 (s, 3H), 3.65–3.75 (m, 3H), 4.11 (dd, J=3.1, 8.1 Hz, 1H), 4.30 (d, J=7.7 Hz, 1H), 4.64–4.69 (m, 1H), 4.68 (ABq, J=12.5 Hz, Δδ=0.22, 2H), 5.14 (d, J=3.7 Hz, 1H), 5.26 (d, J=5.1 Hz, 1H), 5.30 (d, J=4.8 Hz, 1H), 5.51 (d, J=2.9 Hz, 1H), 5.57 (s 1H), 5.63 (d, J=6.4 Hz, 1H), 7.22 (dd, J=2.0, 8.1 Hz, 1H), 7.34–7.38 (m, 3H), 7.41–7.46 (m, 3H), 7.54 (d, J=1.8 Hz, 1H), 9.07 (s, 1H); IR (KBr) 3530, 3410, 2920, 2850, 1730, 1590, 1535, 1450, 1420, 1375, 1310, 1250, 1230, 1145, 1075, 1030, and 1000 cm$^{-1}$; mass spectrum [(+) FAB], m/z 650/652 (M+Na)$^+$; Anal. Calcd. for $C_{28}H_{34}ClNO_{13}$.0.5 $H_2O$: C, 52.79; H, 5.54; N, 2.20, Found: C, 52.85; H, 5.77; N, 2.11.

EXAMPLE 81

N-{5-[(6-O-Benzoyl-4',6'-O-benzylidene-β-D-maltosyl)-oxy-methyl]-2-chloro-phenyl}-carbamic acid methyl ester The title compound was prepared as a white solid (0.407 g, 71%) from N-{5-[(4',6'-O-benzylidene-β-D-maltosyl)-oxy-methyl]-2-chloro-phenyl}-carbamic acid methyl ester using a procedure similar to Example 2, mp >103° C. (decomp.); $^1$H NMR (DMSO-d$_6$) δ3.16–3.22 (m, 1H), 3.27–3.42 (m, 2H), 3.48–3.63 (m, 4H), 3.63 (s,3H), 3.70 (dd, J=5.1, 10.1 Hz, 1H), 3.73–3.79 (m, 1H), 4.05 (dd, J=4.8, 9.9 Hz, 1H), 4.35 (dd, J=5.1, 12.1 Hz, 1H), 4.40 (d, J=7.7 Hz, 1H), 4.58–4.63 (m, 1H), 4.66 (ABq, J=12.5 Hz, Δδ=0.14, 2H), 5.14 (d, J=4.0 Hz, 1H), 5.35 (dd, J=5.3, 8.3 Hz, 2H), 5.52 (s, 1H), 5.57 (d, J=3.1 Hz, 1H), 5.80 (d, J=6.2 Hz, 1H), 7.19 (dd, J=2.0, 8.1 Hz, 1H), 7.33–7.43 (m, 6H), 7.50–7.55 (m, 3H), 7.63–7.68 (m, 1H) 8.00 (dd, J=1.1, 8.1 Hz, 2H), 9.05 (s, 1H); IR (KBr) 3420, 3080, 2920, 2860, 1725, 1640, 1590, 1530, 1445, 1425, 1370, 1320, 1275, 1220, 1140, 1070, 1025, and 720 cm$^{-1}$; mass spectrum [(+) ESI], m/z 732/734 (M+H)$^+$, 754/756 (M+Na)$^+$; Anal. Calcd. for $C_{35}H_{48}ClNO_{14}$: C, 57.42; H, 5.23; N, 1.91, Found: C, 57.17; H, 5.26; N, 1.81.

EXAMPLE 82

N-{5-[(6-O-(3-Benzyl-1-oxo-propyl)-4',6'-O-benzylidene-β-D-maltosyl)-oxy-methyl]-2-chloro-phenyl}-carbamic acid methyl ester The title compound was prepared as a white solid (0.152 g, 42%) from N-{5-[(4',6'-O-benzylidene-β-D-maltosyl)-oxy-methyl]-2-chloro-phenyl}-carbamic acid methyl ester using hydrocinnamoyl chloride and a procedure similar to Example 2, mp >93° C. (decomp.); $^1$H NMR (DMSO-d$_6$) δ2.66 (t, J=7.7 Hz, 2H), 2.84 (t, J=7.7 Hz, 2H), 3.08–3.16 (m, 1H), 3.27–3.49 (m, 4H), 3.53–3.60 (m, 2H), 3.62–3.72 (m, 2H), 3.63 (s, 3H), 4.05–4.13 (m, 2H), 4.31–4.37 (m, 2H), 4.63 (ABq, J=12.5 Hz, Δδ=0.15, 2H), 5.09 (d, J=3.7 Hz, 1H), 5.34 (t, J=5.5 Hz, 2H), 5.55–5.58 (m, 2H), 5.82 (d, J=6.2 Hz, 1H), 7.12–7.18 (m, 1H), 7.18–7.27 (m, 5H), 7.34–7.39 (m, 3H), 7.41–7.46 (m, 3H), 7.54 (d, J=1.8 Hz, 1H), 9.07 (s, 1H); IR (KBr) 3410, 3080, 3030, 2920, 2850, 1735, 1590, 1530, 1450, 1425, 1375, 1310, 1250, 1220, 1145, 1070, 1030, 750, and 700 cm$^{-1}$; mass spectrum [(−) ESI], m/z 758 (M−H)$^-$; Anal. Calcd. for $C_{37}H_{42}ClNO_{14}$.1.0 $H_2O$: C, 57.11; H, 5.70; N, 1.80, Found: C, 57.30; H, 5.52; N, 1.77.

EXAMPLE 83

N-{5-[(4',6'-O-Benzylidene-β-D-maltosyl)-oxy-methyl]-2-chloro-phenyl}-methanesulfonamide Step 1

N-{5-[(2,2',3,3',4',6,6'-Hepta-O-acetyl-β-D-maltosyl)-oxy-methyl]-2-chloro-phenyl}-methanesulfonamide To a stirred solution of NaH (0.0467 g, 1.17 mmol) and $CH_2Cl_2$ (10 mL) at rt was added 2-chloro-5-(hepta-O-acetyl-β-D-maltosyl-oxymethyl)-phenylamine (0.755 mg, 0.973 mmol). After 10 min., MsCl (0.0906 mL, 1.17 mmol) was added to this solution dropwise, and the reaction was stirred at rt for 18 h. Another 2.4 eq. MsCl added and continued stirring at rt for 144 h. Since reaction was only about 25% complete, it was refluxed for 24 h. Then another 2.4 eq. MsCl added and continued refluxing for 120 h. The resulting solution was concentrated and then diluted with EtOAc (200 mL). This layer was washed with 1N HCl (20 mL), sat. $NaHCO_3$ (20 mL), and brine (20 mL) and then dried ($MgSO_4$). After concentration, the oilly residue was purified by flash chromatography (10:90 to 60:40 acetone:hexane gradient) to afford the product (0.423 g, 51%) as a white foam, mp >73° C. (decomp.); $^1$H NMR (DMSO-d$_6$) δ1.93 (d, J=1.8 Hz, 3H), 1.94 (d, J=1.8 Hz, 3H), 1.95 (d, J=1.5 Hz, 3H), 1.97 (d, J=0.9 Hz, 6H), 2.01 (d, J=1.5 Hz, 3H), 2.08 (d, J=1.5 Hz, 3H), 3.02 (d, J=1.3 Hz, 3H), 3.90–4.04 (m, 4H), 4.11–4.23 (m, 2H), 4.38 (d, J=11.6 Hz, 1H), 4.56 (d, J=12.7 Hz, 1H), 4.68–4.77 (m, 2H), 4.82–4.89 (m, 2H), 4.97 (t, J=9.7 Hz, 1H), 5.20 (t, J=9.4 Hz, 1H), 5.27 (d, J=3.1 Hz, 1H), 5.27–5.34 (m, 1H), 7.15 (d, J=8.3 Hz, 1H), 7.35 (s, 1H), 7.50 (dd, J=1.5, 8.3 Hz, 1H), 9.47 (s, 1H); IR (KBr) 3480, 3260, 3010, 2950, 1755, 1590, 1495, 1420, 1375, 1355, 1230, 1140, 1045, 975, 900, and 755 cm$^{-1}$; mass spectrum [(+) FAB], m/z 854 (M+H)$^+$, 876 (M+Na)$^+$, Anal. Calcd. for $C_{34}H_{44}ClNO_{20}S$.1.25 $H_2O$: C, 46.58; H, 5.35; N, 1.60, Found: C, 46.22; H, 4.93; N, 1.49.

Step 2

N-{5-[(β-D-Maltosyl)-oxy-methyl]-2-chloro-phenyl}-methanesulfonamide sodium salt The title compound was prepared as a white solid (0.310 g, 71%) from N-{5-[(2,2',3,3',4',6,6'-hepta-O-acetyl-β-D-maltosyl)-oxy-methyl]-2-chloro-phenyl}-methanesulfonamide using 1.3 eq. 25 weight % NaOMe in MeOH (because of sulfonamide acidity) and a procedure similar to step 4 of Example 1, mp >189° C. (decomp.); $^1$H NMR (DMSO-d$_6$) δ2.54 (s, 3H), 3.05 (t, J=8.1 Hz, 2H), 3.16 (s, 1H), 3.18–3.24 (m, 2H), 3.27–3.42 (m, 2H), 3.42–3.51 (m, 2H), 3.53–3.63 (m, 2H), 3.72 (d, J=11.2 Hz, 1H), 4.24 (d, J=7.7 Hz, 1H), 4.44–4.54 (bs, 1H), 4.50 (ABq, J=11.6 Hz, Δδ=0.24, 2H), 4.54–4.60 (bs, 1H), 4.80–4.93 (bs, 2H), 5.01 (d, J=3.7 Hz, 1H), 5.09–5.18 (bs, 1H), 5.27–5.55 (bs, 2H), 6.47 (dd, J=2.0, 7.9 Hz, 1H), 7.05 (d, J=7.9 Hz, 1H), 7.19 (d, J=2.0 Hz, 1H); IR (KBr) 3410, 2920, 1630, 1590, 1475, 1420, 1375, 1310, 1215, 1140, 1110, 1075, and 1020 cm$^{-1}$; mass spectrum [(+) FAB], m/z 582 (M+Na)$^+$, Anal. Calcd. for $C_{20}H_{29}ClNO_{13}S.Na$ 3.5 $H_2O$: C, 37.24; H, 5.63; N, 2.17, Found: C, 37.00; H, 5.10; N, 2.13.

Step 3

N-{5-[(4',6'-O-Benzylidene-β-D-maltosyl)-oxy-methyl]-2-chloro-phenyl}-methanesulfonamide The title compound was prepared as a white solid (0.198 g, 55%) from N-{5-[(β-D-maltosyl)-oxy-methyl]-2-chloro-phenyl}-methanesulfonamide sodium salt using a procedure similar to Example 24, mp >93° C. (decomp.); $^1$H NMR (DMSO-d$_6$) δ3.05 (s, 3H), 3.07–3.14 (m, 1H), 32.6–3.42 (m, 4H), 3.42–3.48 (m, 1H), 3.50–3.59 (m, 2H), 3.63–3.75 (m, 3H), 4.11 (d, J=5.4 Hz, 1H), 4.30 (d, J=7.7 Hz, 1H), 4.66 (t, J=6.6 Hz, 1H), 4.71 (ABq, J=12.7 Hz, Δδ=0.19, 2), 5.14 (d, J=3.7 Hz, 1H), 5.29 (t, J=4.2 Hz, 2H), 5.51 (d, J=3.1 Hz, 1H), 5.57 (s, 1H), 5.63 (d, J=6.6 Hz, 1H), 7.30 (dd, J=1.8, 8.1 Hz, 1H), 7.34–7.39 (m, 3H), 7.42–7.47 (m, 3H), 7.49 (d, J=8.1 Hz, 1H), 9.44 (s, 1H); IR (KBr) 3410, 2910, 2840, 1630, 1590, 1495, 1445, 1385, 1345, 1235, 1160, 1070, 1025, 990, and 755 cm$^{-1}$; mass spectrum [(−) FAB], m/z 646 (M−H)$^-$; Anal. Calcd. for $C_{27}H_{34}ClNO_{13}S.2.0$ $H_2O$: C, 47.40; H, 5.60; N, 2.05, Found: C, 47.09; H, 4.99; N, 1.98.

EXAMPLE 84

N-{5-[(6-O-Benzoyl-4',6'-O-benzylidene-β-D-maltosyl)-oxy-methyl]-2-cyano-phenyl}-acetamide Step 1

α-Bromo-2-nitro-p-tolunitrile

A stirred mixture containing 4-methyl-2-nitrobenzonitrile (2.04 g, 12.6 mmol), N-bromosuccinimide (2.24 g, 12.6 mmol) and azobisisobutyronitrile (0.103 g, 0.630 mmol) in $CCl_4$ (50 mL) was irradiated with a 300 watt flood light for 2 h. The reaction was diluted with $CH_2Cl_2$ (50 ml), filtered and concentrated. Purification by flash chromatography (35 and 40% ether/pet. ether gradient) gave 1.44 g (47%) of the title compound as a yellow oil. $^1$H NR (DMSO-d6) δ4.90 (s, 2 H), 8.05 (dd, J=8.0, 1.5 Hz, 1 H), 8.18 (d,=8.0, 1 H), 8.52 (s, 1 H).

Step 2

α-Hydroxy-2-nitro-p-tolunitrile

A stirred solution containing α-bromo-2-nitro-p-tolunitrile (1.228 g, 5.095 mmol) and sodium formate (0.8664 g, 12.74 mmol) in ethanol:water (4:1, 25 mL) was refluxed for 2 h. The reaction was cooled to room temperature, diluted with 20% $CH_2Cl_2$/EtOAc, washed with H2O (3×), dried (MgSO$_4$) and concentrated. Purification by flash chromatography (1,2 and 3% MeOH/CHCl$_3$ gradient) gave 0.695 g (77%) of the title compound as a white solid. $^1$H NMR (DMSO-d$_6$) δ4.71 (d, 2 H), 5.75 (t, 1 H), 7.89 (dd, J=7.9 Hz, 1 H), 8.14 (d, J=7.9 Hz, 1 H), 8.32 (s, 1 H).

Step 3

5-[(Hepta-O-acetyl-β-D-maltosyl)-oxy-methyl]-2-cyano-1-nitrobenzene

At ambient temperature, to a stirred solution of acetobromomaltose (2.39 g, 3.41 mmol), α-hydroxy-2-nitro-p-tolunitrile (0.789 g, 4.43 mmol) and $HgBr_2$ (1.60 g, 4.43 mmol) in freshly distilled $CH_3CN$ (34 mL) was added in one portion $Hg(CN)_2$ (1.12 g, 4.43 g, mmol). After 16 h, brine (50 mL) was added and the mixture was extracted with 10% $CH_2Cl_2$/EtOAc. The combined organic extracts were washed with brine (3×), dried (MgSO4) and concentrated. Purification by flash chromatography (1,2 and 3% MeOH/CHCl$_3$ gradient) gave 1.941 g (71%) of the title compound as a foam. An analytical sample was obtained by cyrstallization from EtOAc/Hexane followed by recyrstallization from EtOH to give a colorless solid, mp 155–157° C.; $^1$H NMR (DMSO-d$_6$) δ1.93 (s, 3 H), 1.94 (s, 3 H), 1.97 (s, 3 H), 1.99 (s, 3 H), 2.01 (s, 3 H), 2.06 (s, 3 H), 3.93–4.01 (m, 4 H), 4.36 (d, J=11.0 Hz, 1 H), 4.77 (dd, J=9.6, 8.0 Hz, 1 H), 4.83–4.88 (m, 2 H), 4.93–5.00 (m, 3 H), 5.21 (dd, J=10.3, 9.7 Hz, 1 H), 5.27 (d, J=3.7 Hz, 1 H), 5.30–5.34 (m, 1 H), 7.84 (dd, J=7.9, 1.5 Hz, 1 H), 8.18 (d, J=7.9 Hz, 1 H), 8.27 (s, 1 H). IR (KBr) 3450, 2950, 2225, 1750, 1225 and 1050 cm$^{-1}$. mass spectrum [(+) FAB] m/z 797 (M+H)$^+$. Anal. Calcd. for $C_{34}H_{40}N_2O_{20}$: C, 51.26; H, 5.06; N, 3.52. Found: C, 51.06; H, 5.02; N, 3.31.

Step 4

5-[(Hepta-O-acetyl-β-maltosyl)-oxy-methyl]-2-cyano-phenylamine

A stirred mixture containing 5-[(hepta-O-acetyl-β-D-maltosyl)-oxy-methyl]-2-cyano-1-nitrobenzene (1.491 g, 1.872 mmol) iron powder (0.3658 g, 6.550 mmol) and glacial acetic acid (7 mL) in 2-propanol (7 mL) was heated at 75° C. for 2 h. To the reaction was added activated charcoal and the hot solution was filtered through a sulka ploc pad, rinsing with EtOAc. The filtrate was washed with $H_2O$ (3×), with sat. aq. NaHCO$_3$ (3×), dried (Na$_2$SO$_4$) and concentrated. Purification by flash chromatography (1,2 and 3% MeOH/CHCl$_3$ gradient) gave 1.04 g (72%) of the title compound. $^1$H NMR (DMSO-d$_6$) δ1.94 (s, 3 H), 1.95 (s, 3 H), 1.96 (s, 3 H), 1.98 (s, 6 H), 2.02 (s, 3 H), 2.09 (s, 3 H), 3.95–4.02 (m, 4 H), 4.14–4.22 (m, 2 H), 4.36–4.40 (m, 1 H), 4.56 (ABq, J=13.2 Hz, Δδ=0.09, 2 H), 4.72 (dd, J=9.4, 8.2 Hz, 1 H), 4.98 (t, J=9.7 Hz, 1 H), 5.19–5.37 (m, 3 H), 6.06 (s, 1H), 6.49 (dd, J=8.1, 1.0 Hz, 1 H), 6.66 (s, 1 H), 7.36 (d, J=8.1 Hz, 1 H). mass spectrum [(+)FAB], m/z 767 (M+H)$^+$.

Step 5

N-{5-[(Hepta-O-acetyl-β-D-maltosyl)-oxy-methyl]-2-cyano-phenyl}-acetamide

At ambient temperature, to a solution of 5-[(hepta-O-acetyl-β-maltosyl)-oxy-methyl]-2-cyano-phenylamine (0.280 g, 0.365 mmol) in $CH_2Cl_2$ (3.6 mL) was added 60% NaH/mineral oil (14.6 mg, 0.365 mmol) and the reaction was stirred for 0.5 h. To the reaction was added acetyl chloride (31.3 μL, 0.438 mmol) and the reaction was stirred for 16 h. The reaction was quenched with sat. aq. NaHCO$_3$ (25 mL) and extracted with EtOAc. The combined organic extracts were dried (Na$_2$SO$_4$) and concentrated. Purification by flash chromatography (1,2 and 3% MeOH/CHCl$_3$ gradient) gave 0.249 g (84%) of the title compound. An analytical sample was obtained by cyrstallization from EtOAc/Hexane to give a colorless solid, mp 85–95 ° C.; $^1$H NMR (DMSO-d6) δ1.93 (s, 3 H), 1.94 (s, 3 H), 1.95 (s, 3 H), 1.97 (s, 6 H), 2.01 (s, 3 H), 2.07 (s, 3 H), 2.08 (s, 3 H), 3.92–4.01 (m, 4 H), 4.13–4.21 (m, 2 H), 4.37 (dd, J=12.0, 2.1 Hz, 1 H), 4.73 (ABq, J=13.8 Hz, Δδ=0.07, 2 H), 4.73 (dd, J=9.5, 8.0 Hz, 1 H), 4.84–4.89 (m, 2 H), 4.97 (t, J=9.8 Hz, 1 H), 5.21 (dd, J=10.3, 9.7 Hz, 1 H), 5.27–5.33 (m, 2 H), 7.21 (dd, J=8.0, 1.4 Hz, 1 H), 7.48 (s, 1 H), 7.78 (d, J=8.0 Hz, 1 H), 10.15 (s, 1 H). IR (KBr) 3400, 2950, 2225, 1750, 1240 and 1050 cm$^{-1}$. mass spectrum [(+) ESI], m/z 809

(M+H)⁺. Anal. Calcd. for $C_{36}H_{44}N_2O_{19}$: C, 53.47; H, 5.84; N, 3.46. Found: C, 53.55; H, 5.41; N, 3.40.

Step 6

N-{5-[(β-D-Maltosyl)-oxy-methyl]-2-cyano-phenyl}-acetamide

At ambient temperature, to a stirred solution of N-{2-cyano-[5-(2,2',3,3',4',6,6'-hepta-O-acetyl-β-D-maltosyl)-oxy-methyl]-phenyl}-acetamide (2.31 g, 2.86 mmol) in MeOH (70 mL) was added in one portion potassium cyanide (92.9 mg, 1.43 mmol). After 3 h, the reactions was concentrated in vacuo. Purification by preparative HPLC (C18, 20% $CH_3CN:H_2O$) and gave 1.18 g (80%) of the title compound; ¹H NMR (DMSO-d₆) δ2.08 (s, 3H), 3.03–3.17 (m, 2H), 3.20–3.49 (m, 7H), 3.50–3.64 (m, 2H), 3.71–3.75 (m, 1H), 4.31 (d, J=7.6 Hz, 1H), 4.51–4.55 (m, 2H), 4.64–4.78 (m, 3H), 4.88–5.00 (m, 2H), 5.02 (d, J=3.7 Hz, 1H), 5.29–5.53 (m, 3H), 7.38 (dd, J=8.1, 1.1 Hz, 1H), 7.56 (s, 1H), 7.77 (d, J=8.1 Hz, 1H), 7.80 (s, 1H).

Step 7

N-{5-[(4',6'-O-Benzylidene-β-D-maltosyl)-oxy-methyl]-2-cyano-phenyl}-acetamide The title compound was prepared as a solid (0.682 g, 57%) from N-(5-[(β-D-maltosyl)-oxy-methyl]-2-cyano-phenyl}-acetamide using a procedure similar to Example 24; ¹H NMR (DMSO-d₆) δ2.09 (s, 3H), 3.13–3.16 (m, 2H), 3.35–3.73 (m, 9H), 4.12–4.13 (m, 1H), 4.34 (d, J=7.8 Hz, 1H), 4.65–4.70 (m, 2H), 4.91 (d, J=13.6 Hz, 1H), 5.15 (d, J=3.8 Hz, 1H), 5.32 (m, 2H), 5.55–5.58 (m, 3H), 7.36–7.47 (m, 6H), 7.56 (s, 1H), 7.78 (d, J=8.2 Hz, 1H), 10.17 (s, 1H).

Step 8

N-{5-[(6-O-Benzoyl-4',6'-O-benzylidene-β-D-maltosyl)-oxy-methyl]-2-cyano-phenyl}-acetamide The title compound was prepared as a white solid (0.173 g, 49%) from N-{5-[(4',6'-O-benzylidene-β-D-maltosyl)-oxy-methyl]-2-cyano-phenyl}-acetamide using a procedure similar to Example 2, mp 122–129° C.; ¹H NMR (DMSO-d₆) δ2.05 (s, 3H), 3.21 (t, 1H), 3.34–3.41 (m, 2H), 3.53–3.64 (m, 4H), 3.71–3.77 (m, 2H), 4.03 (dd, 1H), 4.34 (dd, J=12.2, 4.9 Hz, 1H), 4.42 (d, J=7.7 Hz, 1H), 4.59 (d, 1H), 4.75 (ABq, J=13.7 Hz, Δδ=0.06, 2H), 5.14 (d, J=4.0 Hz, 1H), 5.35 (br. s, 1H), 5.41 br. s, 1H), 5.52 (s, 1H), 5.58 (br. s, 1H), 5.82 (br. s, 1H), 7.34–7.37 (m, 4H), 7.40–7.42 (m, 2H), 7.51–7.54 (m, 3H), 7.65 (t, 1H), 7.73 (d, J=7.9 Hz, 1H), 7.97–8.00 (m, 2H), 10.13 (s, 1H); IR (KBr) 3400, 2900, 2200, 1710, 1275 and 1065 cm⁻¹; mass spectrum [(+) ESI], m/z 724 (M+NH₄)⁺; Anal. Calcd. for $C_{36}H_{38}N_2O_{13}$·0.5 $H_2O$: C, 60.42; H, 5.49 N, 3.91, Found: C, 60.36; H, 5.22; N, 3.91.

EXAMPLE 85

N-{5-[(6-O-Benzoyl-4',6'-O-benzylidene-β-D-maltosyl)-oxy-methyl]-2-methyl-phenyl}-acetamide The title compound was prepared as a colorless solid (1.30 g, 60%) from N-{-5-[(4',6'-O-benzylidene-β-D-maltosyl)-oxy-methyl]-2-methyl-phenyl}-acetamide using a procedure similar to Example 2, mp 193–198° C.; ¹H NMR (DMSO-d₆) δ2.00 (s, 3H), 2.15 (s, 3H), 3.17 (t, J=8.4 Hz, 1H), 3.34–3.40 (m, 2H), 3.48–3.62 (m, 4H), 3.69–3.77 (m, 2H), 4.06 (dd, 1H), 4.33–4.38 (m, 2H), 4.60 (ABq, J=11.9 Hz, Δδ=0.08, 2H), 4.61 (d, J=10.5 Hz, 1H), 5.14 (d, J=4.0 Hz, 1H), 5.33 (br. s, 2H), 5.52 (s, 1H), 5.56 (br. s, 1H), 5.79 (br. s, 1H), 7.06 (dd, 1H), 7.11 (d, J=7.9 Hz, 1H), 7.34–7.37 (m, 4H), 7.40–7.43 (m, 2H), 7.51–7.55 (m, 2H), 7.63–7.68 (m, 1H), 7.99–8.01 (m, 2H), 9.26 (s, 1H); IR (KBr) 3250, 2900, 1725, 1650, 1275 and 1070 cm⁻¹; mass spectrum [(+) ESI], m/z 696 (M+H)⁺; Anal. Calcd. for $C_{36}H_{41}NO_{13}$: C, 62.15; H, 5.94; N, 2.01, Found: C, 62.20; H, 6.02; N, 2.04.

EXAMPLE 86

6-[-6-(4-Chloro-3-nitro-benzylsulfanyl)-4,5-dihydroxy-2-hydroxymethyl-tetrahydro-pyran-3-yloxy]-2-phenyl-hexahydro-pyrano[3,2-d][1.3]dioxine-7,8-diol Step 1

(4-Chloro-3-nitro-benzyl)-hepta-O-acetyl-1-thio-β-D-maltoside

To a stirred solution of hepta-O-acetyl-1-thio-β-maltose (2.0 g, 3.065 mmol) in acetone (20 ml) were added 4-chloro-3-nitrobenzyl bromide (0.844 mg, 3.37 mmol) and a solution of potassium carbonate (0.423 mg, 3.065 mmol) in water (10 ml). The mixture was boiled under reflux for 30 min, cooled and concentrated. The residue was extracted with dichloromethane, and the combined extracts were washed with water, and brine, dried (MgSO₄) and concentrated. Purification by flash chromatography (40%–60% EtOAc/petroleum ether gradient) afforded 1.588 g (63%) of the title compound as a white solid, mp 73–75° C.; ¹H NMR (CDCl₃) δ1.99 (s, 3 H), 2.00 (s, 3 H), 2.02 (s, 3 H), 2.03 (s, 6 H), 2.11 (s, 3 H), 2.15 (s, 3 H), 3.61–3.64 (m, 1 H), 3.80 (d, J=13.6 Hz, 1H), 3.94–4.00 (m, 3 H), 4.08 (dd, J=12.3, 2.4 Hz, 1H), 4.18–4.27 (m, 2 H), 4.36 (d, J=9.9 Hz, 1H), 4.50 (dd, J=12.1, 2.6 Hz, 1 H), 4.85 (dd, J=10.5, 4.0 Hz, 1 H), 4.90 (apparant t, J=9.9 Hz, 1 H), 5.05 (apparant t, J=9.9 Hz, 1 H), 5.23 (apparant t, J=9.2 Hz, 1 H), 5.34 (apparant t, J=9.7 Hz, 1 H), 5.40 (d, J=4.0 Hz, 1 H), 7.47 (dd, J=8.4, 2.0 Hz, 1 H), 7.51 (d, J=8.4 Hz, 1H), 7.87 (d, J=2.0, Hz, 1 H). IR (KBr) 3500, 2950, 1750, 1250 and 1050 cm⁻¹, mass spectrum [(+) FAB], m/z 822 (M+H)⁺, 844 (M+Na)⁺. Anal. Calcd. for $C_{33}H_{40}ClNO_{19}S$: C, 48.21; H, 4.90; N, 1.70. Found: C, 47.75; H, 4.86; N, 1.65.

Step 2

(4-Chloro-3-nitro-benzyl)-1-deoxy-1-thio-β-D-maltoside

The title compound was prepared as a white solid (0.513 g, 99%) from (4-chloro-3-nitro-benzyl)-hepta-O-acetyl-1-thio-β-D-maltoside using a procedure similar to step 4 of Example 1, mp 90–93° C.; ¹H NMR (DMSO-d₆) δ3.03–3.74 (m, 11 H), 3.80 (d, J=6.2 Hz, 1 H), 3.86 (d, J=13.4 Hz, 1 H), 4.01–4.08 (m, 2 H), 4.58 (bd, 2 H), 4.98 (bd, 3 H), 5.20–5.67 (bs, 3 H), 7.65–7.72 (m, 2 H), 8.03 (d, J=1.76 Hz, 1 H).IR (KBr) 3400, 2930, 1550, 1300 and 1075 cm⁻¹, mass spectrum [(−) FAB], m/z 526 (M−H)⁻.Anal. Calcd. for $C_{19}H_{26}ClNO_{12}S·H_2O$: C, 41.80; H, 5.13; N, 2.56. Found: C, 41.35; H, 4.89; N, 2.40.

Step 3

6-[-6-(4-Chloro-3-nitro-benzylsulfanyl)-4,5-dihydroxy-2-hydroxymethyl-tetrahydro-pyran-3-yloxy]-2-phenyl-hexahydro-pyrano[3,2-d][1,3]dioxine-7,8-diol The title compound was prepared as a white solid from (4-chloro-3-nitro-benzyl)-1-deoxy-1-thio-β-D-maltoside using a procedure similar to Example 24, mp 120–122° C.; ¹H NMR (DMSO-d₆) β3.07–3.24 (m, 2H), 3.24–3.43 (m, 3H), 3.47–3.58 (m, 3H), 3.64–3.75 (m, 3H), 3.95 (ABq, J=13.4 Hz, Δδ=0.12, 2H), 4.08–4.13 (m, 2H), 4.77 (t, J=5.5

Hz, 1H), 5.12 (d, J=3.95 Hz, 1 H), 5.28 (d, J=5.3, Hz, 1H), 5.31 (d, J=5.3, Hz, 1H), 5.56 (m, 2H), 5.65 (d, J=6.4, Hz, 1H), 7.35–7.40 (m, 3H), 7.42–7.46 (m, 2H), 7.66–7.71 (m, 2H), 8.04 (d, J=1.76 Hz, 1H); IR (KBr) 3450, 2930, 1550, 1300 and 1075 cm$^{-1}$; mass spectrum [(−) FAB], m/z 614 (M−H)$^{-}$; Anal. Calcd. for $C_{26}H_{30}ClNO_{12}S$: C, 49.96; H, 5.1; N,2.24, Found: C, 49.42; H, 4.78; N, 2.26.

EXAMPLE 87

(4-Chloro-3-nitro-benzyl) 6-O-benzoyl-4',6'-O-benzoyl-4',6'-O-benzylidene-1-thio-β-D-maltoside The title compound was prepared as a white solid from 6-[-6-(4-chloro-3-nitro-benzylsulfanyl)-4,5-dihydroxy-2-hydroxymethyl-tetrahydro-pyran-3-yloxy]-2-phenyl-hexahydro-pyrano[3,2-d][1,3]dioxine-7,8-diol using a procedure similar to Example 2, mp 105–107° C.; $^1$H NMR (DMSO) δ3.17–3.23 (m, 1H), 3.27–3.42 (m, 2H), 3.46–3.51 (m, 1H), 3.53–3.62 (m, 3H), 3.69–3.76 (m, 2H), 3.91 (q, J=14.1 Hz), 2H), 4.06 (dd, J=10.3, 4.8 Hz, 1H), 4.28–4.34 (m, 2H), 4.62 (d, J=10.5 Hz, 1H), 5.13 (d, J=3.7 Hz, 1H), 5.34 (d, J=5.3 Hz, 1H), 5.41 (d, J=6.2 Hz, 1H), 5.53 (s, 1H), 5.64 (d, J=2.9 Hz, 1H), 5.80 (d, J=6.1 Hz, 1H), 7.31 (m, 3H), 7.40–7.43 (m, 2H), 7.47 (t, J=5.7 Hz, 2H), 7.59–7.65 (m, 3H), 7.95–7.98 (m, 3H), IR (KBr) 3400, 2930, 1745, 1550, 1255 and 1075 cm$^{-1}$; mass spectrum [(+) FAB], m/z 720 (M+H)$^+$, 742 (M+Na)$^+$; Anal. Calcd. for $C_{33}H_{34}ClNO_{13}S$: C, 55.04; H, 4.76; N, 1.95, Found: C, 55.36; H, 4.89; N, 1.91.

What is claimed is:

1. A compound of formula I having the structure

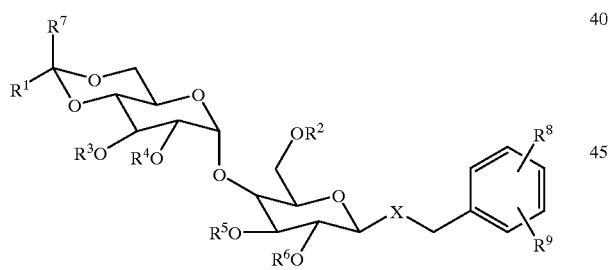

I wherein

X is O or S;

$R^1$ alkyl of 1–6 carbons atoms, haloalkyl of 1–6 carbon atoms, nitroalkyl of 1–6 carbon atoms, cyanoalkyl of 1–6 carbon atoms, alkoxyalkyl of 2–12 carbon atoms, phenyl mono-, di-, or tri-substituted with $R^8$, phenylalkyl of 7–10 carbon atoms, wherein the phenyl ring mono-, di-, or tri-substituted with $R^8$, pyridyl substituted with $R^8$, furyl substituted with $R^8$, thienyl substituted with $R^8$, and thiazolyl substituted with $R^8$;

$R^2$ is hydrogen, acyl of 2–6 carbon atoms, haloacyl of 2–6 carbon atoms, nitroacyl of 2–7 carbon atoms, cyanoacyl of 2–7 carbon atoms, or trifluoromethylacyl of 3–8 carbon atoms, carboalkoxyacyl of 4–12 carbon atoms,

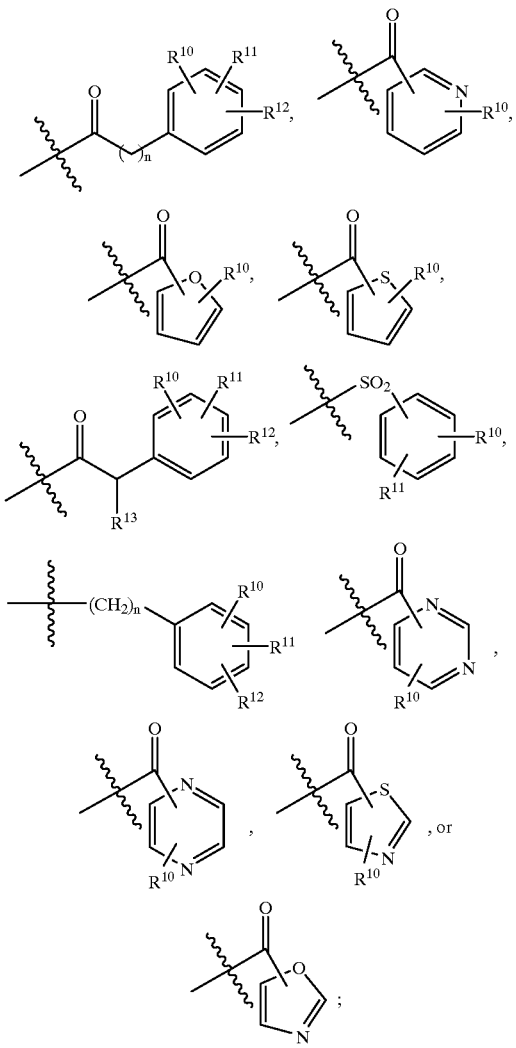

$R^3$, $R^4$, $R^5$, $R^6$ are each, independently, hydrogen, acyl of 2–7 carbon atoms, benzoyl, wherein the phenyl moiety is mono-, di-, or tri-substituted with $R^8$, haloacyl of 2–7 carbon atoms, nitroacyl of 2–7 carbon atoms, cyanoacyl of 2–7 carbon atoms, or trifluoromethylacyl of 3–8 carbon atoms;

$R^7$ is hydrogen;

$R^8$ is hydrogen, alkyl of 1–6 carbon atoms, alkoxy of 1–6 carbon atoms, phenyl, —CN, —NO$_2$, halogen, or —CF$_3$;

$R^9$ is hydrogen, alkyl of 1–6 carbon atoms, alkoxy of 1–6 carbon atoms, phenyl, —CN, —NO$_2$, halogen, —CF$_3$, —NHR$^3$, —NR$^3$R$^3$, —NR$^3$R$^{14}$, —NHCO$_2$R$^{14}$, —NHSO$_2$R$^{14}$,

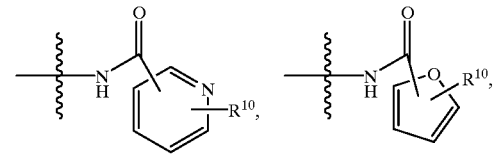

-continued

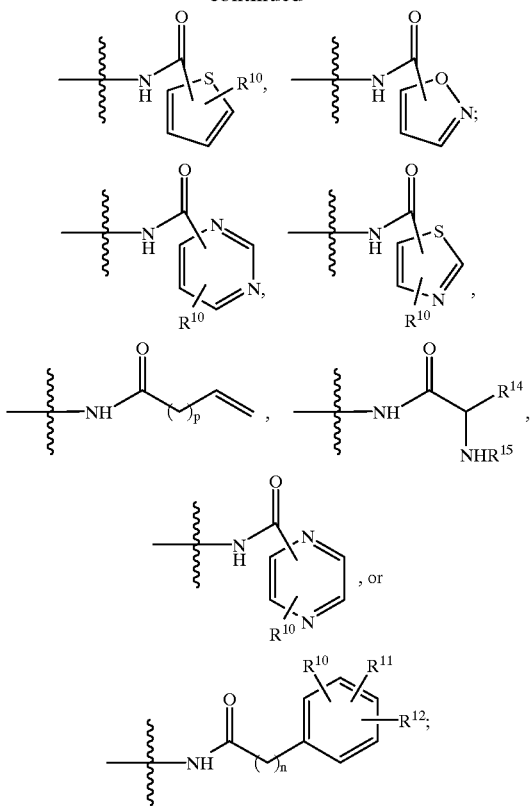

$R^{10}$, $R^{11}$, $R^{12}$, are each, independently, hydrogen, alkyl of 1–6 carbon atoms, alkoxy of 1–6 carbon atoms, phenyl, —CN, —NO$_2$, halogen, —CF$_3$, acyl of 2–7 carbon atoms, or benzoyl, wherein the phenyl group or the phenyl moiety of the benzoyl group is optionally mono-, di-, or tri-substituted with alkyl of 1–6 carbon atoms, alkoxy of 1–6 carbon atoms, —CN, —NO$_2$, halogen, or —CF$_3$;

$R^{13}$ is hydrogen, alkyl of 1–6 carbon atoms, alkoxy of 1–6 carbon atoms, —CN, —NO$_2$, halogen, —CF$_3$, or phenyl group, wherein the phenyl moiety is optionally mono-, di-, tri-substituted with alkyl 1–6 carbon atoms, alkoxy of 1–6 carbon atoms, or halogen;

$R^{14}$ is alkyl of 1–6 carbon atoms;

$R^{15}$ is hydrogen, acyl of 2–7 carbon atoms, benzoyl, or —CO$_2$R$^{16}$;

$R^{16}$ is alkyl of 1–6 carbon atoms, benzyl, phenyl, or fluorenyl;

n=0–3;

p=0–6;

or a pharmaceutically acceptable salt thereof.

2. The compound according to claim 1, wherein $R^2$ is hydrogen, acyl of 2–6 carbon atoms, carboalkoxyacyl of 4–12 carbon atoms,

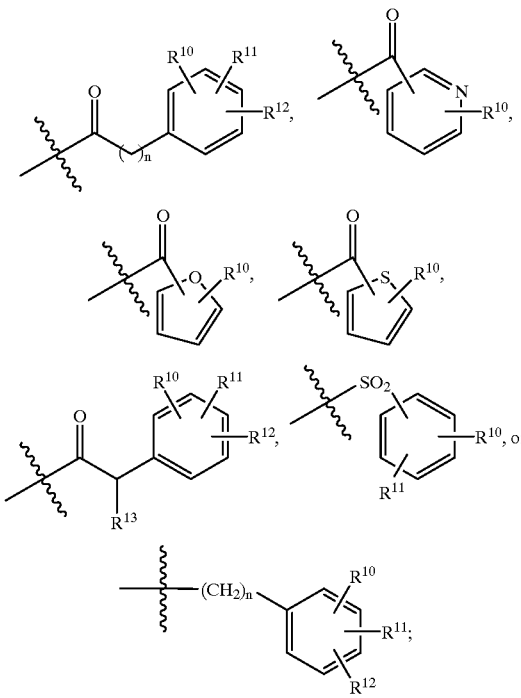

$R^3$, $R^4$, $R^5$, and $R^6$ are each, independently, hydrogen, or acyl of 2–7 carbon atoms;

$R^9$ is hydrogen, —NO$_2$, halogen, —CF$_3$, —NHR$^3$, —NR$^3$R$^3$, —NR$^3$R$^{14}$, —NHCO$_2$R$^{14}$, —NHSO$_2$R$^{14}$,

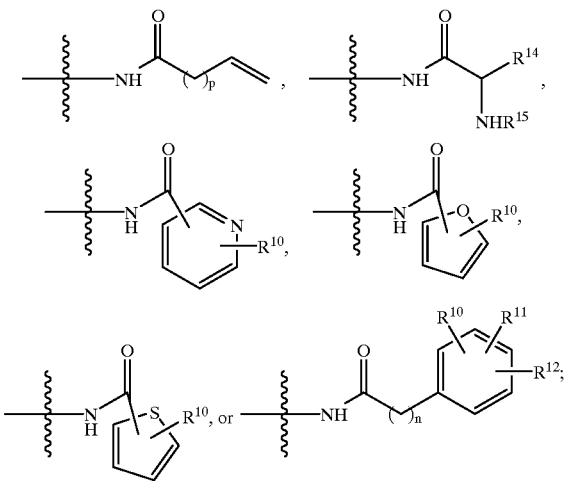

or a pharmaceutically acceptable salt thereof.

3. The compound according to claim 2, wherein

X is O;

$R^1$ is alkyl of 1–6 carbon atoms, haloalkyl of 1–6 carbon atoms, nitroalkyl of 1–6 carbon atoms, cyanoalkyl of 1–6 carbon atoms, alkoxyalkyl of 2–12 carbon atoms, phenyl mono-, di-, or tri-substituted with R$^8$, phenylalkyl of 7–10 carbon atoms, wherein the phenyl ring is mono-, di-, or tri-substituted with R$^8$, or pyridyl substituted with R$^8$;

$R^2$ is hydrogen, acyl of 2–6 carbon atoms, carboalkoxyacyl of 4–12 carbon atoms, $R^3$, $R^4$, $R^5$, and $R^6$ are each, independently, hydrogen, or acyl of 2–7 carbon atoms;

$R^7$ is hydrogen;

$R^8$ is hydrogen, alkyl of 1–6 carbon atoms, —CN, or halogen;

$R^{13}$ is hydrogen, alkyl of 1–6 carbon atoms, halogen, or phenyl group, wherein the phenyl moiety is optionally mono-, di-, or tri-substituted with alkyl of 1–6 carbon atoms, alkoxy of 1–6 carbon atoms, or halogen;

$R^{16}$ is alkyl of 1–6 carbon atoms, or fluorenyl;

or a pharmaceutically acceptable salt thereof.

4. The compound of claim 1, which is N-{5-[(6-O-Benzoyl-4',6'-O-propylidene-β-D-maltosyl)-oxy-methyl]-2-chloro-phenyl}-acetamide or a pharmaceutically acceptable salt thereof.

5. The compound of claim 1, which is N-{5-[(6-O-Benzyl-4',6'-O-benzylidene-β-D-maltosyl)-oxy-methyl]-2-chloro-phenyl}-acetamide or a pharmaceutically acceptable salt thereof.

6. The compound of claim 1, which is N-(5-{[6-O-Benzoyl-4',6'-O-(4-nitro)-benzylidene-β-D-maltosyl]-oxy-methyl}-2-chloro-phenyl)-acetamide or a pharmaceutically acceptable salt thereof.

7. The compound of claim 1, which is N-{5-[(6-O-Benzoyl-4',6'-O-isobutylidene-β-D-maltosyl)-oxy-methyl]-2-chloro-phenyl}-acetamide or a pharmaceutically acceptable salt thereof.

8. The compound of claim 1, which is N-{5-[(6-O-Benzoyl-4',6'-O-((1R)-2-phenyl-ethylidene)-β-D-maltosyloxy)-methyl]-2-chloro-phenyl}-acetamide or a pharmaceutically acceptable salt thereof.

9. The compound of claim 1, which is N-{5-{[6-O-Benzoyl-4',6'-O-((1R)-3-cyanopropylidene)-β-D-maltosyloxy]-methyl}-2-chloro-phenyl}-acetamide or a pharmaceutically acceptable salt thereof.

10. The compound of claim 1, which is Benzoic acid 6-(3-acetylamino-4-chloro-benzoyloxy)-3-(7,8-dihydroxy-2-pyridin-4-yl-hexahydro-pyrano[3,2-d][1,3]dioxin-6-yloxy)-4,5-dihydroxy-tetrahydro-pyran-2-ylmethyl ester or a pharmaceutically acceptable salt thereof.

11. The compound of claim 1, which is N-{5-[(6-O-Benzoyl-4',6'-O-benzylidene-β-D-maltosyl-oxy)-methyl]-2-chloro-phenyl}-acetamide or a pharmaceutically acceptable salt thereof.

12. The compound of claim 1, which is (R)-N-[2-Chloro-5-[[[6-O-(3-trifluoromethylbenzoyl)-4-O-[4,6O-(phenylmethylene)-α-D-glucopyranosyl]-β-D-glucopyranosyl]oxy]-methyl]-phenyl]acetamide or a pharmaceutically acceptable salt thereof.

13. The compound of claim 1, which is N-{5-[(4',6'-O-Benzylidene-6-O-(2-iodo)-benzoyl-β-D-maltosyl)-oxy-methyl]-2-chloro-phenyl)-acetamide or a pharmaceutically acceptable salt thereof.

14. The compound of claim 1, which is (R)-N-[-2-Chloro-5-[[[6-O-(phenylacetyl)-4-O-[4,6-O-(phenylmethylene)-α-D-glucopyranosyl]-β-D-glucopyranosyl]oxy]methyl]phenyl]acetamide or a pharmaceutically acceptable salt thereof.

15. The compound of claim 1, which is N-{5-[(4',6'-O-Benzylidene-6-O-phenyl-ethyl-carboxyl-β-D-maltosyl)-oxy-methyl]-2-chloro-phenyl}-acetamide or a pharmaceutically acceptable salt thereof.

16. The compound of claim 1, which is 4-Benzoyl-N-{5-[(4',6'-O-benzylidene-6-O-(2-iodo)-benzoyl-β-D-maltosyl)-oxy-methyl]-2-chloro-phenyl}-benzamide or a pharmaceutically acceptable salt thereof.

17. The compound of claim 1, which is N-{5-[(6-O-Benzoyl-4',6'-O-benzylidene-β-D-maltosyl)-oxy-methyl]-2-chloro-phenyl}-carbamic acid methyl ester or a pharmaceutically acceptable salt thereof.

18. The compound of claim 1, which is (4-Chloro-3-nitrobenzyl) 6-O-benzoyl-4',6'-O-benzoyl-4',6'-O-benzylidene-1-thio-β-D-maltoside or a pharmaceutically acceptable salt thereof.

19. The compound of claim 1, which is:

a) N-{2-Chloro-5-[(4',6'-O-ethylidene)-β-D-maltosyloxymethyl]-phenyl}-acetamide or a pharmaceutically acceptable salt thereof;

b) (R)-N-[5-[[[6-O-Benzoyl-4-O-(4,6-O-ethylidene-α-D-glucopyranosyl)-β-D-glucopyranosyl]oxy]methyl]-2-chlorophenyl]acetamide or a pharmaceutically acceptable salt thereof;

c) (R)-N-[2-Chloro-5-[[[2,3-di-O-acetyl-6-O-benzoyl-4-O-(2,3-di-O-acetyl-4,6-O-ethylidene-α-D-glucopyranosyl)-β-D-glucopyranosyl]oxy]methyl]phenyl]acetamide or a pharmaceutically acceptable salt thereof;

d) N-{2-Chloro-5-[(4',6'-O-propylidene-β-D-maltosyl)-oxy-methyl]-phenyl}-acetamide or a pharmaceutically acceptable salt thereof;

e) N-(5-{[4',6'-O-Benzylidene-6-O-(4-toluenesulfonyl)-β-D-maltosyl]-oxy-methyl}-2-chloro-phenyl)-acetamide or a pharmaceutically acceptable salt thereof;

f) N-(5-{[2,3,2',3'-Tetra-O-acetyl-4',6'-O-benzylidene-6-O-(4-toluenesulfonyl)-β-D-maltosyl]-oxy-methyl}-2-chloro-phenyl)-acetamide or a pharmaceutically acceptable salt thereof;

g) N-{5-[(6-O-Benzyl-4',6'-O-ethylidene-β-D-maltosyl)-oxy-methyl]-2-chloro-phenyl}-acetamide or a pharmaceutically acceptable salt thereof;

h) N-(2-Chloro-5-{[4',6'-O-(4-nitro)-benzylidene-β-D-maltosyl]-oxy-methyl}-phenyl)-acetamide or a pharmaceutically acceptable salt thereof;

i) N-{2-Chloro-5-[(4',6'-O-(4-chloro)-benzylidene-β-D-maltosyl)-oxy-methyl]-phenyl}-acetamide or a pharmaceutically acceptable salt thereof;

j) N-{5-[(6-O-Benzoyl-4',6'-O-(4-chloro)-benzylidene-β-D-maltosyl)-oxy-methyl]-2-chloro-phenyl}-acetamide or a pharmaceutically acceptable salt thereof;
k) N-{2-Chloro-5-[(4',6'-O-isobutylidene-β-D-maltosyl)-oxy-methyl]-phenyl}-acetamide or a pharmaceutically acceptable salt thereof;
l) N-{5-[(4',6'-O-((1R)-2-Phenyl-ethylidene)-β-D-maltosyloxy)-methyl]-2-chloro-phenyl}-acetamide or a pharmaceutically acceptable salt thereof;
m) N-{2-Chloro-5-[(4',6'-O-((1R)-3-cyano-propylidene)-β-D-maltosyloxy)-methyl]-phenyl}-acetamide or a pharmaceutically acceptable salt thereof;
n) N-{2-Chloro-5-[(4',6'-O-((1R)-3-ethoxy-propylidene)-β-D-maltosyloxy)-methyl]-phenyl}-acetamide or a pharmaceutically acceptable salt thereof;
o) N-{5-{[6-O-Benzoyl-4',6'-O-((1R)-3-ethoxypropylidene)-β-D-maltosyloxy]-methyl}-2-chloro-phenyl}-acetamide or a pharmaceutically acceptable salt thereof;
p) N-(2-Chloro-5-{[4',6'-O-(4-pyridinemethylidene)-β-D-maltosyl]-oxy-methyl}-phenyl)-acetamide or a pharmaceutically acceptable salt thereof;
q) N-{5-[(4',6'-O-Benzylidene-β-D-maltosyloxy)-methyl]-2-chloro-phenyl}-acetamide or a pharmaceutically acceptable salt thereof;
r) N-{5-[(4',6'-O-Benzylidene-2,2',3,3',6-penta-O-acetyl-β-D-maltosyl-oxy)-methyl]-2-chloro-phenyl}-acetamide or a pharmaceutically acceptable salt thereof;
s) (R)-N-[2-Chloro-5-[[[2,3-di-O-acetyl-6-O-benzoyl-4-O-[2,3-di-O-acetyl-4,6-O-(phenylmethylene)-α-D-glucopyranoysl]-β-glucopyranosyl]-oxy]methyl]-phenyl] acetamide or a pharmaceutically acceptable salt thereof;
t) (R)-N-[2-Chloro-5-[[[6-O-(5-methoxy-1,5-dioxopentyl)-4-O-[4,6-O-(phenylmethylene)-α-D-glucopyranoysl]-β-D-glucopyranosyl]oxy]methyl]-phenyl]acetamide or a pharmaceutically acceptable salt thereof;
u) 4-Chloro-3-nitro-benzyl-4',6'-O-benyzlidene-β-D-maltoside or a pharmaceutically acceptable salt thereof;
v) 4-Chloro-3-nitro-benzyl-6-O-benzoyl-4',6'-O-benyzlidene-β-D-maltoside or a pharmaceutically acceptable salt thereof;
w) (R)-(4-Chloro-3-nitrophenyl)methyl-2,3-di-O-acetyl-6-O-benzoyl-4-O-[2,3-di-O-acetyl-4,6-O-(phenylmethylene)-α-D-glucopyranosyl]-β-D-glucopyranoside or a pharmaceutically acceptable salt thereof;
x) Nicotinic acid 6-(4-chloro-3-nitro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester or a pharmaceutically acceptable salt thereof;
y) (R)-(4-Chloro-3-nitrophenyl)methyl 4-[2,3-di-O-acetyl-4,-O-(phenylmethylene)-α-D-glucopyranosyl]-β-D-glucopyranoside 2,3-diacetate 6-(3-pyridinecarboxylate) or a pharmaceutically acceptable salt thereof;
z) 4-Methoxy-benzoic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester or a pharmaceutically acceptable salt thereof;
aa) 4-Methoxy-benzoic acid 4,5-diacetoxy-6-(3-acetylamino-4-chloro-benzyloxy)-3-(7,8-diacetoxy-2-phenyl-hexahydro-pyrano[3,2-d][1,3]dioxin-6-yloxy)-tetrahydro-pyran-2-ylmethyl ester or a pharmaceutically acceptable salt thereof;
bb) 4-Chloro-benzoic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester or a pharmaceutically acceptable salt thereof;
cc) 4-Chloro-benzoic acid 4,5-diacetoxy-6-(3-acetylamino-4-chloro-benzyloxy)-3-(7,8-diacetoxy-2-phenyl-hexahydro-pyrano[3,2-d][1,3]dioxin-6-yloxy)-tetrahydro-pyran-2-ylmethyl ester or a pharmaceutically acceptable salt thereof;
dd) (R)-N-[2-Chloro-5-[[[6-O-(4-chloro-3-nitrobenzoyl)-4-O-[4,6O-(phenylmethylene)-α-D-glucopyranosyl]-β-D-glucopyranosyl]oxy]methyl]phenyl]acetamide or a pharmaceutically acceptable salt thereof;
ee) N-{5-[(2,2',3,-Tri-O-Acetyl-6-O-(4-chloro-3-nitrobenzoyl)-4',6'-O-(benzylidene)-β-D-maltosyl)-oxymethyl]-2-chloro-phenyl)-acetamide or a pharmaceutically acceptable salt thereof;
ff) (R)-N-[2-Chloro-5-[[[6-O-(4-cyanobenzoyl)-4-O-[4,6O-(phenylmethylene)-α-D-glucopyranosyl]-β-D-glucopyranosyl]oxy]methyl]phenyl]acetamide or a pharmaceutically acceptable salt thereof;
gg) (R)-N-[2-Chloro-5-[[[6-O-(4-nitrobenzoyl)-4-O-[4,6O-(phenylmethylene)-α-D-glucopyranosyl]-β-D-glucopyranosyl]oxy]methyl]phenyl]acetamide or a pharmaceutically acceptable salt thereof;
hh) N-{5-[(4',6'-O-Benzylidene-6-O-(3-iodo)-benzoyl-β-D-maltosyl)-oxy-methyl]-2-chloro-phenyl}-acetamide or a pharmaceutically acceptable salt thereof;
ii) N-{5-[(4',6'-O-Benzylidene-6-(4-iodo-benzoyl)-oxy-β-D-maltosyl)-oxy-methyl]-2-chloro-phenyl}-acetamide or a pharmaceutically acceptable salt thereof;
jj) (R)-N-[2-Chloro-5-[[[2,3-di-O-acetyl-4-O-[2,3-di-O-acetyl-4,6-O-(phenyl-methylene)-α-D-glucopyranosyl]-6-O-(phenylacetyl)-β-D-glucopyranosyl]-oxy]methyl] phenyl]acetamide or a pharmaceutically acceptable salt thereof;
kk) N-{5-[(4',6'-O-Benzylidene-6-O-phenyl-propyl-carboxyl-β-D-maltosyl)-oxy-methyl]-2-chloro-phenyl}-acetamide or a pharmaceutically acceptable salt thereof;
ll) Diphenyl-acetic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester or a pharmaceutically acceptable salt thereof;
mm) Diphenyl-acetic acid 4,5-diacetoxy-6-(3-acetylamino-4-chloro-benzyloxy)-3-(7,8-diacetoxy-2-phenyl-hexahydro-pyrano[3,2-d][1,3]dioxin-6-yloxy)-tetrahydro-pyran-2-ylmethyl ester or a pharmaceutically acceptable salt thereof;
nn) (3,4-Dimethoxy-phenyl)-acetic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester or a pharmaceutically acceptable salt thereof;
oo) (3,4-Dimethoxy-phenyl)-acetic acid 4,5-diacetoxy-6-(3-acetylamino-4-chloro-benzyloxy)-3-(7,8-diacetoxy-2-phenyl-hexahydro-pyrano[3,2-d][1,3]dioxin-6-yloxy)-tetrahydro-pyran-2-ylmethyl ester or a pharmaceutically acceptable salt thereof;
pp) Nicotinic acid 6-(3-acetylamino-4-chloro-benzyloxy)-3-(7,8-dihydroxy-2-phenyl-hexahydro-pyrano[3,2-d][1,3]dioxin-6-yloxy)-4,5-dihydroxy-tetrahydro-pyran-2-ylmethyl ester or a pharmaceutically acceptable salt thereof;
qq) Nicotinic acid 4,5-diacetoxy-6-(3-acetylamino-4-chloro-benzyloxy)-3-(7,8-diacetoxy-2-phenyl-hexahydro-pyrano[3,2-d][1,3]dioxin-6-yloxy)-tetrahydro-pyran-2-ylmethyl ester or a pharmaceutically acceptable salt thereof;

rr) (R)-N-[5-[[[6-O-(4-Benzoylbenzoyl)-4-O-[4,6-O-(phenylmethylene)-α-D-glucopyranosyl]-β-D-glucopyranosyl]oxy]methyl]-2-chlorophenyl]acetamide or a pharmaceutically acceptable salt thereof;

ss) N-{5-[(4',6'-O-Benzylidene-β-maltosyl)-oxy-methyl]-2-methyl-phenyl}-acetamide or a pharmaceutically acceptable salt thereof;

tt) N-Acetyl-{5-[(2,2',3,3',6-penta-O-acetyl-4',6'-O-benzylidene-β-D-maltosyl)-oxy-methyl]-2-methyl-phenyl}acetamide or a pharmaceutically acceptable salt thereof;

uu) N-(5-{[4',6'-O-Benzylidene-6-O-(4-toluenesulfonyl)-β-D-maltosyl]-oxy-methyl}-2-methyl-phenyl)-acetamide or a pharmaceutically acceptable salt thereof;

vv) N-{5-[(4',6'-O-Benzylidene-6-O-phenyl-β-D-maltosyl)-oxy-methyl]-2-chloro-phenyl}-acetamide or a pharmaceutically acceptable salt thereof;

ww) (R)-N-[2-Chloro-5-[[[4-O-[4',6'-O-(phenylmethylene)-α-D-glucopyranosyl]-β-D-glucopyranosyl]oxy]methyl]phenyl]-3-pyridinecarboxamide or a pharmaceutically acceptable salt thereof;

xx) (R)-N-[5-[[[6-O-Benzoyl-4-O-[4',6'-O-(phenylmethylene)-α-D-glucopyranosyl]-β-D-glucopyranosyl]oxy]methyl]-2-chlorophenyl]-3-pyridinecarboxamide or a pharmaceutically acceptable salt thereof;

yy) Furan-2-carboxylic acid {5-[(4',6'-O-benzylidene-β-D-maltosyl)-oxy-methyl]-2-chloro-phenyl}-amide or a pharmaceutically acceptable salt thereof;

zz) Furan-2-carboxylic acid {5-[(6-O-benzoyl-4',6'-O-benzylidene-β-D-maltosyl)-oxy-methyl]-2-chloro-phenyl}-amide or a pharmaceutically acceptable salt thereof;

aaa) N-{2-Chloro-5-[(4',6'-O-benzylidene-β-D-maltosyl)-oxy-methyl]-phenyl}-pent-4-enamide or a pharmaceutically acceptable salt thereof;

bbb) N-{2-Chloro-5-[(6-O-benzoyl-4',6'-O-benzilidene-β-D-maltosyl)-oxy-methyl]-phenyl}-pent-4-enamide or a pharmaceutically acceptable salt thereof;

ccc) 5-(6-O-Benzoyl-4',6'-O-benzylidene-β-D-maltosyl)-oxy-methyl-2-chloro-phenylamine or a pharmaceutically acceptable salt thereof;

ddd) (4-Chloro)-benzyl-4',6'-O-benzylidene-β-D-maltoside or a pharmaceutically acceptable salt thereof;

eee) Benzoic acid 1-O-(4-chloro)-benzyl-4',6'-O-benzylidene-6-deoxy-β-D-malto-6-yl ester or a pharmaceutically acceptable salt thereof;

fff) 4-Benzoyl-N-{5-[(4',6'-O-benzylidene-β-D-maltosyl)-oxy-methyl] -2-chloro-phenyl}-benzamide or a pharmaceutically acceptable salt thereof;

ggg) 4-Benzoyl-N-{5-[(6-benzoyl-oxy-4',6'-O-benzylidene-β-D-maltosyl)-oxy-methyl]-2-chloro-phenyl}-benzoic acid amide or a pharmaceutically acceptable salt thereof;

hhh) 4-Benzoyl-N-{5-[(4',6'-O-benzylidene-6-O-(3-iodo-benzoyl-β-D-maltosyl)-oxy-methyl]-2-chloro-phenyl}-benzamide or a pharmaceutically acceptable salt thereof;

iii) 4-Benzoyl-N-{5-[(4',6'-O-benzylidene-6-(4-iodo-benzoyl)-oxy-β-D-maltosyl)-oxy-methyl]-2-chloro-phenyl}-benzoic acid amide or a pharmaceutically acceptable salt thereof;

jjj) (1-{5-[(4',6'-O-Benzylidene-β-D-maltosyl)-oxy-methyl]-2-chloro-phenyl-carbamoyl}ethyl)-carbamic acid 9H-fluoren-9ylmethyl ester or a pharmaceutically acceptable salt thereof;

kkk) N-(9H-Fluoren-9ylmethoxycarbonyl)-N'-{5-[(6-O-benzoyl-4',6'-O-benzylidene-β-D-maltosyl)-oxy-methyl]-2-chloro-phenyl}-L-alaninamide or a pharmaceutically acceptable salt thereof;

lll) N'-{5-[(6-O-benzoyl-4',6'-O-benzylidene-β-D-maltosyl)-oxy-methyl]-2-chloro-phenyl}-L-alaninamide or a pharmaceutically acceptable salt thereof;

mmm) N-{5-[(4',6'-O-Benzylidene-β-D-maltosyl)-oxymethyl]-2-chloro-phenyl}-N-methyl-acetamide or a pharmaceutically acceptable salt thereof;

nnn) N-{5-[(6-O-Benzoyl-4',6'-O-benzylidene-β-D-maltosyl)-oxymethyl]-2-chloro-phenyl}-N-methyl-acetamide or a pharmaceutically acceptable salt thereof;

ooo) N-{5-[(4',6'-O-Benzylidene-β-D-maltosyl)-oxy-methyl]-2-chloro-phenyl}-carbamic acid methyl ester or a pharmaceutically acceptable salt thereof;

ppp) N-{5-[(6-O-(3-Benzyl-1-oxo-propyl)-4',6'-O-benzylidene-β-D-maltosyl)-oxy-methyl]-2-chloro-phenyl}-carbamic acid methyl ester or a pharmaceutically acceptable salt thereof;

qqq) N-{5-[(4',6'-O-Benzylidene-β-D-maltosyl)-oxy-methyl]-2-chloro-phenyl}-methanesulfonamide or a pharmaceutically acceptable salt thereof;

rrr) N-{5-[(6-O-Benzoyl-4',6'-O-benzylidene-β-D-maltosyl)-oxy-methyl]-2-cyano-phenyl}-acetamide or a pharmaceutically acceptable salt thereof;

sss) N-{5-[(6-O-Benzoyl-4',6'-O-benzylidene-β-D-maltosyl)-oxy-methyl]-2-methyl-phenyl}-acetamide or a pharmaceutically acceptable salt thereof;

ttt) 6-[-6-(4-Chloro-3-nitro-benzylsulfanyl)-4,5-dihydroxy-2-hydroxymethyl-tetrahydro-pyran-3-yloxy]-2-phenyl-hexahydro-pyrano[3,2-d][1,3]dioxine-7,8-diol or a pharmaceutically acceptable salt thereof.

20. A method of treating or inhibiting hyperproliferative vascular disorders in a mammal in need thereof, which comprises administering to said mammal an effective amount of a compound of formula I having the structure

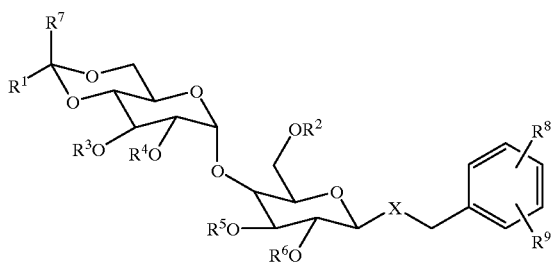

wherein

X is O or S;

$R^1$ is alkyl of 1–6 carbon atoms, haloalkyl of 1–6 carbon atoms, nitroalkyl of 1–6 carbon atoms, cyanoalkyl of 1–6 carbon atoms, alkoxyalkyl of 2–12 carbon atoms, phenyl mono-, di-, or tri-substituted with $R^8$, phenylalkyl of 7–10 carbon atoms, wherein the phenyl ring is mono-, di-, or tri-substituted with $R^8$, pyridyl substituted with $R^8$, furyl substituted with $R^8$, thienyl substituted with $R^8$, and thiazolyl substituted with $R^8$;

$R^2$ is hydrogen, acyl of 2–6 carbon atoms, haloacyl of 2–6 carbon atoms, nitroacyl of 2–7 carbon atoms, cyanoacyl of 2–7 carbon atoms, or trifluoromethylacyl of 3–8 carbon atoms, carboalkoxyacyl of 4–12 carbon atoms,

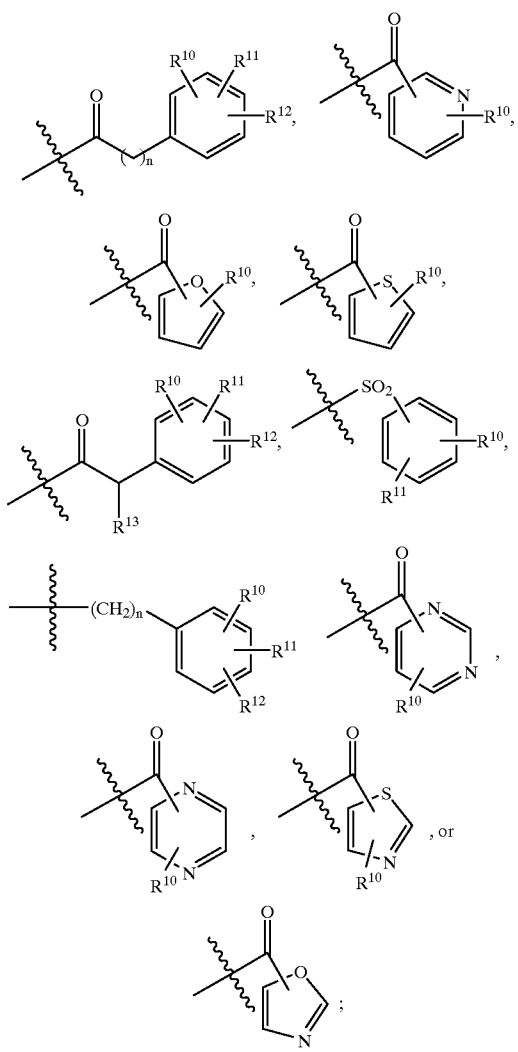

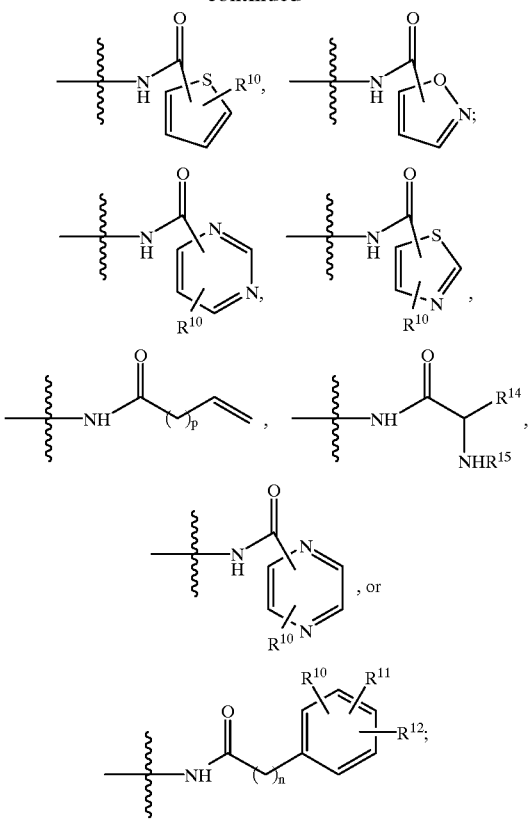

R³, R⁴, R⁵, and R⁶ are each, independently, hydrogen, acyl of 2–7 carbon atoms, benzoyl, wherein the phenyl moiety is mono-, di-, or tri-substituted with R⁸, haloacyl of 2–7 carbon atoms, nitroacyl of 2–7 carbon atoms, cyanoacyl of 2–7 carbon atoms, or trifluoromethylacyl of 3–8 carbon atoms;

R⁷ is hydrogen, methyl, or phenyl;

R⁸ is hydrogen, alkyl of 1–6 carbon atoms, alkoxy of 1–6 carbon atoms, phenyl, —CN, —NO₂, halogen, or —CF₃;

R⁹ is hydrogen, alkyl of 1–6 carbon atoms, alkoxy of 1–6 carbon atoms, phenyl, —CN, —NO₂, halogen, —CF₃, —NHR³, —NR³R³, —NR³R¹⁴, —NHCO₂R¹⁴, —NHSO₂R¹⁴,

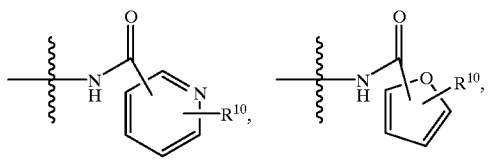

R¹⁰, R¹¹, and R¹², are each, independently, hydrogen, alkyl of 1–6 carbon atoms, alkoxy of 1–6 carbon atoms, phenyl, —CN, —NO₂, halogen, —CF₃, acyl of 2–7 carbon atoms, or benzoyl, wherein the phenyl group or the phenyl moiety of the benzoyl group is optionally mono-, di-, or tri-substituted with alkyl of 1–6 carbon atoms, alkoxy of 1–6 carbon atoms, —CN, —NO₂, halogen, or —CF₃;

R¹³ is hydrogen, alkyl of 1–6 carbon atoms, alkoxy of 1–6 carbon atoms, —CN, —NO₂, halogen, —CF₃, or phenyl group, wherein the phenyl moiety is optionally mono-, di-, or tri-substituted with alkyl of 1–6 carbon atoms, alkoxy of 1–6 carbon atoms, or halogen;

R¹⁴ is alkyl of 1–6 carbon atoms;

R¹⁵ is hydrogen, acyl of 2–7 carbon atoms, benzoyl, or —CO₂R¹⁶;

R¹⁶ is alkyl of 1–6 carbon atoms, benzyl, phenyl, or fluorenyl;

n=0–3;

p=0–6;

or a pharmaceutically acceptable salt thereof.

21. A method of treating or inhibiting restenosis in a mammal in need thereof, which comprises administering to said mammal an effective amount of a compound of formula I having the structure

I

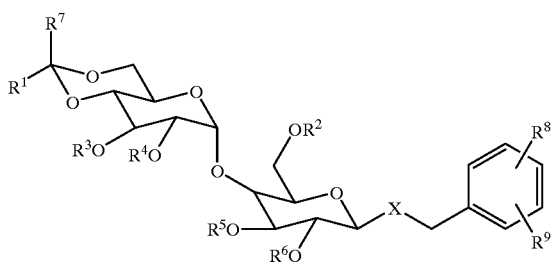

wherein

X is O or S;

R¹ is alkyl of 1–6 carbon atoms, haloalkyl of 1–6 carbon atoms, nitroalkyl of 1–6 carbon atoms, cyanoalkyl of 1–6 carbon atoms, alkoxyalkyl of 2–12 carbon atoms, phenyl mono-, di-, or tri-substituted with R⁸, phenylalkyl of 7–10 carbon atoms, wherein the phenyl ring is mono-, di-, or tri-substituted with R⁸, pyridyl substituted with R⁸, furyl substituted with R⁸, thienyl substituted with R⁸, and thiazolyl substituted with R⁸;

R² is hydrogen, acyl of 2–6 carbon atoms, haloacyl of 2–6 carbon atoms, nitroacyl of 2–7 carbon atoms, cyanoacyl of 2–7 carbon atoms, or trifluoromethylacyl of 3–8 carbon atoms, carboalkoxyacyl of 4–12 carbon atoms,

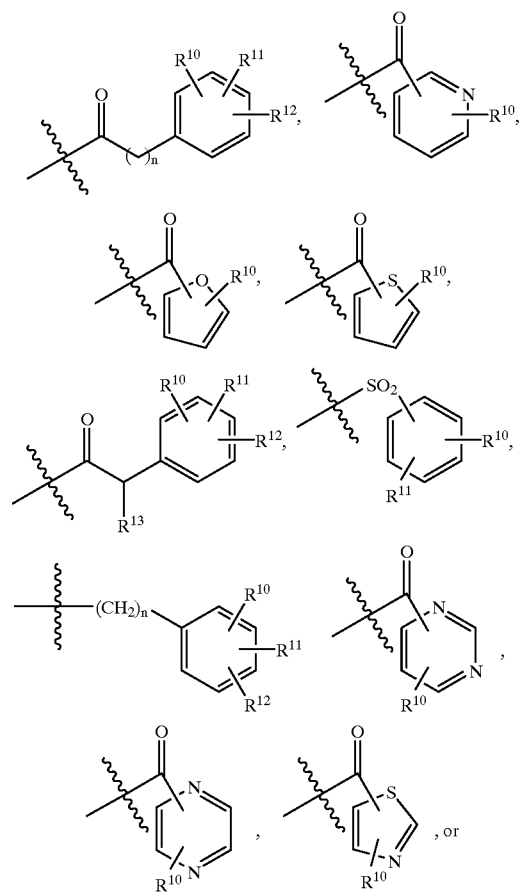

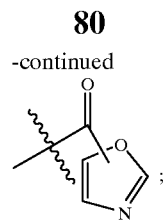

R³, R⁴, R⁵, and R⁶ are each, independently, hydrogen, acyl of 2–7 carbon atoms, benzoyl, wherein the phenyl moiety is mono-, di-, or tri-substituted with R⁸, haloacyl of 2–7 carbon atoms, nitroacyl of 2–7 carbon atoms, cyanoacyl of 2–7 carbon atoms, or trifluoromethylacyl of 3–8 carbon atoms;

R⁷ is hydrogen, methyl, or phenyl;

R⁸ is hydrogen, alkyl of 1–6 carbon atoms, alkoxy of 1–6 carbon atoms, phenyl, —CN, —NO₂, halogen, or —CF₃;

R⁹ is hydrogen, alkyl of 1–6 carbon atoms, alkoxy of 1–6 carbon atoms, phenyl, —CN, —NO₂, halogen, —CF₃, —NHR³, —NR³R³, —NR³R¹⁴, —NHCO₂R¹⁴, —NHSO₂R¹⁴,

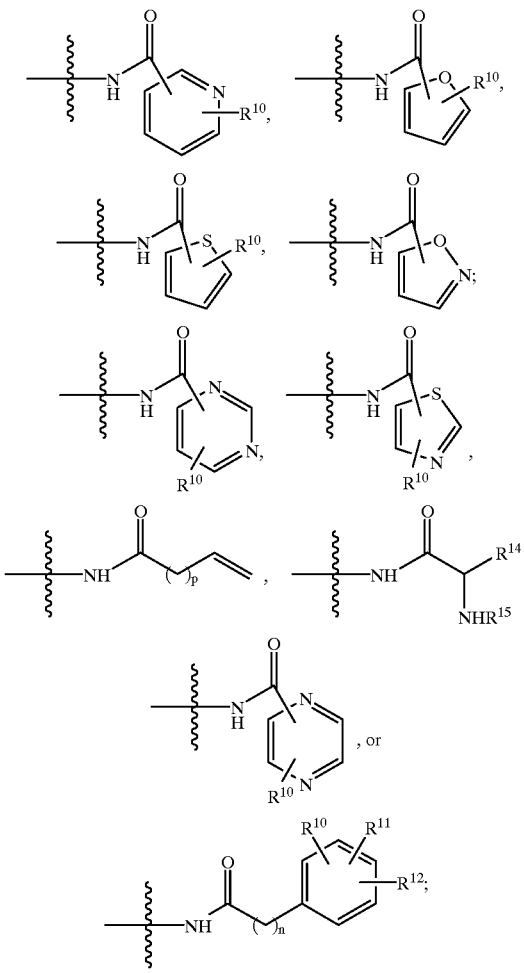

R¹⁰, R¹¹, and R¹², are each, independently, hydrogen, alkyl of 1–6 carbon atoms, alkoxy of 1–6 carbon atoms, phenyl, —CN, —NO₂, halogen, —CF₃, acyl of 2–7 carbon atoms, or benzoyl, wherein the phenyl group or the phenyl moiety of the benzoyl group is optionally mono-, di, or tri-substituted with alkyl of 1–6 carbon atoms, alkoxy of 1–6 carbon atoms, —CN, —NO$_2$, halogen, or —CF$_3$;

$R^{13}$ is hydrogen, alkyl of 1–6 carbon atoms, alkoxy of 1–6 carbon atoms, —CN, —NO$_2$, halogen, —CF$_3$, or phenyl group, wherein the phenyl moiety is optionally mono-, di-, or tri-substituted with alkyl of 1–6 carbon atoms, alkoxy of 1–6 carbon atoms, or halogen;

$R^{14}$ is alkyl of 1–6 carbon atoms;

$R^{15}$ is hydrogen, acyl of 2–7 carbon atoms, benzoyl, or —CO$_2$R$^{16}$;

$R^{16}$ is alkyl of 1–6 carbon atoms, benzyl, phenyl, or fluorenyl;

n=0–3;

p=0–6;

or a pharmaceutically acceptable salt thereof.

22. The method according to claim 21, wherein the restenosis results from a vascular angioplasty procedure, vascular reconstructive surgery, or organ or tissue transplantation.

23. A method of inhibiting angiogenesis in a malignant tumor, sarcoma, or neoplastic tissue in a mammal in need thereof, which comprises administering to said mammal an effective amount of a compound of formula I having the structure

I

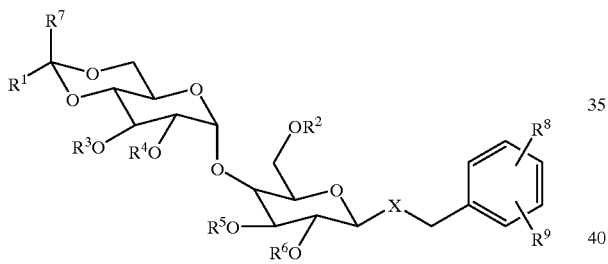

wherein

X is O or S;

$R^1$ is alkyl of 1–6 carbon atoms, haloalkyl of 1–6 carbon atoms, nitroalkyl of 1–6 carbon atoms, cyanoalkyl of 1–6 carbon atoms, alkoxyalkyl of 2–12 carbon atoms, phenyl mono-, di-, or tri-substituted with $R^8$, phenylalkyl of 7–10 carbon atoms, wherein the phenyl ring is mono-, di-, or tri-substituted with $R^8$, pyridyl substituted with $R^8$, furyl substituted with $R^8$, thienyl substituted with $R^8$, and thiazolyl substituted with $R^8$;

$R^2$ is hydrogen, acyl of 2–6 carbon atoms, haloacyl of 2–6 carbon atoms, nitroacyl of 2–7 carbon atoms, cyanoacyl of 2–7 carbon atoms, or trifluoromethylacyl of 3–8 carbon atoms, carboalkoxyacyl of 4–12 carbon atoms,

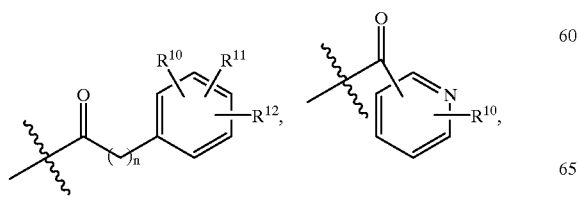

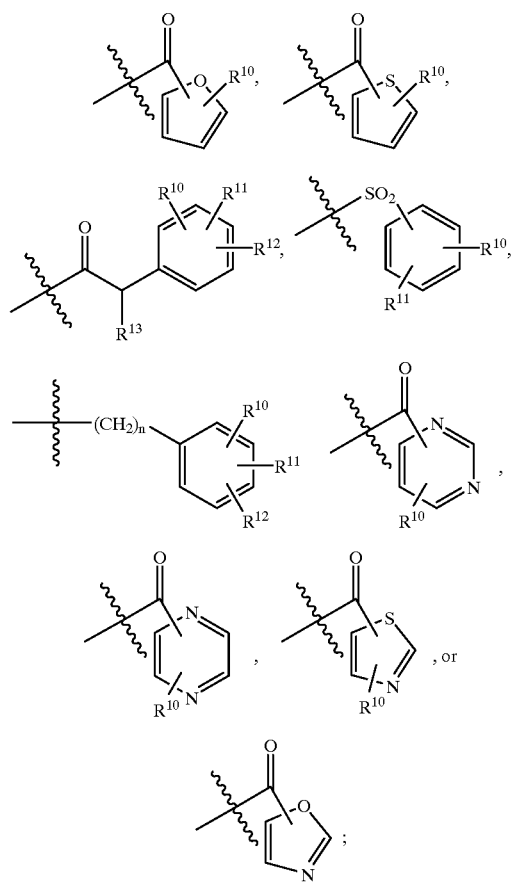

$R^3$, $R^4$, $R^5$, and $R^6$ are each, independently, hydrogen, acyl of 2–7 carbon atoms, benzoyl, wherein the phenyl moiety is mono-, di-, or tri-substituted with $R^8$, haloacyl of 2–7 carbon atoms, nitroacyl of 2–7 carbon atoms, cyanoacyl of 2–7 carbon atoms, or trifluoromethylacyl of 3–8 carbon atoms;

$R^7$ is hydrogen, methyl, or phenyl;

$R^8$ is hydrogen, alkyl of 1–6 carbon atoms, alkoxy of 1–6 carbon atoms, phenyl, —CN, —NO$_2$, halogen, or —CF$_3$;

$R^9$ is hydrogen, alkyl of 1–6 carbon atoms, alkoxy of 1–6 carbon atoms, phenyl, —CN, —NO$_2$, halogen, —CF$_3$, —NHR$^3$, —NR$^3$R$^3$, —NR$^3$R$^{14}$, —NHCO$_2$R$^{14}$, —NHSO$_2$R$^{14}$,

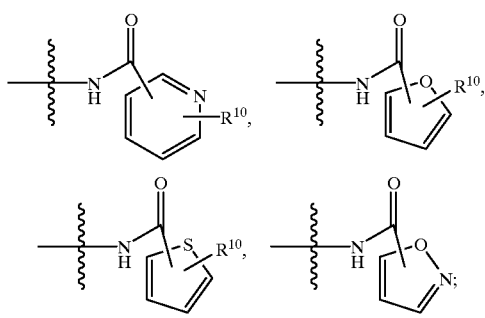

-continued

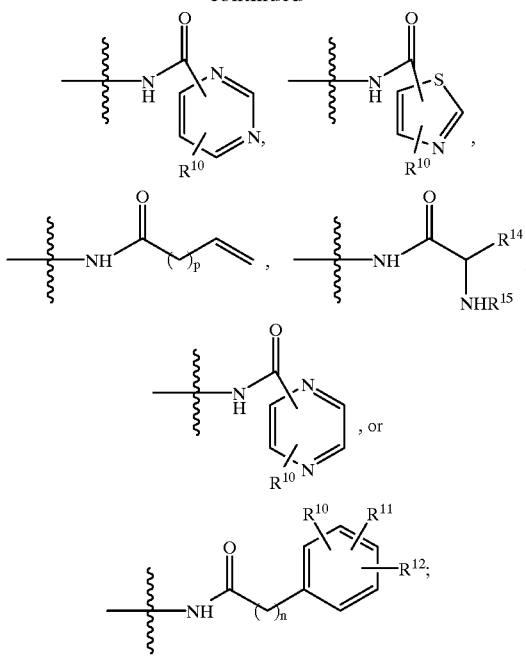

R$^{10}$, R$^{11}$, and R$^{12}$, are each, independently, hydrogen, alkyl of 1–6 carbon atoms, alkoxy of 1–6 carbon atoms, phenyl, —CN, —NO$_2$, halogen, —CF$_3$, acyl of 2–7 carbon atoms, or benzoyl, wherein the phenyl group or the phenyl moiety of the benzoyl group is optionally mono-, di-, or tri-substituted with alkyl of 1–6 carbon atoms, alkoxy of 1–6 carbon atoms, —CN, —NO$_2$, halogen, or —CF$_3$;

R$^{13}$ is hydrogen, alkyl of 1–6 carbon atoms, alkoxy of 1–6 carbon atoms, —CN, —NO$_2$, halogen, —CF$_3$, or phenyl group, wherein the phenyl moiety is optionally mono-, di-, or tri-substituted with alkyl of 1–6 carbon atoms, alkoxy of 1–6 carbon atoms, or halogen;

R$^{14}$ is alkyl of 1–6 carbon atoms;

R$^{15}$ is hydrogen, acyl of 2–7 carbon atoms, benzoyl, or —CO$_2$R$^{16}$;

R$^{16}$ is alkyl of 1–6 carbon atoms, benzyl, phenyl, or fluorenyl;

n=0–3;

p=0–6;

or a pharmaceutically acceptable salt thereof.

24. A pharmaceutical composition which comprises a compound of formula I having the structure

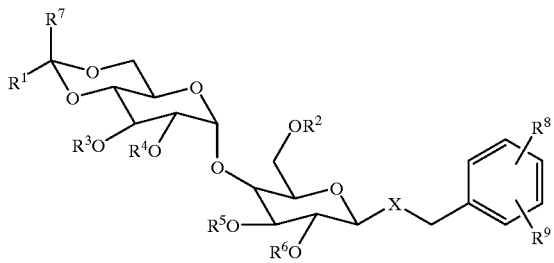

I wherein

X is O or S;

R$^1$ is alkyl of 1–6 carbon atoms, haloalkyl of 1–6 carbon atoms, nitroalkyl of 1–6 carbon atoms, cyanoalkyl of 1–6 carbon atoms, alkoxyalkyl of 2–12 carbon atoms, phenyl mono-, di-, or tri-substituted with R$^8$, phenylalkyl of 7–10 carbon atoms, wherein the phenyl ring is mono-, di-, or tri-substituted with R$^8$, pyridyl substituted with R$^8$, furyl substituted with R$^8$, thienyl substituted with R$^8$, and thiazolyl substituted with R$^8$;

R$^2$ is hydrogen, acyl of 2–6 carbon atoms, haloacyl of 2–6 carbon atoms, nitroacyl of 2–7 carbon atoms, cyanoacyl of 2–7 carbon atoms, or trifluoromethylacyl of 3–8 carbon atoms, carboalkoxyacyl of 4–12 carbon atoms,

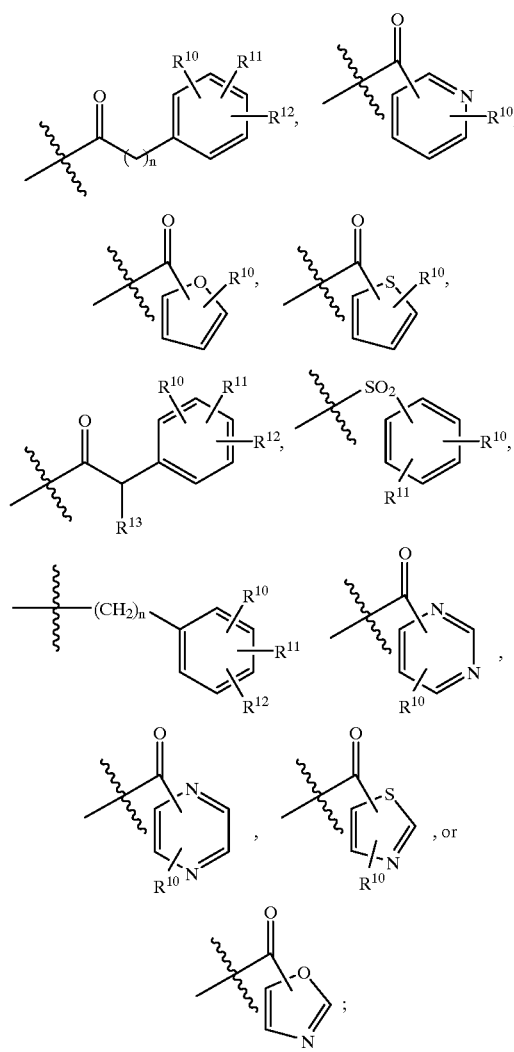

R$^3$, R$^4$, R$^5$, and R$^6$ are each, independently, hydrogen, acyl of 2–7 carbon atoms, benzoyl, wherein the phenyl moiety is mono-, di-, or tri-substituted with R$^8$, haloacyl of 2–7 carbon atoms, nitroacyl of 2–7 carbon atoms, cyanoacyl of 2–7 carbon atoms, or trifluoromethylacyl of 3–8 carbon atoms;

R$^7$ is hydrogen;

R$^8$ is hydrogen, alkyl of 1–6 carbon atoms, alkoxy of 1–6 carbon atoms, phenyl, —CN, —NO$_2$, halogen, or —CF$_3$;

R⁹ is hydrogen, alkyl of 1–6 carbon atoms, alkoxy of 1–6 carbon atoms, phenyl, —CN, —NO$_2$, halogen, —CF$_3$, —NHR$^3$, —NR$^3$R$^3$, —NR$^3$R$^{14}$, —NHCO$_2$R$^{14}$, —NHSO$_2$R$^{14}$,

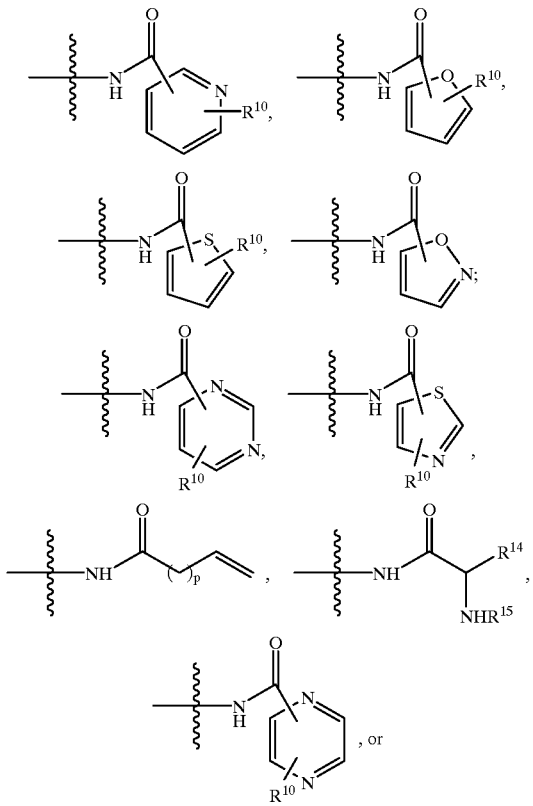

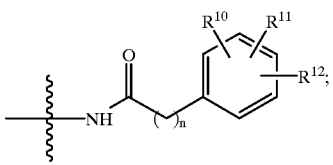

R$^{10}$, R$^{11}$, and R$^{12}$, are each, independently, hydrogen, alkyl of 1–6 carbon atoms, alkoxy of 1–6 carbon atoms, phenyl, —CN, —NO$_2$, halogen, —CF$_3$, acyl of 2–7 carbon atoms, or benzoyl, wherein the phenyl group or the phenyl moiety of the benzoyl group is optionally mono-, di-, or tri-substituted with alkyl of 1–6 carbon atoms, alkoxy of 1–6 carbon atoms, —CN, —NO$_2$, halogen, or —CF$_3$;

R$^{13}$ is hydrogen, alkyl of 1–6 carbon atoms, alkoxy of 1–6 carbon atoms, —CN, —NO$_2$, halogen, —CF$_3$, or phenyl group, wherein the phenyl moiety is optionally mono-, di-, or tri-substituted with alkyl of 1–6 carbon atoms, alkoxy of 1–6 carbon atoms, or halogen;

R$^{14}$ is alkyl of 1–6 carbon atoms;

R$^{15}$ is hydrogen, acyl of 2–7 carbon atoms, benzoyl, or —CO$_2$R$^{16}$;

R$^{16}$ is alkyl of 1–6 carbon atoms, benzyl, phenyl, or fluorenyl;

n=0–3;

p=0–6;

or a pharmaceutically acceptable salt thereof, and a pharmaceutical carrier.

* * * * *